(12) United States Patent
Suzuki et al.

(10) Patent No.: US 11,510,987 B2
(45) Date of Patent: *Nov. 29, 2022

(54) ENDOCYTOSIS ENHANCER FOR DRUG DELIVERY SYSTEM

(71) Applicants: Saitama University, Saitama (JP); QUARRYMEN & Co. Inc., Tokyo (JP)

(72) Inventors: Miho Suzuki, Saitama (JP); Ken Hatano, Saitama (JP); Shojiro Yoshida, Saitama (JP); Yasuhiro Yamashita, Tokyo (JP)

(73) Assignees: Saitama University, Saitama (JP); QUARRYMEN & Co. Inc., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 16/426,184

(22) Filed: Aug. 7, 2019

(65) Prior Publication Data
US 2019/0358333 A1    Nov. 28, 2019

Related U.S. Application Data

(63) Continuation of application No. PCT/JP2017/043373, filed on Dec. 1, 2017.

(30) Foreign Application Priority Data

Dec. 1, 2016 (JP) .................................. 2016-234547

(51) Int. Cl.
| | | |
|---|---|---|
| A61K 47/42 | (2017.01) | |
| A61K 9/107 | (2006.01) | |
| A61K 38/17 | (2006.01) | |
| A61K 38/22 | (2006.01) | |
| A61K 39/395 | (2006.01) | |
| A61K 47/24 | (2006.01) | |

(52) U.S. Cl.
CPC .............. *A61K 47/42* (2013.01); *A61K 9/107* (2013.01); *A61K 38/1732* (2013.01); *A61K 38/22* (2013.01); *A61K 39/395* (2013.01); *A61K 47/24* (2013.01)

(58) Field of Classification Search
CPC ...................................................... A61K 47/42
See application file for complete search history.

(56) References Cited

U.S. PATENT DOCUMENTS

| | | | |
|---|---|---|---|
| 2007/0287681 A1* | 12/2007 | Jeong ...................... | A61K 47/60 514/44 A |
| 2011/0091561 A1 | 4/2011 | Schreiber | |
| 2013/0131155 A1 | 5/2013 | Sun et al. | |
| 2014/0100266 A1 | 4/2014 | Dutreix et al. | |
| 2017/0281782 A1 | 10/2017 | Suzuki et al. | |

FOREIGN PATENT DOCUMENTS

| | | | | |
|---|---|---|---|---|
| JP | 07-224093 A | 8/1995 | | |
| JP | 2010-112777 | * 5/2010 | ............. | G01N 21/78 |
| JP | 2011-520936 A | 7/2011 | | |
| JP | 2013-534521 A | 9/2013 | | |
| JP | 2014-516977 A | 7/2014 | | |
| JP | 5629888 B2 | 11/2014 | | |
| WO | WO 2011/050178 | * 4/2011 | ............. | A61K 47/42 |
| WO | 20160084979 A1 | 6/2016 | | |

OTHER PUBLICATIONS

Tsien, 1998, The Green Fluorescent Protein, Annu Rev Biochem, 67: 509-544.*
Raghunathan et al., 2014, A variant of green fluorescent protein exclusively deposited to active intracellular inclusion bodies, Microbial Cell Factories, 13: 68 (11 pages).*
Shvets et al., 2008, Autophagy-independent incorporation of GFP-LC3 into protein aggregates is dependent on its interaction with P62/SQSTM1, Autophagy, 4(8): 1054-1056.*
Raghunathan et al., 2013, Modulation of protein stability and aggregation properties by surface charge engineering, Mol BioSyst, 9: 2379-2389.*
Zietkiewicz et al., 2004, Successive and Synergistic Action of the Hsp70 and Hsp100 Chaperones in Protein Disaggregation, The Journal of Biological Chemistry, 279(43): 44376-44383.*
Tsumoto et al., 2003, Solubilization of active green fluorescent protein from insoluble particles by guanidine and arginine, Biochemical and Biophysical Research Communications, 312: 1383-1386.*
Link et al., 2006, Conversion of Green Fluorescent Protein into a Toxic, Aggregation-prone Protein by C-terminal Addition of a Short Peptide, The Journal of Biological Chemistry, 281(3): 1808-1816.*
Peters et al., 2007, Protein Aggregation and Polyasparagine-Mediated Cellular Toxicity in *Saccharomyces cerevisiae*, Prion, 1(2): 144-153.*
Moulder et al., 1999, Generation of Neuronal Intranuclear Inclusions by Polyglutamine-GFP: Analysis of Inclusion Clearance and Toxicity as a Function of Polyglutamine Length, The Journal of Neuroscience, 19(2): 705-715.*

(Continued)

*Primary Examiner* — Amber D Steele
(74) *Attorney, Agent, or Firm* — Locke Lord LLP; James E. Armstrong, IV; Nicholas J. DiCeglie, Jr.

(57) ABSTRACT

The present invention addresses the problem of providing an endocytosis enhancer comprising associates formed from a fluorescent protein. The fluorescent protein is preferably any one selected from the group consisting of a white fluorescent protein, a red fluorescent protein, a yellow fluorescent protein, a blue fluorescent protein and a green fluorescent protein. The endocytosis enhancer according to the present invention can enhance the cellular uptake of a drug, which is encapsulated in micelles each formed from a fluorescent-protein-supported carbosilane dendrimer, through endocytosis.

13 Claims, 23 Drawing Sheets

Specification includes a Sequence Listing.

(56) References Cited

OTHER PUBLICATIONS

Medrano et al., 2008, GFP-Tagged Mutant Prion Protein Forms Intra-Axonal Aggregates in Transgenic Mice, Neurobiol Dis, 31(1): 20-32.*
Katayama et al., 2008, GFP-like Proteins Stably Accumulate in Lysosomes, Cell Structure and Function, 33: 1-12.*
Hatano et al., 2009, Fluorescence quenching detection of peanut agglutinin based on photoluminescnet silole-core carbosilane dendrimer peripherally functionalized with lactose, Tetrahedron Letters, 50: 5816-5819.*
Aizawa et al., 2012, A carbosilane dendrimer and a silacyclopentadiene analog carrying peripheral lactoses as drug-delivery systems, Bioorganic & Medicinal Chemistry Letters, 22: 3564-3566.*
Hatano et al., 2007, Highly luminescent glycocluster: silole-core carbosilane dendrimer having peripheral globotriaose, Tetrahedron Letters, 48: 4365-4368.*
Y. Hong et al., "Aggregation-induced emission: phenomenon, mechanism and applications," Chem. Commun. 2009, pp. 4332-4353. (discussed in the spec).
D. S. Goodsell, "GFP-like Proteins", PDB-101: Molecule of the Month, Jun. 2014, 4 pages and Englsih translation thereof, (discussed in the spec).
International Search Report dated Mar. 6, 2018, issued for PCT/JP2017/043373.

* cited by examiner

R-S-CH$_2$-R' + XH

Fig. 10 (A) Laser475(FITC)
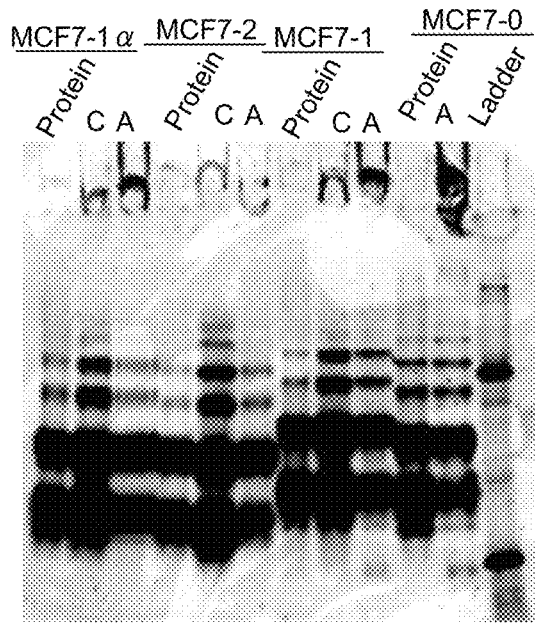
Fig. 10 (B) PMT500
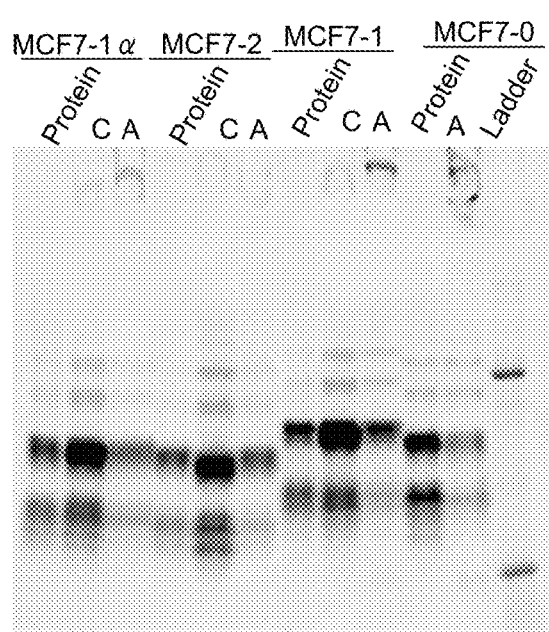
Fig. 10 (C) Laser635(cy5)
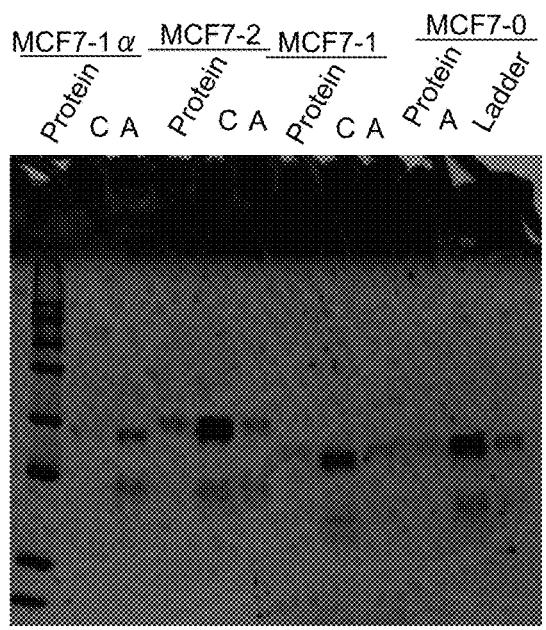
Fig. 10 (D) PMT500
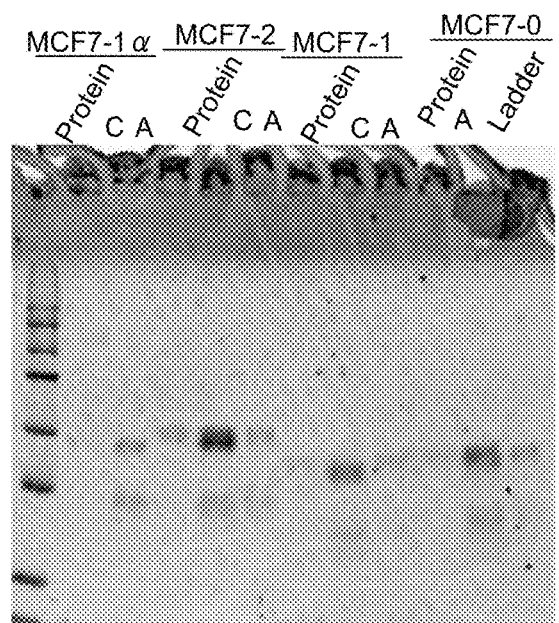

Fig. 11 (A) Laser475(FITC)
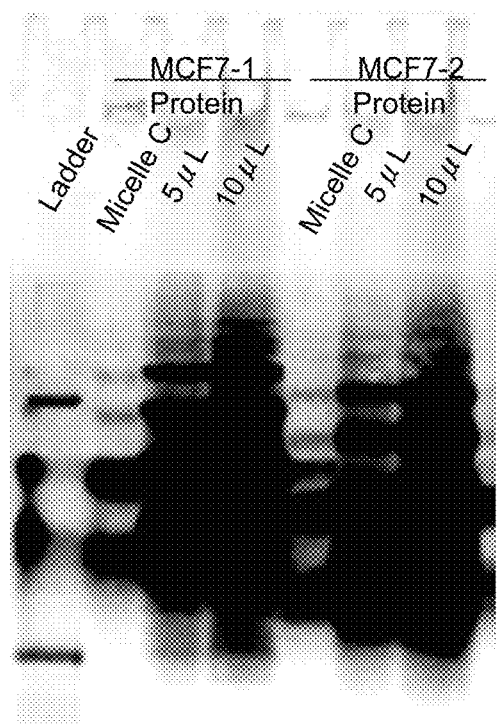
Fig. 11 (B) PMT500
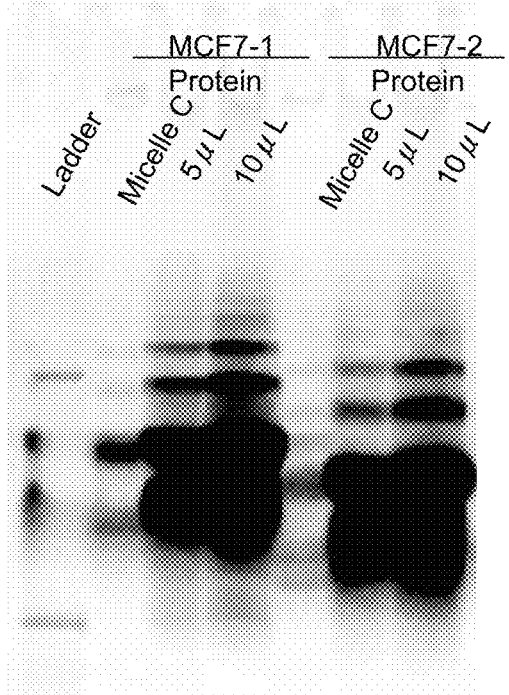
Fig. 11 (C) Laser635(cy5)
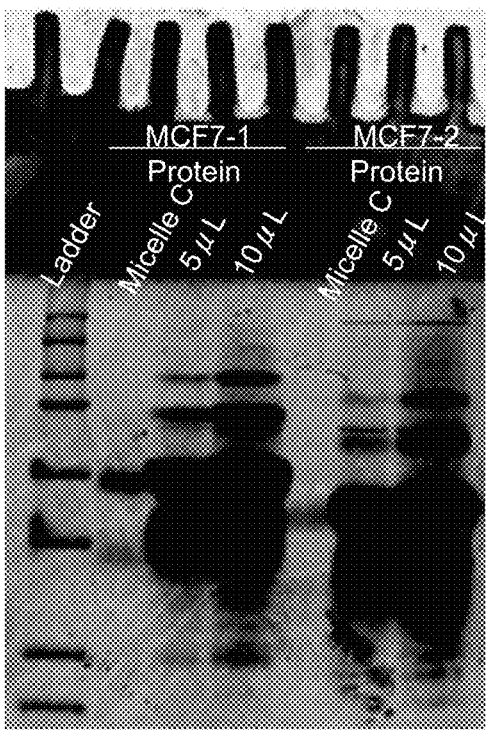
Fig. 11 (D) PMT500
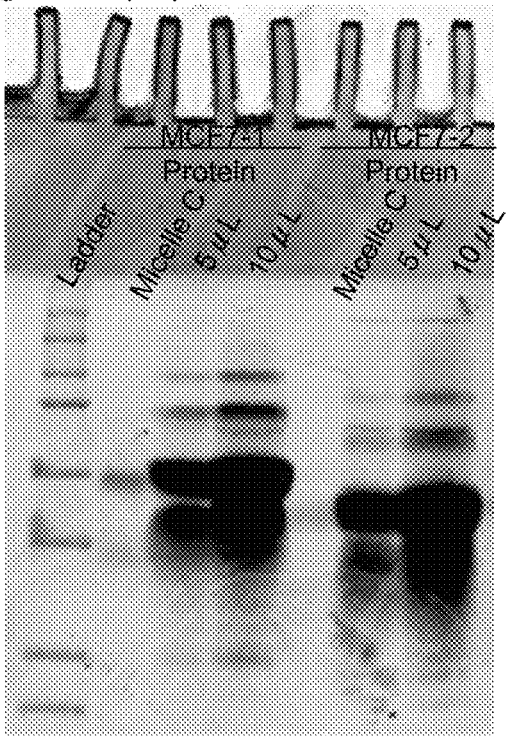

Correlation between Amount and Fluorescence ratio of the value at Excitation wavelength of 370 nm or 488 nm – that of 510 nm (the micelle only; data (i) to (vi))

Excitation Wavelength 370 nm or 488 nm, measurement of fluorescence wavelength 510 nm Correlation between Amount and Fluorescence ratio of the value at Excitation wavelength of 370 nm or 488 nm − that of 510 nm (per each derivative micelle only; data (i) to (vi))

Excitation Wavelength 370 nm or 488 nm, measurement of fluorescence wavelength 510 nm

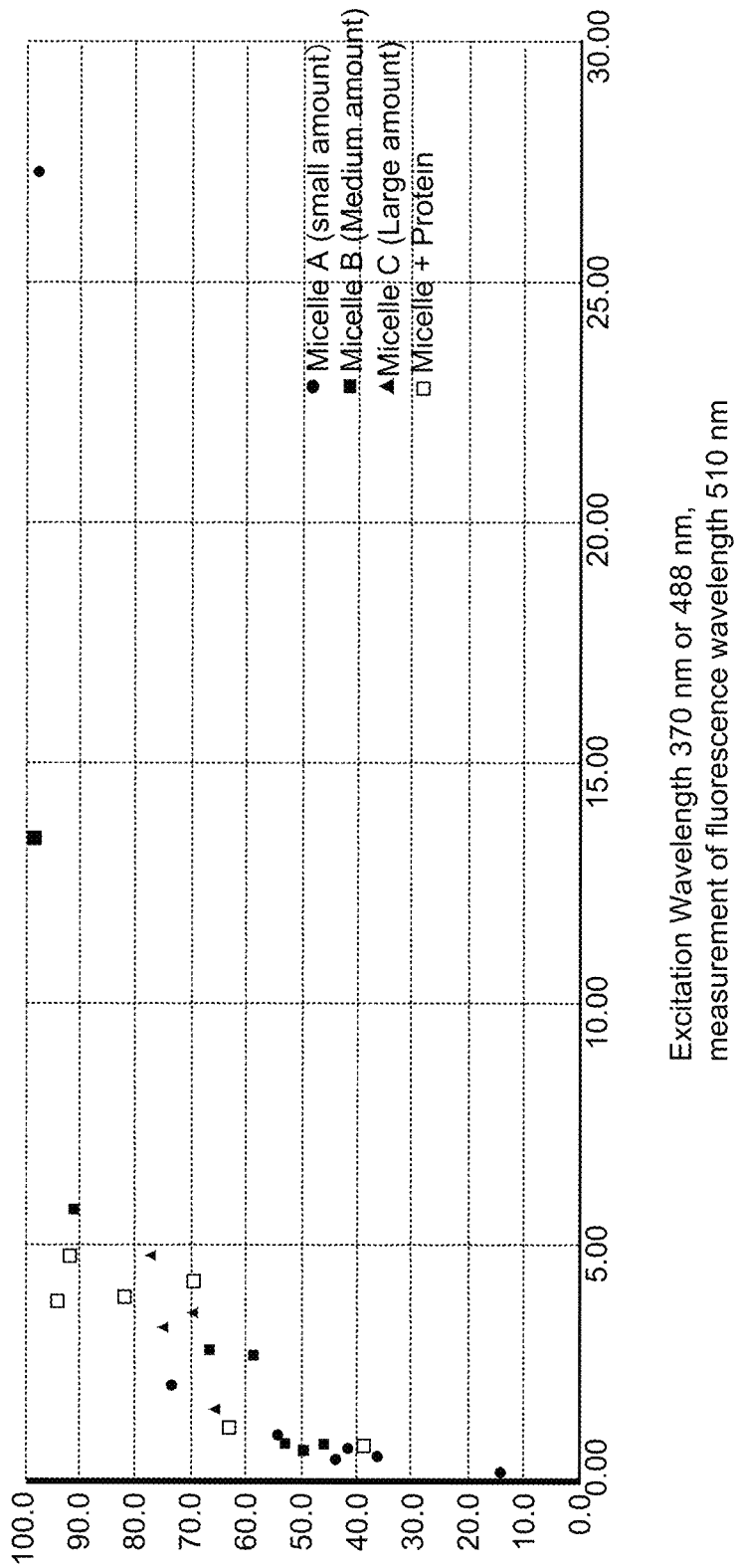

Fig. 16 (A) The micelle size distribution when 50 mM Tris-HCl buffer (pH 8.0) is used (Micelle fraction solution)

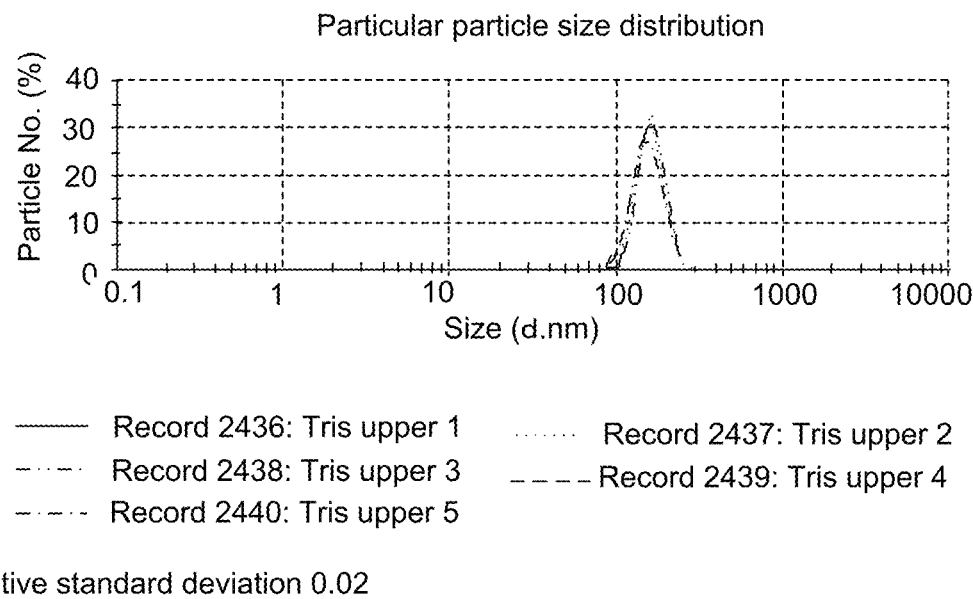

——— Record 2436: Tris upper 1   ······ Record 2437: Tris upper 2
—··— Record 2438: Tris upper 3   — — — Record 2439: Tris upper 4
—·—·· Record 2440: Tris upper 5

Relative standard deviation 0.02

Fig. 16 (B) The micelle size distribution when 50 mM Tris-HCl buffer (pH 8.0) is used (Unreacted micelle fraction solution)

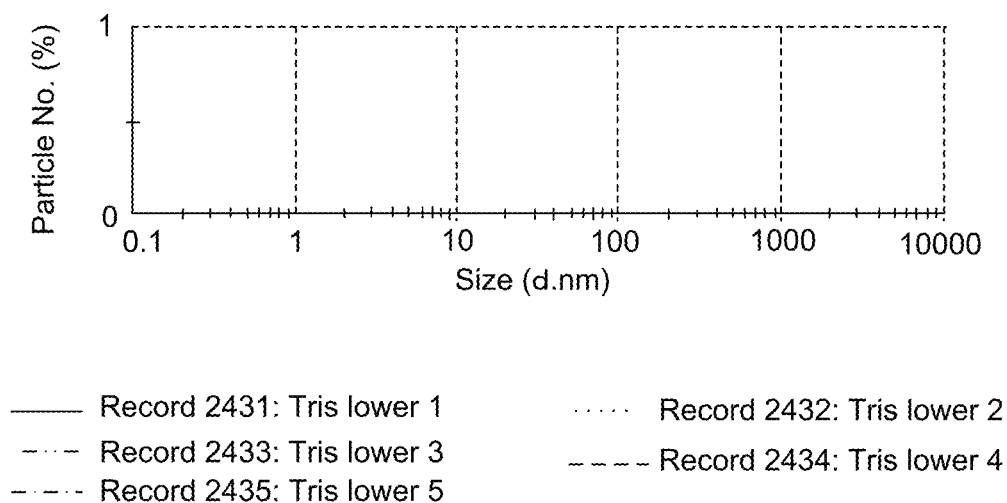

——— Record 2431: Tris lower 1   ····· Record 2432: Tris lower 2
—··— Record 2433: Tris lower 3   — — — Record 2434: Tris lower 4
—·—·· Record 2435: Tris lower 5

Fig. 17 (A) The micelle size distribution when 50 mM HEPES buffer (pH 7.6) is used (Micelle fraction solution)
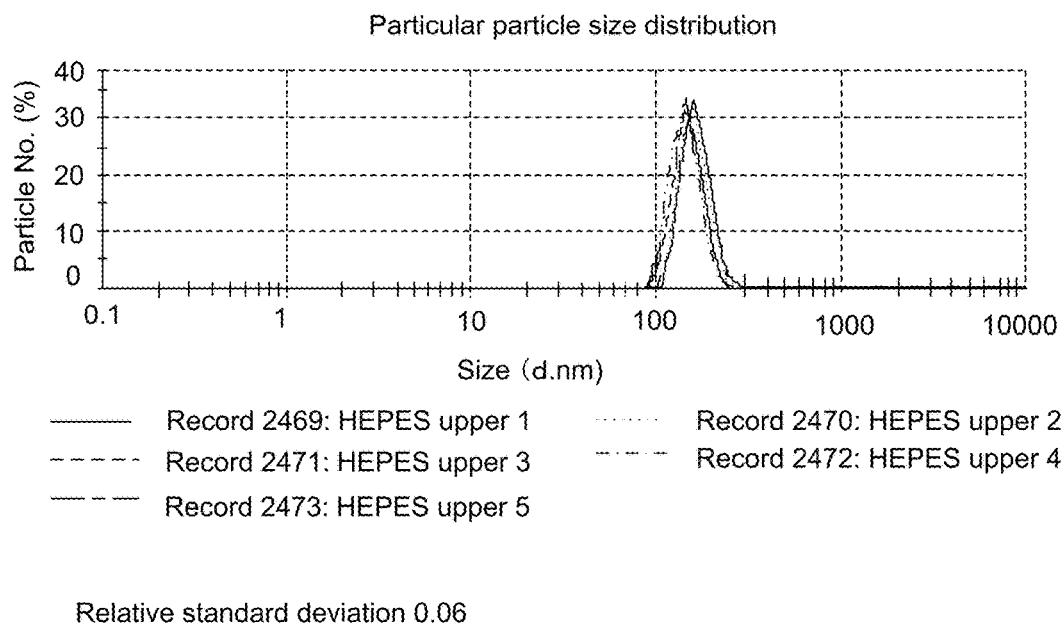
Relative standard deviation 0.06
Fig. 17 (B) The micelle size distribution when 50 mM HEPES buffer (pH 7.6) is used (Unreacted micelle fraction)
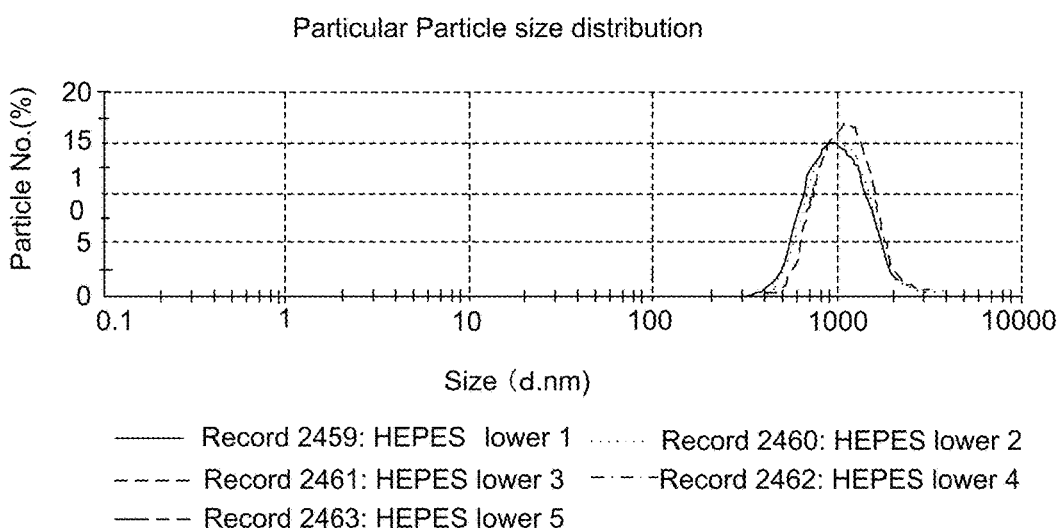

Fig. 18 (A) The micelle size distribution when 50 mM Sodium citrate buffer (pH 7.6) is used (the micelle fraction)
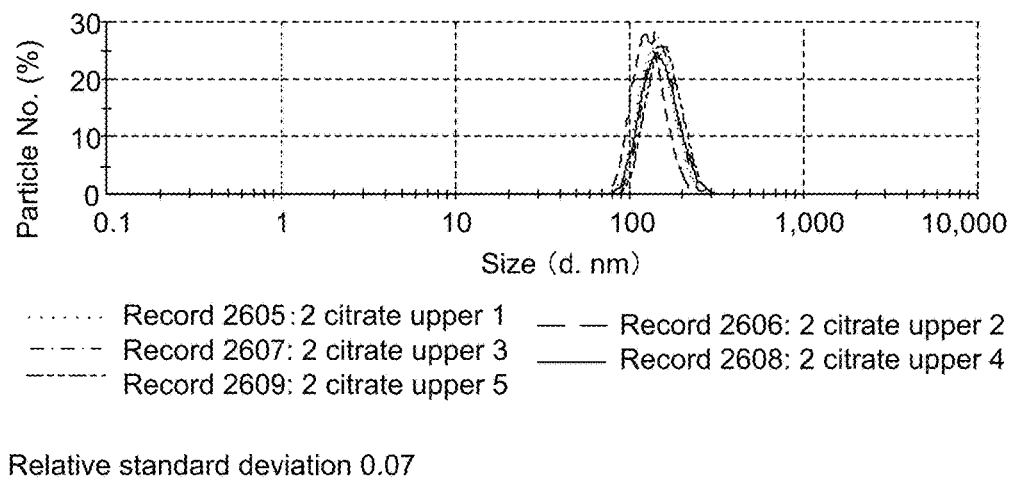
·······  Record 2605: 2 citrate upper 1      — —  Record 2606: 2 citrate upper 2
— · —   Record 2607: 2 citrate upper 3      ———  Record 2608: 2 citrate upper 4
— — —   Record 2609: 2 citrate upper 5
Relative standard deviation 0.07
Fig. 18 (B) The micelle size distribution when 50 mM Citrate buffer (pH 7.6) is used (Unreacted micelle fraction)
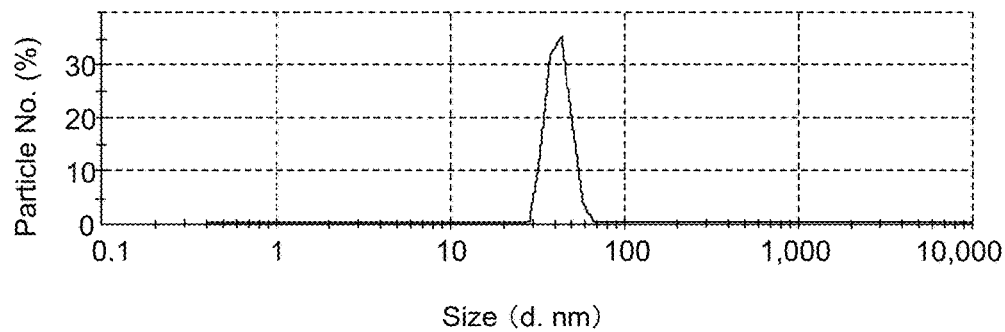

Fig. 19 (A) Particle size distribution of the micelle when 50 mM carbonate-sodium bicarbonate buffer (pH 8.36) (The micelle fraction)
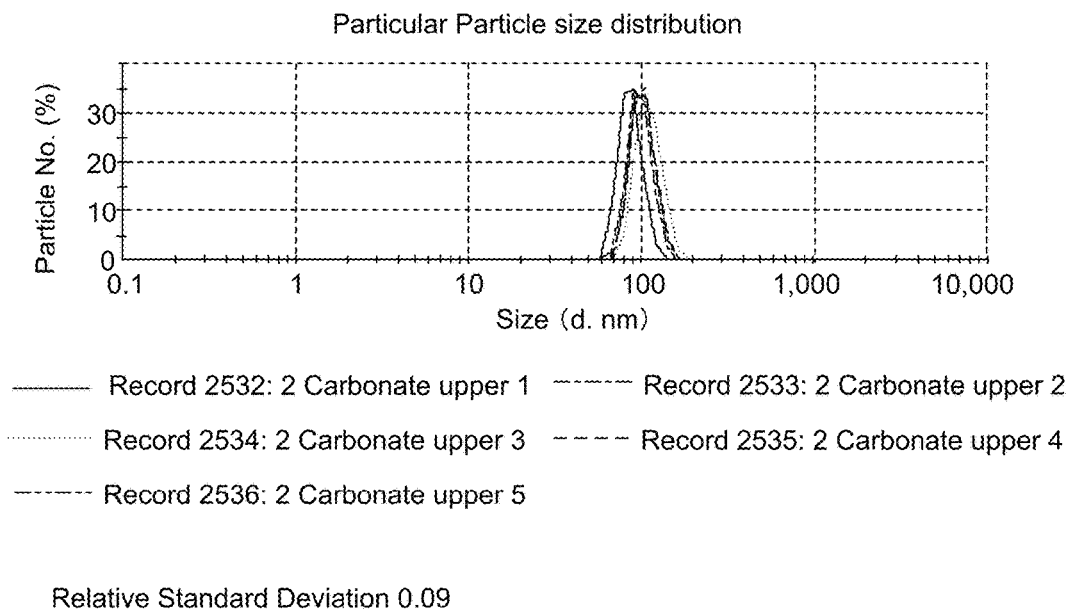
Relative Standard Deviation 0.09
Fig. 19 (B) The particle diameter distribution of the micelle when 50 mM Carbonate - bicarbonate buffer (pH 8.36) is used (unreacted micelle fraction)
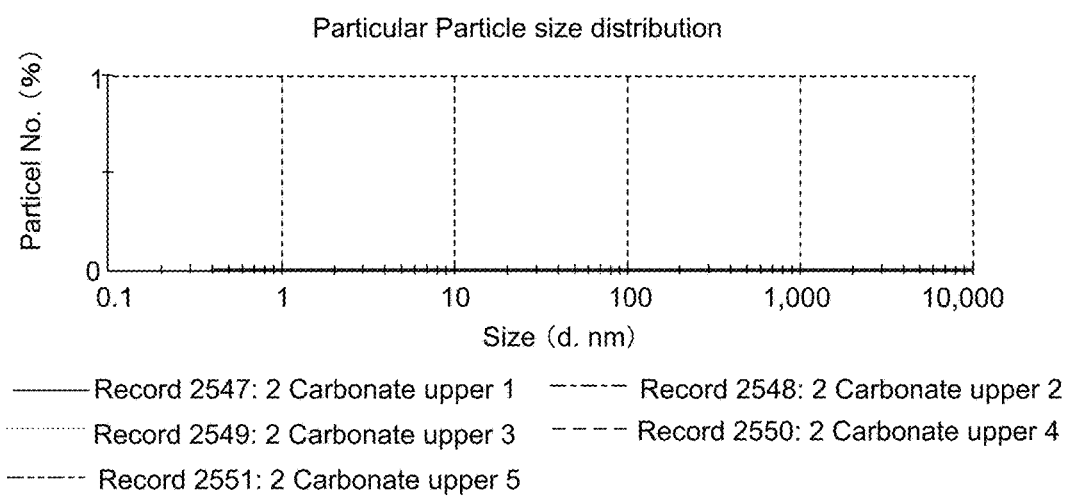

Result of the fluorescence measurement
when 50 mM Tris – HCl buffer is used.

Fluorescence property of the micelle when 50 mM HEPES buffer (pH 7.6) is used

Fluorescence property of the micelle when
50 mM Citrate buffer (pH 7.6) is used

Fluorescence property of the micelle when 50 mM
Carbonate − sodium bicarbonate buffer (pH 8.36) is used

SEQUENCE LISTING

```
<160> NUMBER OF SEQ ID NOS: 34

<210> SEQ ID NO 1
<211> LENGTH: 10
<212> TYPE: PRT
<213> ORGANISM: Homo sapiens
<220> FEATURE:
<221> NAME/KEY: PEPTIDE
<222> LOCATION: (1)..(10)
<223> OTHER INFORMATION: MCF7-1

<400> SEQUENCE: 1

Asp Met Pro Gly Thr Val Leu Pro Gly Gly
1               5                   10

<210> SEQ ID NO 2
<211> LENGTH: 10
<212> TYPE: PRT
<213> ORGANISM: Homo sapiens
<220> FEATURE:
<221> NAME/KEY: PEPTIDE
<222> LOCATION: (1)..(10)
<223> OTHER INFORMATION: MCF7-2
```

-continued

```
<400> SEQUENCE: 2

Val Pro Thr Asp Thr Asp Tyr Ser Gly Gly
1               5                   10

<210> SEQ ID NO 3
<211> LENGTH: 29
<212> TYPE: PRT
<213> ORGANISM: Homo sapiens
<220> FEATURE:
<221> NAME/KEY: PEPTIDE
<222> LOCATION: (1)..(29)
<223> OTHER INFORMATION: MCF7-1+alpha stand peptide

<400> SEQUENCE: 3

Asp Met Pro Gly Thr Val Leu Pro Gly Gly Gly Gly Ser Glu Gly
1               5                   10                  15

Glu Trp Gln Gln Gln Gln His Gln Trp Ala Lys Gln Glu
                20                  25

<210> SEQ ID NO 4
<211> LENGTH: 272
<212> TYPE: PRT
<213> ORGANISM: Aequorea victoria
<220> FEATURE:
<221> NAME/KEY: PEPTIDE
<222> LOCATION: (1)..(272)

<400> SEQUENCE: 4

Met Ala Ser Met Thr Gly Gly Gln Gln Met Gly Arg Asp Met Pro Gly
1               5                   10                  15

Thr Val Leu Pro Gly Gly Met Ser Lys Gly Glu Glu Leu Phe Thr Gly
                20                  25                  30

Val Val Pro Ile Leu Val Glu Leu Asp Gly Asp Val Asn Gly His Lys
            35                  40                  45

Phe Ser Val Ser Gly Glu Gly Glu Gly Asp Ala Thr Tyr Gly Lys Leu
        50                  55                  60

Thr Leu Lys Phe Ile Ser Thr Thr Gly Lys Leu Pro Val Pro Trp Pro
65                  70                  75                  80

Thr Leu Val Thr Thr Leu Thr Tyr Gly Val Gln Cys Phe Ser Arg Tyr
                85                  90                  95

Pro Asp His Met Lys Arg His Asp Phe Phe Lys Ser Ala Met Pro Glu
            100                 105                 110

Gly Tyr Val Gln Glu Arg Thr Ile Ser Phe Lys Asp Asp Gly Asn Tyr
        115                 120                 125

Lys Thr Arg Ala Glu Val Lys Phe Glu Gly Asp Thr Leu Val Asn Arg
130                 135                 140

Ile Glu Leu Lys Gly Ile Asp Phe Lys Glu Asp Gly Asn Ile Leu Gly
145                 150                 155                 160

His Lys Leu Glu Tyr Asn Tyr Asn Ser His Asn Val Tyr Ile Thr Ala
                165                 170                 175

Asp Lys Gln Arg Asn Gly Ile Lys Ala Asn Phe Lys Thr Arg His Asn
            180                 185                 190

Ile Glu Asp Gly Ser Val Gln Leu Ala Asp His Tyr Gln Gln Asn Thr
        195                 200                 205

Pro Ile Gly Asp Gly Pro Val Leu Leu Pro Asp Asn His Tyr Leu Ser
    210                 215                 220

Thr Gln Ser Ala Leu Leu Lys Asp Pro Asn Glu Lys Arg Asp His Met
225                 230                 235                 240
```

```
Val Leu Leu Glu Phe Val Thr Ala Ala Gly Ser Gly Ile Thr Asp Glu
                245                 250                 255

Val Asp Gly Thr Glu Leu Tyr Lys Gly Gly His His His His His His
            260                 265                 270

<210> SEQ ID NO 5
<211> LENGTH: 272
<212> TYPE: PRT
<213> ORGANISM: Aequorea victoria
<220> FEATURE:
<221> NAME/KEY: PEPTIDE
<222> LOCATION: (1)..(272)

<400> SEQUENCE: 5

Met Ala Ser Met Thr Gly Gly Gln Gln Met Gly Arg Val Pro Thr Asp
1               5                   10                  15

Thr Asp Tyr Ser Gly Gly Met Ser Lys Gly Glu Glu Leu Phe Thr Gly
            20                  25                  30

Val Val Pro Ile Leu Val Glu Leu Asp Gly Asp Val Asn Gly His Lys
        35                  40                  45

Phe Ser Val Ser Gly Glu Gly Glu Gly Asp Ala Thr Tyr Gly Lys Leu
    50                  55                  60

Thr Leu Lys Phe Ile Ser Thr Thr Gly Lys Leu Pro Val Pro Trp Pro
65                  70                  75                  80

Thr Leu Val Thr Thr Leu Thr Tyr Gly Val Gln Cys Phe Ser Arg Tyr
                85                  90                  95

Pro Asp His Met Lys Arg His Asp Phe Phe Lys Ser Ala Met Pro Glu
            100                 105                 110

Gly Tyr Val Gln Glu Arg Thr Ile Ser Phe Asn Asp Asp Gly Asn Tyr
        115                 120                 125

Lys Thr Arg Ala Glu Val Lys Phe Glu Gly Asp Thr Leu Val Asn Arg
    130                 135                 140

Ile Glu Leu Lys Gly Ile Asp Phe Lys Glu Asp Gly Asn Ile Leu Gly
145                 150                 155                 160

His Lys Leu Glu Tyr Asn Tyr Asn Ser His Asn Val Tyr Ile Thr Ala
                165                 170                 175

Asp Lys Gln Arg Asn Gly Ile Lys Ala Asn Phe Lys Thr Arg His Asn
            180                 185                 190

Ile Glu Asp Gly Ser Val Gln Leu Ala Asp His Tyr Gln Gln Asn Thr
        195                 200                 205

Pro Ile Gly Asp Gly Pro Val Leu Leu Pro Asp Asn His Tyr Leu Ser
    210                 215                 220

Thr Gln Ser Ala Leu Leu Lys Asp Pro Asn Asp Lys Arg Asp His Met
225                 230                 235                 240

Val Leu Leu Glu Phe Val Thr Ala Ala Gly Ser Gly Ile Thr Asp Glu
                245                 250                 255

Val Asp Gly Thr Glu Leu Tyr Lys Gly Gly His His His His His His
            260                 265                 270

<210> SEQ ID NO 6
<211> LENGTH: 292
<212> TYPE: PRT
<213> ORGANISM: Aequorea victoria
<220> FEATURE:
<221> NAME/KEY: PEPTIDE
<222> LOCATION: (1)..(292)

<400> SEQUENCE: 6
```

Met Ala Ser Met Thr Gly Gly Gln Gln Met Gly Arg Asp Met Pro Gly
1               5                   10                  15

Thr Val Leu Pro Gly Gly Gly Gly Ser Glu Gly Glu Trp Gln Gln
            20                  25                  30

Gln Gln His Gln Trp Ala Lys Gln Glu Met Ser Lys Gly Glu Glu Leu
        35                  40                  45

Phe Thr Gly Val Val Pro Ile Leu Val Glu Leu Asp Gly Asp Val Asn
    50                  55                  60

Gly His Lys Phe Ser Val Ser Gly Glu Gly Glu Gly Asp Ala Thr Tyr
65                  70                  75                  80

Gly Lys Leu Thr Leu Lys Phe Ile Ser Thr Thr Gly Lys Leu Pro Val
                85                  90                  95

Pro Trp Pro Thr Leu Val Thr Thr Leu Thr Tyr Gly Val Gln Cys Phe
            100                 105                 110

Ser Arg Tyr Pro Asp His Met Lys Arg His Asp Phe Phe Lys Ser Ala
            115                 120                 125

Met Pro Glu Gly Tyr Val Gln Glu Arg Thr Ile Ser Phe Lys Asp Asp
        130                 135                 140

Gly Asn Tyr Lys Thr Arg Ala Glu Val Lys Phe Glu Gly Asp Thr Leu
145                 150                 155                 160

Val Asn Arg Ile Glu Leu Lys Gly Ile Asp Phe Lys Glu Asp Gly Asn
                165                 170                 175

Ile Leu Gly His Lys Leu Glu Tyr Asn Tyr Asn Ser His Asn Val Tyr
            180                 185                 190

Ile Thr Ala Asp Lys Gln Arg Asn Gly Ile Lys Ala Asn Phe Lys Thr
        195                 200                 205

Arg His Asn Ile Glu Asp Gly Ser Val Gln Leu Ala Asp His Tyr Gln
        210                 215                 220

Gln Asn Thr Pro Ile Gly Asp Gly Pro Val Leu Leu Pro Asp Asn His
225                 230                 235                 240

Tyr Leu Ser Thr Gln Ser Ala Leu Leu Lys Asp Pro Asn Glu Lys Arg
                245                 250                 255

Asp His Met Val Leu Leu Glu Phe Val Thr Ala Ala Gly Ser Gly Ile
            260                 265                 270

Thr Asp Glu Val Asp Gly Thr Cys Glu Leu Tyr Lys Gly Gly His His
        275                 280                 285

His His His His
    290

<210> SEQ ID NO 7
<211> LENGTH: 263
<212> TYPE: PRT
<213> ORGANISM: Aequorea victoria
<220> FEATURE:
<221> NAME/KEY: PEPTIDE
<222> LOCATION: (1)..(263)
<223> OTHER INFORMATION: GFP

<400> SEQUENCE: 7

Met Ala Ser Met Thr Gly Gly Gln Gln Met Gly Arg Met Ser Lys Gly
1               5                   10                  15

Glu Glu Leu Phe Thr Gly Val Val Pro Ile Leu Val Glu Leu Asp Gly
            20                  25                  30

Asp Val Asn Gly His Lys Phe Ser Val Ser Gly Glu Gly Glu Gly Asp
        35                  40                  45

```
Ala Thr Tyr Gly Lys Leu Thr Leu Lys Phe Ile Ser Thr Thr Gly Lys
 50                  55                  60

Leu Pro Val Pro Trp Pro Thr Leu Val Thr Thr Leu Thr Tyr Gly Val
 65                  70                  75                  80

Gln Cys Phe Ser Arg Tyr Pro Asp His Met Lys Arg His Asp Phe Phe
                 85                  90                  95

Lys Ser Ala Met Pro Glu Gly Tyr Val Gln Glu Arg Thr Ile Ser Phe
            100                 105                 110

Lys Asp Asp Gly Asn Tyr Lys Thr Arg Ala Glu Val Lys Phe Glu Gly
        115                 120                 125

Asp Thr Leu Val Asn Arg Ile Glu Leu Lys Gly Ile Asp Phe Lys Glu
130                 135                 140

Asp Gly Asn Ile Leu Gly His Lys Leu Glu Tyr Asn Tyr Asn Ser His
145                 150                 155                 160

Asn Val Tyr Ile Thr Ala Asp Lys Gln Lys Asn Gly Ile Lys Ala Asn
                165                 170                 175

Phe Lys Thr Arg His Asn Ile Glu Asp Gly Ser Val Gln Leu Ala Asp
            180                 185                 190

His Tyr Gln Gln Asn Thr Pro Ile Gly Asp Gly Pro Val Leu Leu Pro
        195                 200                 205

Asp Asn His Tyr Leu Ser Thr Gln Ser Ala Leu Leu Lys Asp Pro Asn
210                 215                 220

Glu Lys Arg Asp His Met Val Leu Leu Glu Phe Val Thr Ala Ala Gly
225                 230                 235                 240

Ser Gly Ile Thr Asp Glu Val Asp Gly Thr Cys Glu Leu Tyr Lys Gly
                245                 250                 255

Gly His His His His His
            260

<210> SEQ ID NO 8
<211> LENGTH: 258
<212> TYPE: PRT
<213> ORGANISM: Aequorea victoria
<220> FEATURE:
<221> NAME/KEY: PEPTIDE
<222> LOCATION: (1)..(258)
<223> OTHER INFORMATION: GFP

<400> SEQUENCE: 8

Met Ala Ser Met Thr Gly Gly Gln Gln Met Gly Arg Met Ser Lys Gly
 1               5                  10                  15

Glu Glu Leu Phe Thr Gly Val Val Pro Ile Leu Val Glu Leu Asp Gly
                 20                  25                  30

Asp Val Asn Gly His Lys Phe Ser Val Ser Gly Glu Gly Glu Gly Asp
             35                  40                  45

Ala Thr Tyr Gly Lys Leu Thr Leu Lys Phe Ile Cys Thr Thr Gly Lys
 50                  55                  60

Leu Pro Val Pro Trp Pro Thr Leu Val Thr Thr Leu Thr Tyr Gly Val
 65                  70                  75                  80

Gln Cys Phe Ser Arg Tyr Pro Asp His Met Lys Arg His Asp Phe Phe
                 85                  90                  95

Lys Ser Ala Met Pro Glu Gly Tyr Val Gln Glu Arg Thr Ile Ser Phe
            100                 105                 110

Lys Asp Asp Gly Asn Tyr Lys Thr Arg Ala Glu Val Lys Phe Glu Gly
        115                 120                 125

Asp Thr Leu Val Asn Arg Ile Glu Leu Lys Gly Ile Asp Phe Lys Glu
```

```
            130                 135                 140
Asp Gly Asn Ile Leu Gly His Lys Leu Glu Tyr Asn Tyr Asn Ser His
145                 150                 155                 160

Asn Val Tyr Ile Thr Ala Asp Lys Gln Lys Asn Gly Ile Lys Ala Asn
                165                 170                 175

Phe Lys Thr Arg His Asn Ile Glu Asp Gly Ser Val Gln Leu Ala Asp
            180                 185                 190

His Tyr Gln Gln Asn Thr Pro Ile Gly Asp Gly Pro Val Leu Leu Pro
        195                 200                 205

Asp Asn His Tyr Leu Ser Thr Gln Ser Ala Leu Leu Lys Asp Pro Asn
210                 215                 220

Glu Lys Arg Asp His Met Val Leu Leu Glu Phe Val Thr Ala Ala Gly
225                 230                 235                 240

Ile Thr His Gly Met Asp Glu Leu Tyr Lys Gly Gly His His His
                245                 250                 255

His His
```

<210> SEQ ID NO 9
<211> LENGTH: 259
<212> TYPE: PRT
<213> ORGANISM: Aequorea victoria
<220> FEATURE:
<221> NAME/KEY: PEPTIDE
<222> LOCATION: (1)..(259)
<223> OTHER INFORMATION: GFP

<400> SEQUENCE: 9

```
Met Ala Ser Met Thr Gly Gly Gln Gln Met Gly Arg Met Val Ser Lys
1               5                   10                  15

Gly Glu Glu Leu Phe Thr Gly Val Val Pro Ile Leu Val Glu Leu Asp
                20                  25                  30

Gly Asp Val Asn Gly His Lys Phe Ser Val Ser Gly Glu Gly Glu Gly
            35                  40                  45

Asp Ala Thr Tyr Gly Lys Leu Thr Leu Lys Phe Ile Cys Thr Thr Gly
        50                  55                  60

Lys Leu Pro Val Pro Trp Pro Thr Leu Val Thr Thr Leu Thr His Gly
65                  70                  75                  80

Val Gln Cys Phe Ser Arg Tyr Pro Asp His Met Lys Gln His Asp Phe
                85                  90                  95

Phe Lys Ser Ala Met Pro Glu Gly Tyr Val Gln Glu Arg Thr Ile Phe
            100                 105                 110

Phe Lys Asp Asp Gly Asn Tyr Lys Thr Arg Ala Glu Val Lys Phe Glu
        115                 120                 125

Gly Asp Thr Leu Val Asn Arg Ile Glu Leu Lys Gly Ile Asp Phe Lys
    130                 135                 140

Glu Asp Gly Asn Ile Leu Gly His Lys Leu Glu Tyr Asn Phe Asn Ser
145                 150                 155                 160

His Asn Val Tyr Ile Met Ala Asp Lys Gln Lys Asn Gly Ile Lys Val
                165                 170                 175

Asn Phe Lys Ile Arg His Asn Ile Glu Asp Gly Ser Val Gln Leu Ala
            180                 185                 190

Asp His Tyr Gln Gln Asn Thr Pro Ile Gly Asp Gly Pro Val Leu Leu
        195                 200                 205

Pro Asp Asn His Tyr Leu Ser Thr Gln Ser Ala Leu Ser Lys Asp Pro
    210                 215                 220
```

```
Asn Glu Lys Arg Asp His Met Val Leu Leu Glu Phe Val Thr Ala Ala
225                 230                 235                 240

Gly Ile Thr Leu Gly Met Asp Glu Leu Tyr Lys Gly Gly His His His
                245                 250                 255

His His His
```

<210> SEQ ID NO 10
<211> LENGTH: 259
<212> TYPE: PRT
<213> ORGANISM: Aequorea victoria
<220> FEATURE:
<221> NAME/KEY: PEPTIDE
<222> LOCATION: (1)..(259)

<400> SEQUENCE: 10

```
Met Ala Ser Met Thr Gly Gly Gln Gln Met Gly Arg Met Val Ser Lys
1               5                   10                  15

Gly Glu Glu Leu Phe Thr Gly Val Val Pro Ile Leu Val Glu Leu Asp
                20                  25                  30

Gly Asp Val Asn Gly His Lys Phe Ser Val Ser Gly Glu Gly Glu Gly
            35                  40                  45

Asp Ala Thr Tyr Gly Lys Leu Thr Leu Lys Phe Ile Cys Thr Thr Gly
        50                  55                  60

Lys Leu Pro Val Pro Trp Pro Thr Leu Val Thr Thr Phe Gly Tyr Gly
65                  70                  75                  80

Leu Gln Cys Phe Ala Arg Tyr Pro Asp His Met Lys Gln His Asp Phe
                85                  90                  95

Phe Lys Ser Ala Met Pro Glu Gly Tyr Val Gln Glu Arg Thr Ile Phe
            100                 105                 110

Phe Lys Asp Asp Gly Asn Tyr Lys Thr Arg Ala Glu Val Lys Phe Glu
        115                 120                 125

Gly Asp Thr Leu Val Asn Arg Ile Glu Leu Lys Gly Ile Asp Phe Lys
130                 135                 140

Glu Asp Gly Asn Ile Leu Gly His Lys Leu Glu Tyr Asn Tyr Asn Ser
145                 150                 155                 160

His Asn Val Tyr Ile Met Ala Asp Lys Gln Lys Asn Gly Ile Lys Val
                165                 170                 175

Asn Phe Lys Ile Arg His Asn Ile Glu Asp Gly Ser Val Gln Leu Ala
            180                 185                 190

Asp His Tyr Gln Gln Asn Thr Pro Ile Gly Asp Gly Pro Val Leu Leu
        195                 200                 205

Pro Asp Asn His Tyr Leu Ser Tyr Gln Ser Ala Leu Ser Lys Asp Pro
210                 215                 220

Asn Glu Lys Arg Asp His Met Val Leu Leu Glu Phe Val Thr Ala Ala
225                 230                 235                 240

Gly Ile Thr Leu Gly Met Asp Glu Leu Tyr Lys Gly Gly His His His
                245                 250                 255

His His His
```

<210> SEQ ID NO 11
<211> LENGTH: 236
<212> TYPE: PRT
<213> ORGANISM: Actinia equina
<220> FEATURE:
<221> NAME/KEY: PEPTIDE
<222> LOCATION: (1)..(236)
<220> FEATURE:
<221> NAME/KEY: PEPTIDE

<222> LOCATION: (1)..(236)
<223> OTHER INFORMATION: GFP

<400> SEQUENCE: 11

Met Ala Ser Ser Glu Asp Val Ile Lys Glu Phe Met Arg Phe Lys Val
1               5                   10                  15

Arg Met Glu Gly Ser Val Asn Gly His Glu Phe Glu Ile Glu Gly Glu
            20                  25                  30

Gly Glu Gly Arg Pro Tyr Glu Gly Thr Gln Thr Ala Lys Leu Lys Val
        35                  40                  45

Thr Lys Gly Gly Pro Leu Pro Phe Ala Trp Asp Ile Leu Ser Pro Gln
    50                  55                  60

Phe Gln Tyr Gly Ser Lys Val Tyr Val Lys His Pro Ala Asp Ile Pro
65                  70                  75                  80

Asp Tyr Lys Lys Leu Ser Phe Pro Glu Gly Phe Lys Trp Glu Arg Val
                85                  90                  95

Met Asn Phe Glu Asp Gly Gly Val Val Thr Val Thr Gln Asp Ser Ser
            100                 105                 110

Leu Gln Asp Gly Cys Phe Ile Tyr Lys Val Lys Phe Ile Gly Val Asn
        115                 120                 125

Phe Pro Ser Asp Gly Pro Val Met Gln Lys Lys Thr Met Gly Trp Glu
130                 135                 140

Pro Ser Thr Glu Arg Leu Tyr Pro Arg Asp Gly Val Leu Lys Gly Glu
145                 150                 155                 160

Ile His Lys Ala Leu Lys Leu Lys Asp Gly Gly His Tyr Leu Val Glu
                165                 170                 175

Phe Lys Ser Ile Tyr Met Ala Lys Lys Pro Val Gln Leu Pro Gly Tyr
            180                 185                 190

Tyr Tyr Val Asp Ser Lys Leu Asp Ile Thr Ser His Asn Glu Asp Tyr
        195                 200                 205

Thr Ile Val Glu Gln Tyr Glu Arg Thr Glu Gly Arg His His Leu Phe
    210                 215                 220

Leu Gly Thr Cys Gly Gly His His His His His
225                 230                 235

<210> SEQ ID NO 12
<211> LENGTH: 45
<212> TYPE: DNA
<213> ORGANISM: Artificial Sequence
<220> FEATURE:
<223> OTHER INFORMATION: Primer
<220> FEATURE:
<221> NAME/KEY: prim_transcript
<222> LOCATION: (1)..(45)

<400> SEQUENCE: 12
cctggtactg ttcttcctgg tggtatgagt aaaggagaag aactt            45

<210> SEQ ID NO 13
<211> LENGTH: 27
<212> TYPE: DNA
<213> ORGANISM: Artificial Sequence
<220> FEATURE:
<223> OTHER INFORMATION: primer
<220> FEATURE:
<221> NAME/KEY: prim_transcript
<222> LOCATION: (1)..(27)
<223> OTHER INFORMATION: Primer

<400> SEQUENCE: 13
catatcgcga cccatttgct gtccacc                                       27

<210> SEQ ID NO 14
<211> LENGTH: 45
<212> TYPE: DNA
<213> ORGANISM: Artificial Sequence
<220> FEATURE:
<223> OTHER INFORMATION: Primer
<220> FEATURE:
<221> NAME/KEY: prim_transcript
<222> LOCATION: (1)..(45)
<223> OTHER INFORMATION: Primer for MCF7-1

<400> SEQUENCE: 14
actgatactg attatagtgg aggaatgagt aaaggagaag aactt                   45

<210> SEQ ID NO 15
<211> LENGTH: 27
<212> TYPE: DNA
<213> ORGANISM: Artificial Sequence
<220> FEATURE:
<223> OTHER INFORMATION: Primer
<220> FEATURE:
<221> NAME/KEY: prim_transcript
<222> LOCATION: (1)..(27)
<223> OTHER INFORMATION: Primer for MCF7-1

<400> SEQUENCE: 15
aggaacgcga cccatttgct gtccacc                                       27

<210> SEQ ID NO 16
<211> LENGTH: 51
<212> TYPE: DNA
<213> ORGANISM: Artificial Sequence
<220> FEATURE:
<223> OTHER INFORMATION: Primer
<220> FEATURE:
<221> NAME/KEY: prim_transcript
<222> LOCATION: (1)..(51)
<223> OTHER INFORMATION: Primer for MCF7-2

<400> SEQUENCE: 16
caacaacaac aacatcaatg ggcaaaacaa gaaatgagta aaggagaaga a            51

<210> SEQ ID NO 17
<211> LENGTH: 42
<212> TYPE: DNA
<213> ORGANISM: Artificial Sequence
<220> FEATURE:
<223> OTHER INFORMATION: Primer
<220> FEATURE:
<221> NAME/KEY: prim_transcript
<222> LOCATION: (1)..(42)
<223> OTHER INFORMATION: Primer for MCF7-2

<400> SEQUENCE: 17
ccattcacct tcactaccac caccaccacc aggaagaaca gt                      42

<210> SEQ ID NO 18
<211> LENGTH: 22
<212> TYPE: DNA
<213> ORGANISM: Artificial Sequence
<220> FEATURE:
<223> OTHER INFORMATION: Primer
<220> FEATURE:
<221> NAME/KEY: prim_transcript
<222> LOCATION: (1)..(22)
<223> OTHER INFORMATION: Primer for MCF7-1+alpha stand peptide

<400> SEQUENCE: 18
cattgaagat ggctccgttc aa                                                    22

<210> SEQ ID NO 19
<211> LENGTH: 22
<212> TYPE: DNA
<213> ORGANISM: Artificial Sequence
<220> FEATURE:
<223> OTHER INFORMATION: Primer
<220> FEATURE:
<221> NAME/KEY: prim_transcript
<222> LOCATION: (1)..(22)
<223> OTHER INFORMATION: Primer for MCF7-1+alpha stand peptide

<400> SEQUENCE: 19
ttgtggcgag ttttgaagtt ag                                                    22

<210> SEQ ID NO 20
<211> LENGTH: 70
<212> TYPE: DNA
<213> ORGANISM: Artificial Sequence
<220> FEATURE:
<223> OTHER INFORMATION: Primer for inverse PCR
<220> FEATURE:
<221> NAME/KEY: prim_transcript
<222> LOCATION: (1)..(70)
<223> OTHER INFORMATION: Primer for inverse PCR

<400> SEQUENCE: 20
ctcgaccata tggctagcat gactggtgga cagcaaatgg gtcgcatgag taaaggagaa          60
gaacttttca                                                                  70

<210> SEQ ID NO 21
<211> LENGTH: 54
<212> TYPE: DNA
<213> ORGANISM: Artificial Sequence
<220> FEATURE:
<223> OTHER INFORMATION: Primer
<220> FEATURE:
<221> NAME/KEY: prim_transcript
<222> LOCATION: (1)..(54)
<223> OTHER INFORMATION: Primer for inverse PCR

<400> SEQUENCE: 21
tgacgtgaat tcattagtga tggtgatggt gatgtttgta gagctcatcc atgc                54

<210> SEQ ID NO 22
<211> LENGTH: 25
<212> TYPE: DNA
<213> ORGANISM: Artificial Sequence
<220> FEATURE:
<223> OTHER INFORMATION: Primer
<220> FEATURE:
<221> NAME/KEY: prim_transcript
<222> LOCATION: (1)..(25)
<223> OTHER INFORMATION: Primer for inverse PCR
<220> FEATURE:
<221> NAME/KEY: misc_feature
<222> LOCATION: (13)..(14)
<223> OTHER INFORMATION: n is a, c, g, or t

<400> SEQUENCE: 22
cttaaattta ttnnkactgg aaaac                                                 25

<210> SEQ ID NO 23
<211> LENGTH: 20
<212> TYPE: DNA
<213> ORGANISM: Artificial Sequence
<220> FEATURE:

```
<223> OTHER INFORMATION: Primer
<220> FEATURE:
<221> NAME/KEY: prim_transcript
<222> LOCATION: (1)..(20)
<223> OTHER INFORMATION: Primer for inverse PCR

<400> SEQUENCE: 23
ggtaagtttt ccgtatgttg                                              20

<210> SEQ ID NO 24
<211> LENGTH: 26
<212> TYPE: DNA
<213> ORGANISM: Artificial Sequence
<220> FEATURE:
<223> OTHER INFORMATION: Oligonucleotide
<220> FEATURE:
<221> NAME/KEY: misc_binding
<222> LOCATION: (1)..(26)
<220> FEATURE:
<221> NAME/KEY: misc_feature
<222> LOCATION: (9)..(10)
<223> OTHER INFORMATION: n is a, c, g, or t

<400> SEQUENCE: 24
gtgttcaann kttttcccgt tatccg                                       26

<210> SEQ ID NO 25
<211> LENGTH: 22
<212> TYPE: DNA
<213> ORGANISM: Artificial Sequence
<220> FEATURE:
<223> OTHER INFORMATION: Oligonucleotide
<220> FEATURE:
<221> NAME/KEY: misc_binding
<222> LOCATION: (1)..(22)

<400> SEQUENCE: 25
catacgtcag agtagtgaca ag                                           22

<210> SEQ ID NO 26
<211> LENGTH: 23
<212> TYPE: DNA
<213> ORGANISM: Artificial Sequence
<220> FEATURE:
<223> OTHER INFORMATION: Oligonucleotide
<220> FEATURE:
<221> NAME/KEY: misc_binding
<222> LOCATION: (1)..(23)

<400> SEQUENCE: 26
tgtcttttca ctggagttgt ccc                                          23

<210> SEQ ID NO 27
<211> LENGTH: 21
<212> TYPE: DNA
<213> ORGANISM: Artificial Sequence
<220> FEATURE:
<223> OTHER INFORMATION: Oligonucleotide
<220> FEATURE:
<221> NAME/KEY: misc_binding
<222> LOCATION: (1)..(21)

<400> SEQUENCE: 27
ttctccttta ctcatttttt c                                            21

<210> SEQ ID NO 28
<211> LENGTH: 24
<212> TYPE: DNA
<213> ORGANISM: Artificial Sequence
```

```
<220> FEATURE:
<223> OTHER INFORMATION: Primer
<220> FEATURE:
<221> NAME/KEY: prim_transcript
<222> LOCATION: (1)..(24)
<223> OTHER INFORMATION: Primer for inverse PCR

<400> SEQUENCE: 28
tgcacacatg gcatggatga gctc                                          24

<210> SEQ ID NO 29
<211> LENGTH: 21
<212> TYPE: DNA
<213> ORGANISM: Artificial Sequence
<220> FEATURE:
<223> OTHER INFORMATION: Primer
<220> FEATURE:
<221> NAME/KEY: prim_transcript
<222> LOCATION: (1)..(21)
<223> OTHER INFORMATION: Primer for inverse PCR

<400> SEQUENCE: 29
cccagcagca gttacaaact c                                             21

<210> SEQ ID NO 30
<211> LENGTH: 33
<212> TYPE: DNA
<213> ORGANISM: Artificial Sequence
<220> FEATURE:
<223> OTHER INFORMATION: Primer
<220> FEATURE:
<221> NAME/KEY: prim_transcript
<222> LOCATION: (1)..(33)
<223> OTHER INFORMATION: Primer for inverse PCR

<400> SEQUENCE: 30
cagcgccgtt gtgagctcta caaataatga att                                33

<210> SEQ ID NO 31
<211> LENGTH: 21
<212> TYPE: DNA
<213> ORGANISM: Artificial Sequence
<220> FEATURE:
<223> OTHER INFORMATION: Primer
<220> FEATURE:
<221> NAME/KEY: prim_transcript
<222> LOCATION: (1)..(21)
<223> OTHER INFORMATION: Primer for inverse PCR

<400> SEQUENCE: 31
tgtaatccca gcagcagtta c                                             21

<210> SEQ ID NO 32
<211> LENGTH: 21
<212> TYPE: DNA
<213> ORGANISM: Artificial Sequence
<220> FEATURE:
<223> OTHER INFORMATION: Primer
<220> FEATURE:
<221> NAME/KEY: prim_transcript
<222> LOCATION: (1)..(21)
<223> OTHER INFORMATION: Primer for inverse PCR

<400> SEQUENCE: 32
acatgtgagc tctacaaata a                                             21

<210> SEQ ID NO 33
<211> LENGTH: 18
<212> TYPE: DNA
```

```
<213> ORGANISM: Artificial Sequence
<220> FEATURE:
<223> OTHER INFORMATION: Primer
<220> FEATURE:
<221> NAME/KEY: prim_transcript
<222> LOCATION: (1)..(18)

<400> SEQUENCE: 33
acggccctgt gtaatccc                                                 18

<210> SEQ ID NO 34
<211> LENGTH: 21
<212> TYPE: DNA
<213> ORGANISM: Artificial Sequence
<220> FEATURE:
<223> OTHER INFORMATION: Primer
<220> FEATURE:
<221> NAME/KEY: prim_transcript
<222> LOCATION: (1)..(21)
<223> OTHER INFORMATION: Primer for inverse PCR

<400> SEQUENCE: 34
ggaacatgtg agctctacaa a                                             21
```

ENDOCYTOSIS ENHANCER FOR DRUG DELIVERY SYSTEM

TECHNICAL FIELD

The present invention relates to an endocytosis enhancing preparation for drug delivery system. Specifically, it relates to the endocytosis enhancing preparation for drug delivery system including carbosilane dendrimer and fluorescent proteins.

BACKGROUND ART

It is generally known that the dendrimer having silole (hereinbelow, it is referred to as a "carbosilane dendrimer" in the present specification) emits fluorescence, when they form a micelle. The carbosilane dendrimer supporting hydrophilic compound such as a sugar emits by AIE (aggregation-induced emission). However, the micelle composed of the carbosilane dendrimers has environmental-depending emission, and intensity is low. Here, AIE is the phenomenon caused by irradiating light having particular wave-length to mutually aggregated fluorescent compounds to cause high fluorescent emission (see the non-patent document 1, hereinbelow it is referred to as the "prior art 1").

Also, it is known that the carbosilane dendrimers supporting the sugars (herein below, it is sometimes referred to as "SCD") form solvent-driven micelle in an organic solvent, although they do not from the micelle in the aqueous solution (see FIGS. 1 & 2).

In contrast, the carbosilane dendrimer supporting protein (it is sometimes referred to as "PCD" or "aggregating molecule".) form a liposome (which is sometimes referred to as a "vesicle") wherein the protein faces to outside (See FIG. 3). The vesicle or micelle formed as mentioned above is sometimes referred to as a "PCD micelle".

Then, it is known that strong fluorescence is generated by AIE, when the protein is supported onto the carbosilane dendrimer (See the patent document 1, which is referred to as the "prior art 2" hereinbelow. See FIG. 3). When the protein being supported on the dendrimer is substituted to the fluorescent protein, stronger fluorescence is observed.

At present, a variety of fluorescent protein that emits a variety of fluorescence is used for labelling in a living body. Early stage by using them as the fluorescent label, such fluorescent protein generates undesirable aggregation, and it often causes trouble to desirable observation. For example, when the fluorescent protein which requires tetramer form to emit fluorescence such as dsRED is added to actin, four actin subunits aggregate by using the functions of dsRED, and it prevents the desirable observation in a cell.

Therefore, in order to prevent the aggregation of the fluorescent protein, some contrive has been conducted such that the fluorescent protein which is existed naturally as the tetramer form is modified to emit the fluorescence even if it becomes a monomer, or generate a mutation to prevent the association even if they become dimer. As a result, the commercially available GFP is the dimer form or monomer form (see, the non-patent document 2).

On the other hand, when the pharmaceutical preparation is administered, response rate and occurrence of side effects are affected by the amount of the active ingredients delivered to the target site, although it varies on the disease to be treated and the properties of the pharmaceutical preparation. Therefore, as a means for delivering the pharmaceutical preparation to the target site, a variety of drug delivery system (DDS: Drug Delivery System) is actively developed.

As a carrier for DDS, it is known as, for example, liposomes, synthetic polymer particles, dendrimers and the like. In order to prevent and/or treat the disease caused by virus infection or bacterial infection, for example, the carrier utilized the dendrimer is developed (see, the patent document No. 2).

PRIOR ART DOCUMENTS

Patent Documents

[Patent Document 1] JP 5629888 B
[Patent Document 2] WO2016/084979

Non-Patent Documents

[Non-patent Document 1] Chem Commun (Camb). 2009 Aug. 7; (29):4332-53. doi: 101039/b904665h. Epub 2009 May 13
[Non-patent Document 2] Protein Data Bank Japan, 174: GFP-like Proteins.

SUMMARY OF THE INVENTION

Problem to be Solved by the Invention

More than 90% of the administrated pharmaceutical preparations is not metabolizes and excreted as anabolites. Therefore, a certain administration amount of the pharmaceutical preparation is required. Also, when the pharmaceutical preparation contains biopolymers such as ab antibody, peptide and the like so-called Next-generation pharmaceutical preparations as the active ingredient, it is inactivated before it is delivered to the target sites. Therefore, they should be included in the CD micelle (see, FIG. 4(A) and FIG. 4(B)).

On the other hand, in order to show the pharmacological effects from the pharmaceutical preparation included in the micelle, the incorporation thereof into the cell is necessary. Then, most of such an incorporation of the preparation included in the micelle is carried out by endocytosis. Therefore, it is necessary for enhancing the endocytosis.

Also, in order to enhance the endocytosis, several kinds of enhancers are necessary. However, such enhancers should have biocompatibility by itself, and does not break the properties or characteristics are not known. Therefore, there are strong social needs for the endocytosis enhancer.

Enhance of the endocytosis leads to decrease the amount of the pharmaceutical preparation to be administrated. Since this enables to decrease the excretion amount of the anabolite, it leads to decrease environmental burden caused by releasing chemical substances to the environment. Furthermore, depending on the pharmaceutical preparations, there is the possibility to decrease the side effects.

Therefore, there are strong social needs to the enhancer which decrease the administration amount of the pharmaceutical preparation, to confirm the delivery to the target tissue, and release thereof, and to be used for estimating the effective administration amount of the preparation.

Means for Solving the Problem

The inventors of the present invention firstly found following issued: mixing of the carbosilane dendrimer containing silole and the labeled protein (for example, green fluorescent protein, it is collectively referred to as GFP including the fluorescent protein which emits the fluorescence other than green) gives an aggregatable molecule, which is the carbosilane dendrimer presenting GFP, either in the aqueous solvent or the mixed solvents composed of the aqueous solvent and the organic one; the conjugate composed of GFP by itself; and the conjugate properties drive to generate CD micelle.

After that, the present inventors further studied, they found that GFP conjugate itself generated during formation of the aggregable molecules remarkably enhances the endocytosis of the CD micelle into the cell. Also, they found that difficulty of the GFP conjugate formation is varied, and then completed the present invention.

The present invention has been completed under the above-mentioned conditions. The purpose of the present invention is to provide an endocytosis enhancing preparation containing carbosilane dendrimers and fluorescent proteins for drug delivery system.

The present invention comprises following aspects.

In an aspect of the present invention is the endocytosis enhancing preparation being composed of conjugate of the fluorescent proteins. Here, the fluorescent protein is preferable that it is any one of the protein selected from the group consisting of white fluorescent protein, red fluorescent protein, yellow fluorescent protein, blue fluorescent protein, and green fluorescent protein.

Also, the conjugate is preferably formed by aggregating 2 to 10 molecules of the fluorescent protein. The fluorescent protein is preferable that it further comprises a target recognition sequence, and it also enhances the conjugate itself into the cell. The target recognition sequence is preferable that it is the sequence which enables to regulate the formation of the conjugate of the fluorescent protein.

The target recognition sequence is preferably composed of a functional peptide, and the functional peptide is preferably a substance that specifically bounds to any one of the target protein selected from the group consisting of a surface antigen, a receptor, a gate, a transporter, and a channel, which are expressed on the target tissue. The target recognition sequence preferably functions so as to regulate the formation of the conjugate of the fluorescent proteins. The target sequence recognition sequence has preferably a sequence selected from the group consisting of the SEQ ID NOS: 1 to 3 in the sequence listing.

DMPGTVLPGG (SEQ ID NO: 1 in the sequence listing)
VPTDTDYSGG (SEQ ID NO: 2 in the sequence listing)
DMPGTVLPGG GGGSEGEWQ QQQHQWAKQE (SEQ ID NO: 3 in the

SEQUENCE LISTING

Also, the endocytosis enhancing preparation is preferable to enhance the incorporation of the micelle being composed of the aggregable molecule having the back bone structure shown in the following formula (I) through the endocytosis. In the formula, n means an integer from 1 to 6.

[Chemical formula 1.]

(I)

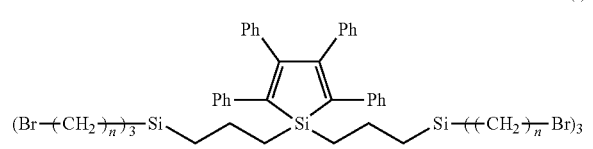

The aggregable molecule shown in the formula (I) is preferably a compound having the bone structure shown in the following formula (II).

[Chemical formula 2.]

(II)

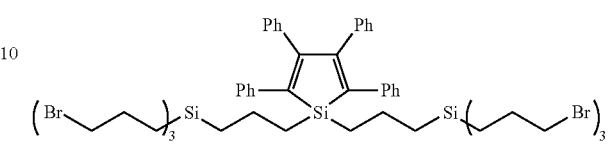

The aggregable molecule is preferably any one selected from the group consisting of the compound shown in the following formula (III) to (VI). In the formula, GFP shows the fluorescent protein.

[Chemical Formula 3.]

(III)

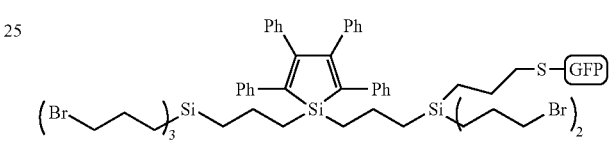

[Chemical Formula 4.]

(IV)

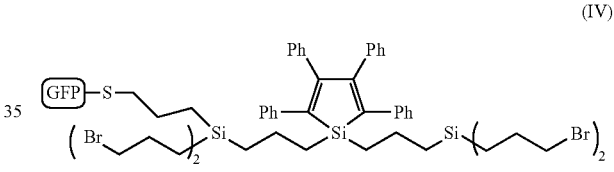

[Chemical Formula 5.]

(V)

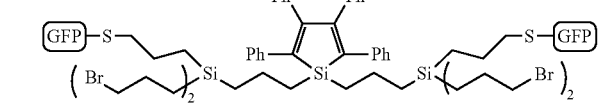

[Chemical Formula 6.]

(VI)

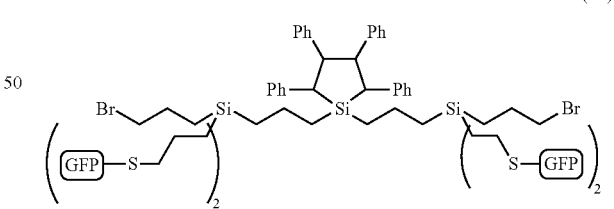

The endocytosis enhancing preparation of the present invention preferably enhances the endocytosis of the micelles being composed of the aggregable molecules. Here, the micelle is formed so as to have the protein on the outside in the aqueous medium, and it has a diameter from 50 to 500 nm, emitting the fluorescence derived from FRET.

Also, the micelle preferably include any one selected from the group consisting of the molecule having not larger than the molecular weight of 200,000, a nucleic acid, and a lipophilic molecule. The molecule having not larger than the molecular weight of 200,000 is preferably selected from the group consisting of immunoglobulin G, lectin, and peptide hormone.

Advantageous Effect of the Invention

According to the present invention, it is provided that the endocytosis enhancing preparation which enhances the endocytosis of the micelle being composed of the aggregable molecule. Here, the endocytosis enhancing preparation has high fluorescent intensity, which is detectable and observable in the living body.

BRIEF DESCRIPTION OF DRAWINGS

FIG. 4(A) and FIG. 4(B) show the schematic figure of a biopolymer which is encapsulated in the aggregable molecules FIG. 4(A) and that showing the protein-driven aggregation FIG. 4(B).

FIG. 6(A) shows the fraction containing small amount of the fluorescent protein conjugate, FIG. 6(B) shows that containing the medium amount, and FIG. 6(C) shows that containing the high amount, respectively.

In FIG. 7(B), TPS shows the particle without encapsulated molecules, and GDS shows that with the encapsulated particles.

FIG. 9(A) shows the result of the fluorescent detection, and FIG. 9(B) shows that of CBB (Coomassie Brilliant Blue) staining.

FIG. 10(A), FIG. 10(B), FIG. 10(C) and FIG. 10(D) show the result of the gel electrophoresis for studying the obtained conjugate formed. Both of FIG. 10(A) and FIG. 10(B) show the results of FITC staining (laser 475 and PMT500). Also, both of FIG. 10(C) and FIG. 10(D) show the decolorized results after CBB staining (No. 1).

FIG. 11(A), FIG. 11(B), FIG. 11(C) and FIG. 11(D) show the result of the gel electrophoresis for studying the obtained conjugate formed. Both of FIG. 11(A) and FIG. 11(B) show the results of FITC staining (laser 475 and PMT500). Also, both of FIG. 11(C) and FIG. 11(D) show the decolorized results after CBB staining (No. 2).

FIG. 15 is the graph showing the result of the change for the micelle incorporation into the cell depending on the target peptides contained in the conjugate being used (No. 4).

FIG. 16(A) and FIG. 16(B) show the micelle size distribution when they were formed in 50 mM Tris-HCl buffer (pH 8.0). FIG. 16(A) is the micelle faction solution, and FIG. 16(B) is the unreacted micelle solution.

FIG. 17(A) and FIG. 17(B) show the micelle size distribution when they were formed in 50 mM HEPES buffer (pH 7.6). FIG. 17(A) is the micelle faction solution, and FIG. 17(B) is the unreacted micelle solution.

FIG. 18(A) and FIG. 18(B) show the micelle size distribution when they were formed in 50 mM sodium citrate buffer (pH 7.6). FIG. 18(A) is the micelle faction solution, and FIG. 18(B) is the unreacted micelle solution.

FIG. 19(A) and FIG. 19(B) show the micelle size distribution when they were formed in 50 mM carbonate-sodium bicarbonate buffer (pH 7.6). FIG. 19(A) is the micelle faction solution, and FIG. 19(B) is the unreacted micelle solution.

FIG. 21(A) shows that immediately after the preparation, and FIG. 21(B) shows 1 day later from the preparation, respectively.

FIG. 22(A) shows that immediately after the preparation, and FIG. 22(B) shows 1 day later from the preparation, respectively.

FIG. 23(A) shows that immediately after the preparation, and FIG. 23(B) shows 1 day later from the preparation, respectively.

MODE FOR CARRYING OUT THE INVENTION

Figure 1:
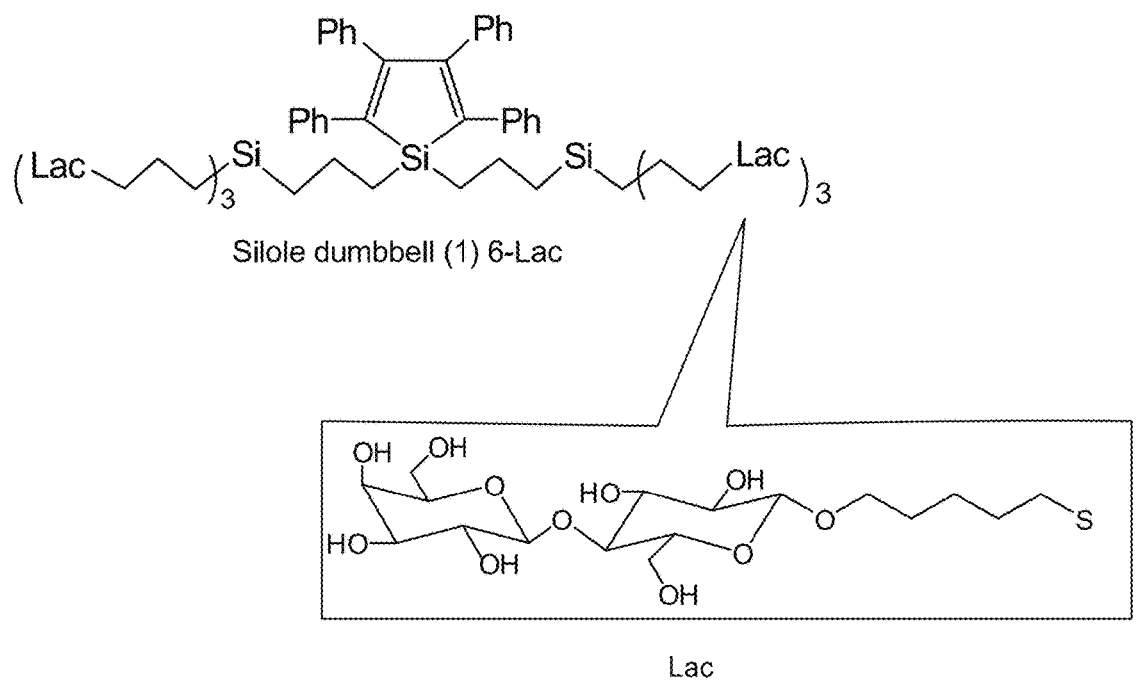
FIG. 1(A) and FIG. 1(B) schematically shows a basic form of a silole dumbbell (1) 6-Lac FIG. 1(A) and micelle formation FIG. 1(B).
Figure 1:
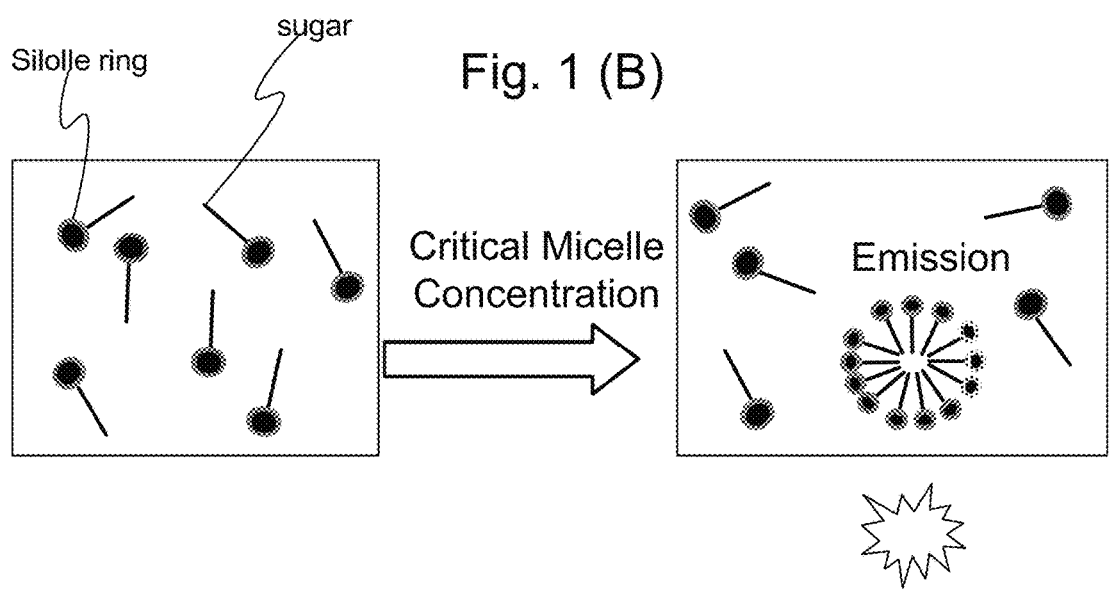
Figure 2:
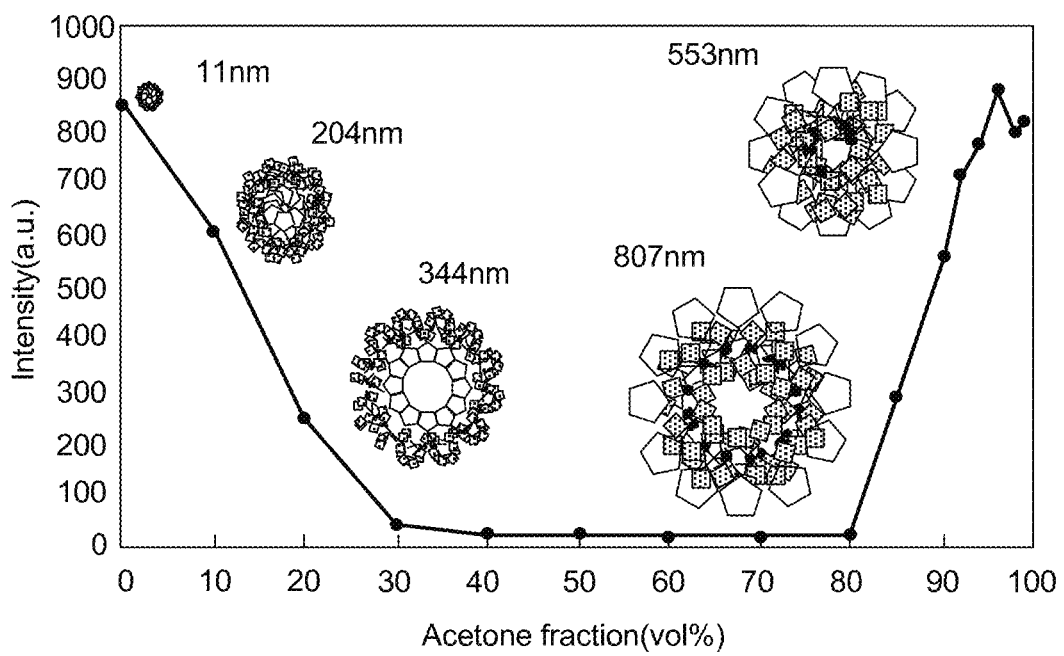
FIG. 2(A) and FIG. 2(B) show the relationship between an intensity f fluorescent and diameter size of the micelle composed of the silole dumbbell (1) 6-Lac in acetone/water mixed solution FIG. 2(A) and changing of fluorescent wavelength thereof FIG. 2(B).
Figure 2:
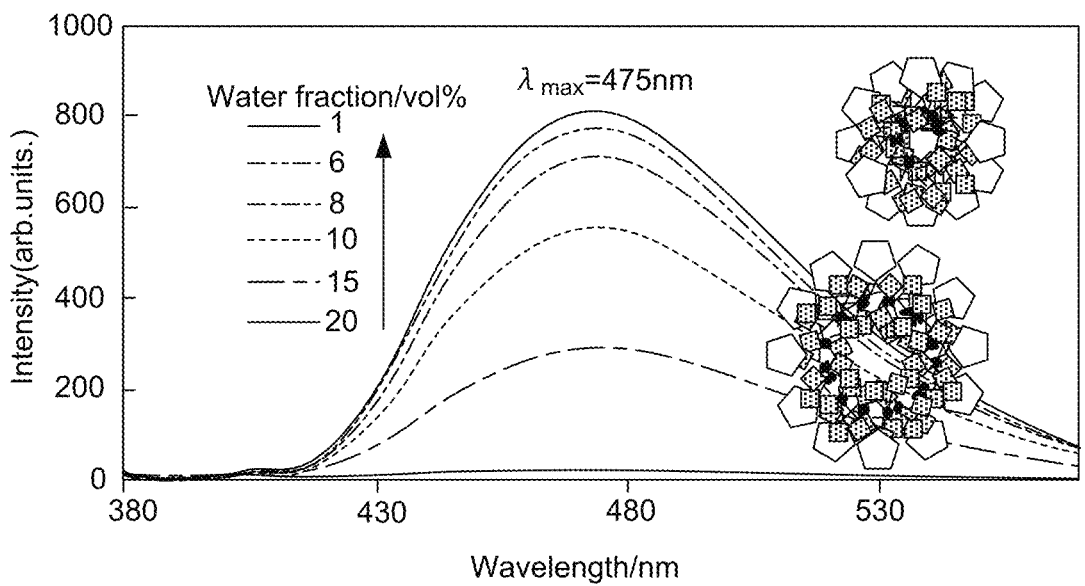
Figure 3:
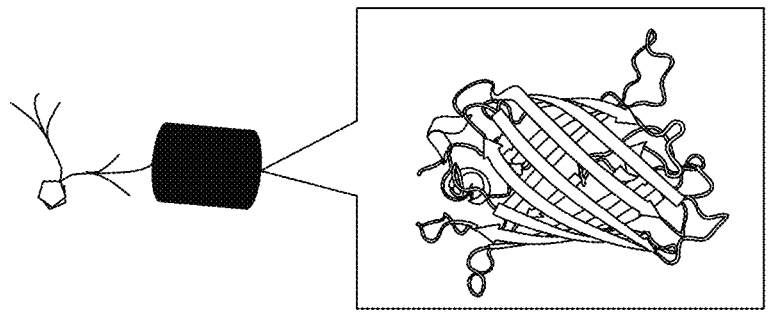
FIG. 3(A), FIG. 3(B) and FIG. 3(C) are schematic figures showing the carbosilane dendrimer bound to GFP FIG. 3(A). In the figure, the fluorescent protein is shown as black solid rectangular. Its detail structure is schematically shown in the blowoff. Pre-aggregation state of the carbosilane dendrimer presenting GFP (aggregable molecules) is shown in FIG. 3(B), and after aggregation thereof is shown in FIG. 3(C).
Figure 3:
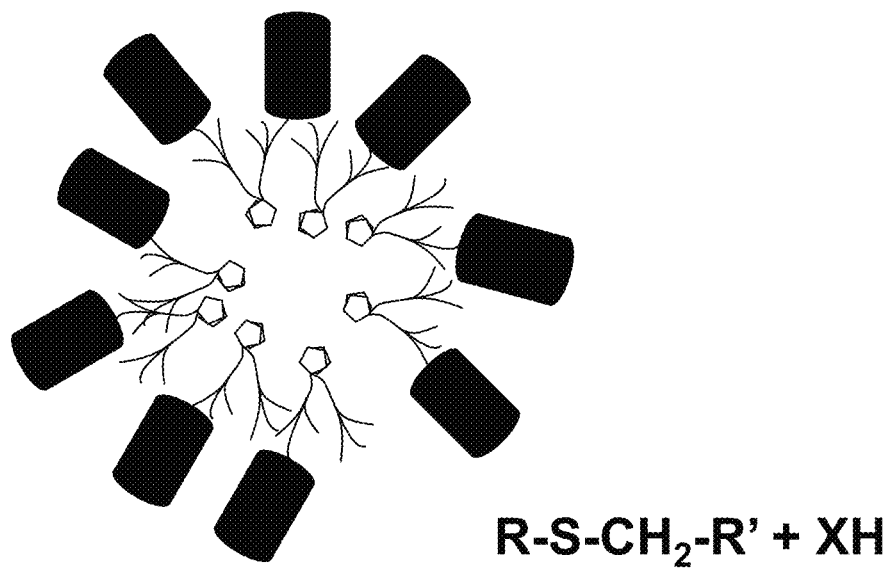
Figure 3:
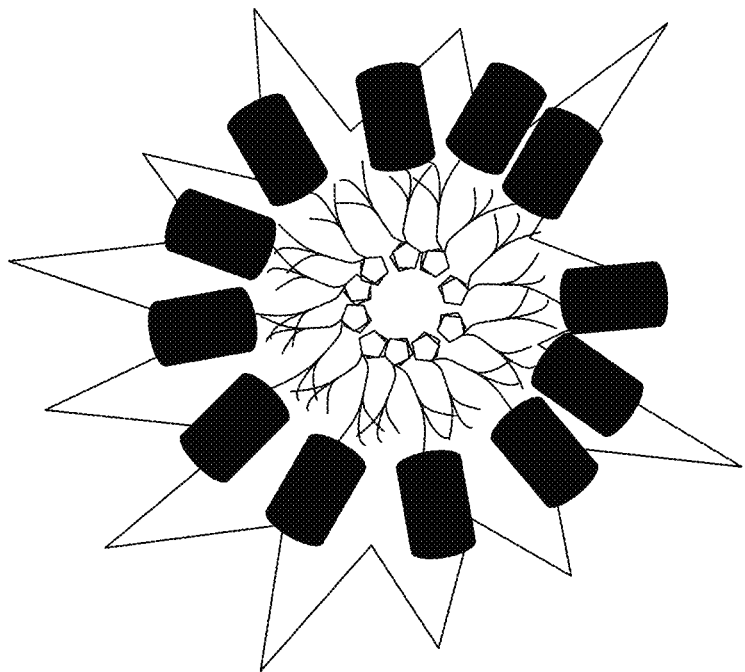
Figure 4:
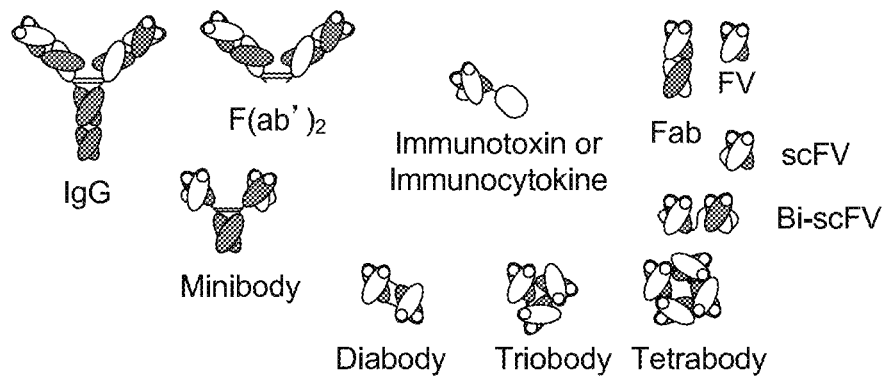
In FIG. 4 (B), as the same as FIG. 3(C), GFP is schematically in the blowoff, and also immunoglobulin G is schematically shown.
Figure 4:
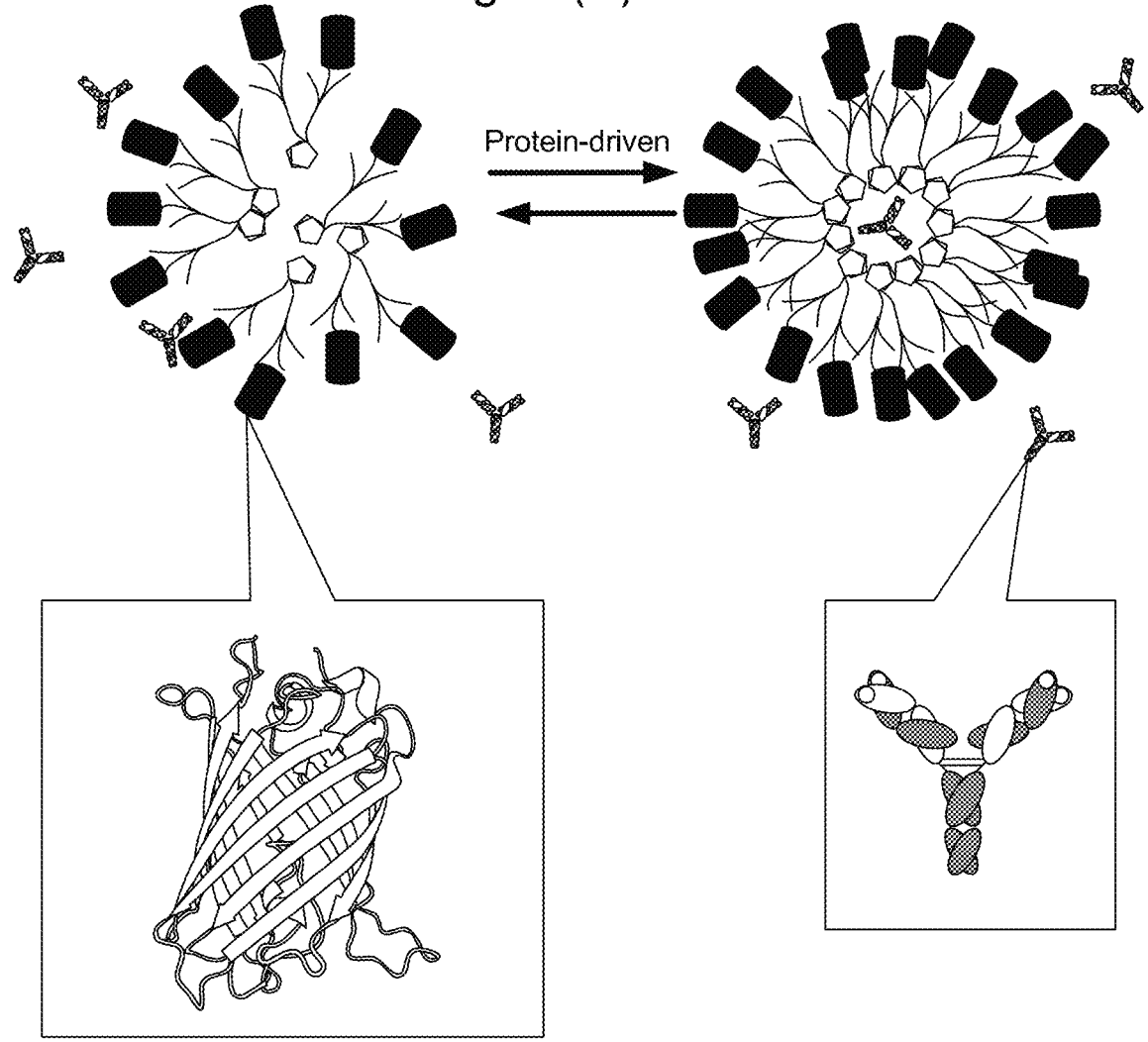

Herein below, the present invention is explained in detail. The present invention is the endocytosis enhancing preparation comprising the conjugate formed by the fluorescent protein as described above. The fluorescent protein composes the endocytosis enhancing preparation of the present invention is particularly limited. However, it is preferably a fluorescent protein comprising green fluorescent protein or its derivatives. The reasons are as follows: GFP emits strong fluorescence, when they form the conjugate; the formed conjugate show the endocytosis effect which incorporates the substance close to the cell surface; and the conjugate itself is so as to be incorporated into the cell in a large amount.

As GFP being employed in the present invention, there are mentioned such as white fluorescent protein, red fluorescent protein, yellow fluorescent protein, blue fluorescent protein, green fluorescent protein and the like, and it is particularly limited as long as they form the conjugate. For example, there are mentioned such as GFP shown in the SEQ ID NO: 7 or that shown in the SEQ ID NO: 8 in the sequence listing; BFP (blue fluorescent protein) shown in the SEQ ID NO: 9 in the sequence listing; TEP shown in the SEQ ID NO:10 in the sequence listing; commercially available CFP or RFP provided by Clontech and the like.

Also, other than these, the fluorescent protein derived from Discosoma shown in the SEQ ID NO: 5 in the sequence listing may be preferably used. Furthermore, it is assumed that Azami-green provided from MBL and other derivatives thereof may be preferably used due to their structural properties. Since such fluorescent protein has broader wavelength range for the detection and has high intensity, they are suitably employed. Here, the blue fluorescent protein contains these emit blue or cyan fluorescence.

As described above, GFP used in the present invention preferably has the property to form the conjugate of dimer or more than that. Also, it is preferable to use GFP shown in the SEQ ID NO: 7 in the sequence listing, because it has strong fluorescence and easily forms the conjugate.

Such GFP may be produced by using the known method (see, for example, Biochim. Biophys. Acta 1679 (2004) 222-229; Biochem. Biophys. Res. Commun. 330 (2005) 454-460 and the like), or those provided by the manufacturer who conduct the production of GFP by commissioning may be used.

Also, as the concrete degree of conjugation, the conjugate of 2 to 10 molecules of GFP as mentioned above is preferable, because it has high endocytosis effect. The conjugate of tetramer or more is more preferable; because the endocytosis enhancing preparation of the present invention has higher degree of conjugation, it has higher endocytosis enhancing effect, and also the conjugate enhances the incorporation of itself into the cell.

It is preferable that the fluorescent protein further comprises the target recognition sequence, because it promotes the conjugate of GFP. As the target recognition sequence, there are mentioned such as the substance which specifically bounds to the target protein selected from the group consisting of a surface antigen, a receptor, a gate, a transporter, and a channel expressed on a variety of tissues.

More concretely, as the functional peptide, there are mentioned such as any one of the peptide selected from the group consisting of those shown in the SEQ ID NOS: 1 to 3 in the sequence listing; because the addition of the peptide enables to control the formation of the conjugate of GFP as mentioned above.

```
          (SEQ ID NO: 1 in the sequence listing)
     DMPGTVLPGG (SEQ ID NO: 2 in the sequence listing)
     VPTDTDYSGG (SEQ ID NO: 3 in the sequence listing)
     DMPGTVLPGG GGGSEGEWQ QQQHQWAKQE
```

As GFP having the peptide, there are mentioned such as that having the sequence selected from the group consisting of those of SEQ ID NOS: 4 to 6 in the sequence listing.

```
          (SEQ ID NO: 4 in the sequence listing)
MASMTGGQQMGR DMPGTVLPGG MSKGEELFTG VVPILVELDG

DVNGHKFSVS GEGEGDATYG KLTLKFISTT GKLPVPWPTL

VTTLTYGVQC FSRYPDHMKR HDFFKSAMPE GYVQERTISF

KDDGNYKTRA EVKFEGDTLV NRIELKGIDF KEDGNILGHK

LEYNYNSHNV YITADKQRNG IKANFKTRHN IEDGSVQLAD

HYQQNTPIGD GPVLLPDNHY LSTQSALLKD PNEKRDHMVL

LEFVTAAGSGIT DEVDGT ELYK GG HHHHHH (SEQ ID NO: 5 in the sequence listing)
MASMTGGQQMGR VPTDTDYSGG MSKGEELFTG VVPILVELDG

DVNGHKFSVS GEGEGDATYG KLTLKFISTT GKLPVPWPTL

VTTLTYGVQC FSRYPDHMKR HDFFKSAMPE GYVQERTISF

NDDGNYKTRA EVKFEGDTLV NRIELKGIDF KEDGNILGHK

LEYNYNSHNV YITADKQRNG IKANFKTRHN IEDGSVQLAD

HYQQNTPIGD GPVLLPDNHY LSTQSALLKD PNDKRDHMVL

LEFVTAAGSGIT DEVDGT ELYK GG HHHHHH (SEQ ID NO: 6 in the sequence listing)
MASMTGGQQMGR DMPGTVLPGG GGGSEGEWQQQQHQWAKQE

MSKGEELFTG VVPILVELDG DVNGHKFSVS GEGEGDATYG

KLTLKFISTT GKLPVPWPTL VTTLTYGVQC FSRYPDHMKR

HDFFKSAMPE GYVQERTISF KDDGNYKTRA EVKFEGDTLV

NRIELKGIDF KEDGNILGHK LEYNYNSHNV YITADKQRNG

IKANFKTRHN IEDGSVQLAD HYQQNTPIGD GPVLLPDNHY

LSTQSALLKD PNEKRDHMVL LEFVTAAGSGIT DEVDGTC

ELYK GG HHHHHH
```

Figure 5:
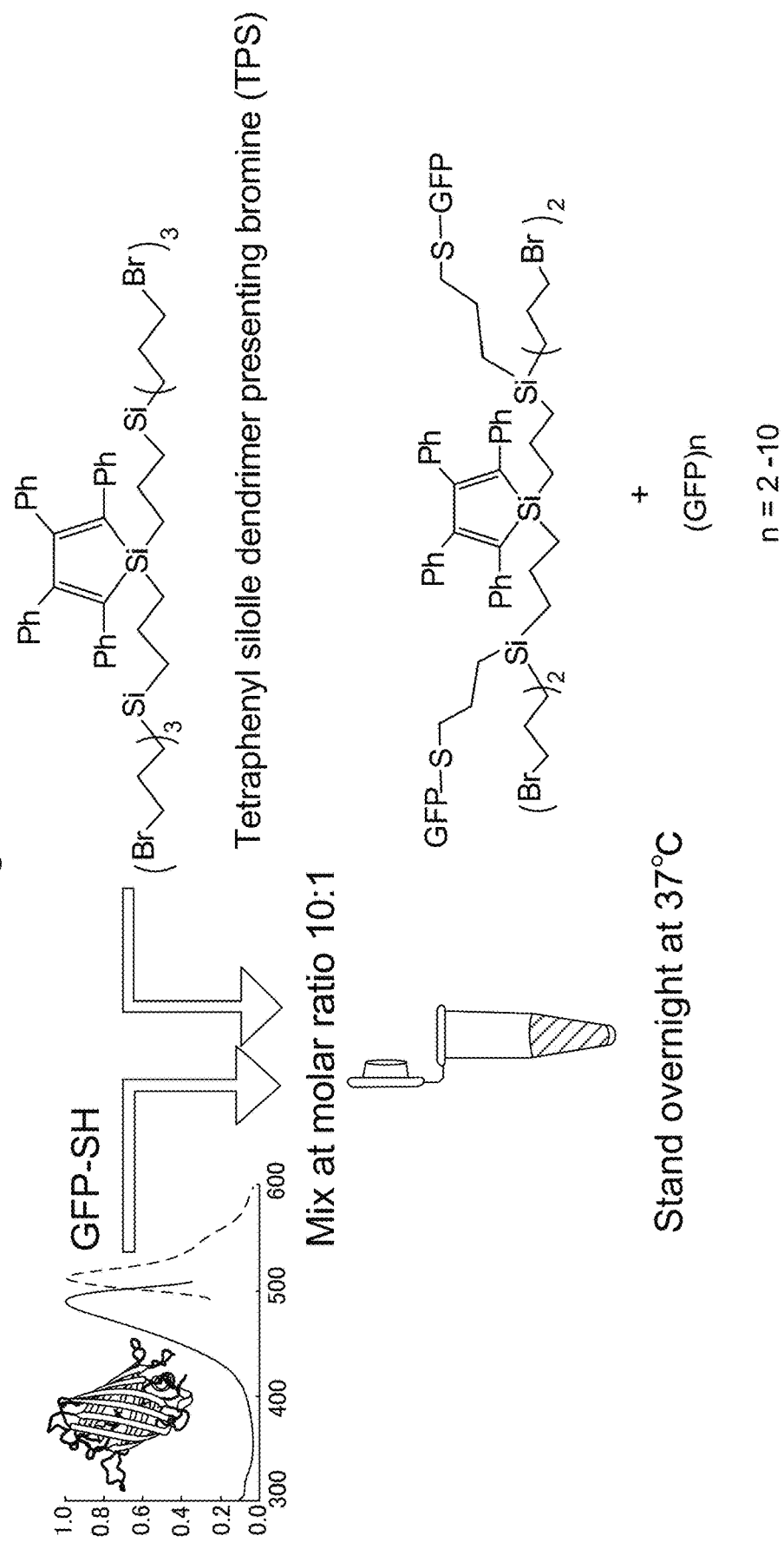
FIG. 5 is the schematically figure showing process for preparing the aggregable molecule of the present invention and the endocytosis enhancing agent of the present invention, and changing of the fluorescent wavelength depending thereof.

The endocytosis enhancing preparation of the present invention is obtained by dissolving GFP in the aqueous solution such physiological saline, which does not denature proteins to associate them. Alternatively, it is produced simultaneously through the reaction as shown in FIG. 5, wherein the compound having the backbone shown in the formula (II) and GFP are bound.

[Chemical formula 7.]

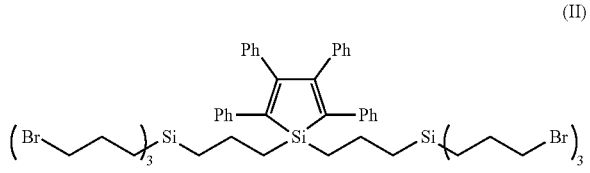

(II)

For example, the reaction is conducted in the suitable medium, aqueous solution such as phosphate buffered saline (PBS), saline, Tris-HCl buffer, HEPES buffer, sodium citrate buffer, and carbonate-sodium bicarbonate buffer. The reaction condition varies on the depending on the protein to be used. However, the reaction temperature is as long as lower than that of the protein denaturation; it may be for example, 0 to 50° C., preferably 30° C. to 45° C., more preferably around 37° C. When GFP is used, the reaction property is improved up to 42° C. on temperature dependently.

Also, by using the buffer as mentioned above used for the micelle formation, and for example, 1×PBS for the formed micelle separation, the micelle fraction wherein the buffer inside of the micelle and that outside of the micelle are different is obtained. By this, the micelle suitable for dissolving the drug included in the micelle is manufactured.

It is preferable to treat GFP preliminary with a reducing agent such as DTT and the like to keep—SH group in non-oxidized state. Mixing ratio of the fluorescent protein and the dendrimer (molar ratio) may be that the protein equals 1 and the dendrimer is, for example, in the range of 1 to 20; preferably 1:5 to 1:15; more preferably 1:around 10. Note that the ratio varies depending on the concentrations.

Also, the reaction period varies depending on the reaction temperature. However, it is, for example, 1 to 24 hours; preferably it is 10 to 19 hours; more preferably, it is 15 to 18 hours. Due to set the reaction period in the range, GFP having thiol group used is bound to the silole dendrimer (hereinbelow, it is sometimes referred to as "GFP-TPS") and the conjugate of GFP, the endocytosis enhancing preparation, is formed. In the reaction, at least 1 molecule of GFP is combined into the silole dendrimer.

After that, according to the conventional method for forming them, the fraction containing GFP-TPS is obtained. Here, the fraction containing GFP-TPS comprises certain amount of the GFP conjugate. The amount of the GFP conjugate varies depending on the presence or absence of the target peptide as well as the types thereof. They are classified into three such as the fraction contains small amount of GFP conjugate (the micelle A); that contains medium amount of them (the micelle B); and that contains large amount of them (the micelle C).

The content amount of GFP in the fraction which containing the micelle may be measured by using the excitation wavelength 488 nm and detection wavelength 510 nm. Also, GFP-TPS may be measured by using the excitation wavelength 370 nm and detection wavelength 510 nm.

When the micelle collapses, FRET of the micelle disappears. Therefore, the status of the carrier (the micelle) in the living body may monitored by changing FRET as an index. Furthermore, the monitoring enables to monitor the status of the micelle such that they are existing in the aqueous medium or incorporate in the cell, or they collapsed or not. On the other hand, since FRET of the conjugate remains, it is possible to monitor such that the conjugate is present, for example, in the aqueous solution or on the cell membrane and the like.

According the present invention, the endocytosis enhancing preparation for the drug delivery system is provided.

EXAMPLES

The following examples are merely illustrative and do not limit the scope of the invention.

(Example 1) Preparation of the Endocytosis Enhancing Agent of the Present Invention In the present embodiment, a protein for preparing the endocytosis enhancing agent, and GFP shown in SEQ ID NO: 7 of the sequence listing as the protein for preparing GFP-TPS are used. As the dendrimer, silole dendrimer is used. Here, the used GFP is prepared by using the method which has been reported by the inventors (see, Biochim. Biophys. Acta 1679 (2004) 222-229; Biochem. Biophys. Res. Commun. 330 (2005) 454-460); in the used GFP, Serine at the position 251 in C region of the GFP shown in SEQ ID NO: 7 in the sequence listing was replaced to Cysteine, and originally existed cysteines, at the positions of 48 and 70, were respectively replaced to Ser and Val.

(1) Preparation of the Aggregatable Molecule for DDS

In the example, the compound having the following chemical formula (I) as the dendrimer having halogen group and GFP (green fluorescent protein) (SEQ ID NO: 7) was used as the protein having thiol group.

[Chemical formula 8.]

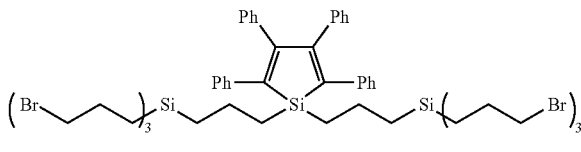

(II)

At first, DTT was added to GFP solution of 20 µM concentration (in PBS) at 1 mM as a final concentration, and the GFP solution was treated for 10 minutes at room temperature to reduce cysteines on the surface of GFP. Ten µL of 200 µM of silole dendrimer shown the formula (VI) solution (in DMSO solution) was added to 400 to 450 µL of 20 µM GFP solution (in PBS) to have the final concentration of 10-fold molar equivalent, and then mixed with vortex mixer.

After vortex, the solution was stood at 37° C. for overnight incubation to bind GFP and the silole dendrimer, and subsequently to form the micelles. The incubation time for this experiment was about 16 to 18 hours. The properties of the micelle particles in the solution were measured by using dynamic light scattering method (DLS; Dynamic light scattering). The result was shown in Table 1.

TABLE 1

Average particle diameters of raw materials and products in PBS measured 5 times at 25° C. [nm]

| | Zeta Average | Particle diameter peak by scattering intensity | Particle diameter peak by number |
|---|---|---|---|
| 20 μM GFP only | 860.7 | 838.8 | 4.682 |
| 50 μM Silole only | 894.5 | 664.6 | 649.3 |
| 20 μM GFP-Silole only | 210.3 | 256.8 | 147.7 |

Figure 7:
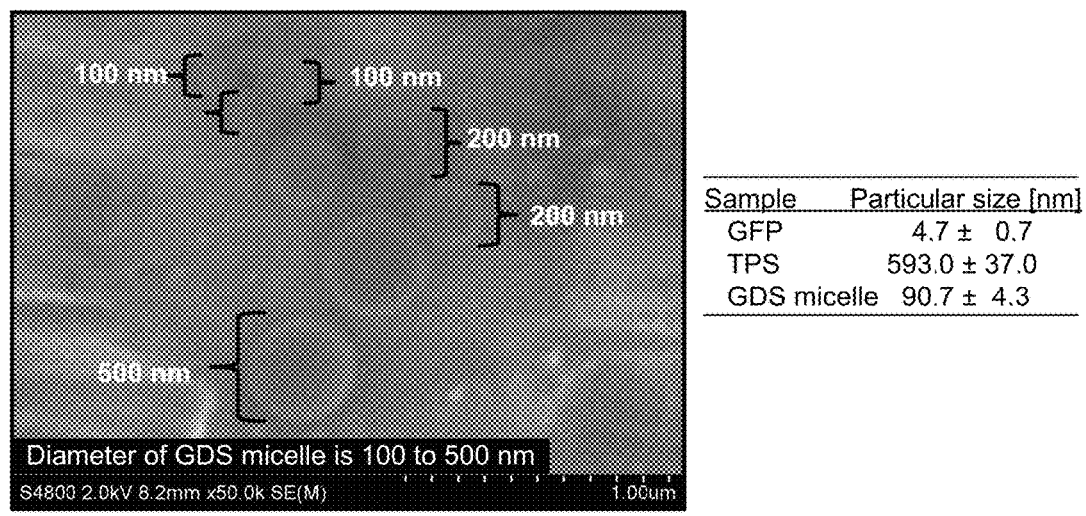
FIG. 7(A), FIG. 7(B) and FIG. 7(C) show the scanning type electron microscope showing the micelle particle shapes formed by the aggregable molecule of the present invention FIG. 7(A); and the graph showing both of the particle size distribution and the change of the emission properties (respectively FIG. 7(B) and FIG. 7(C)).
Figure 7:
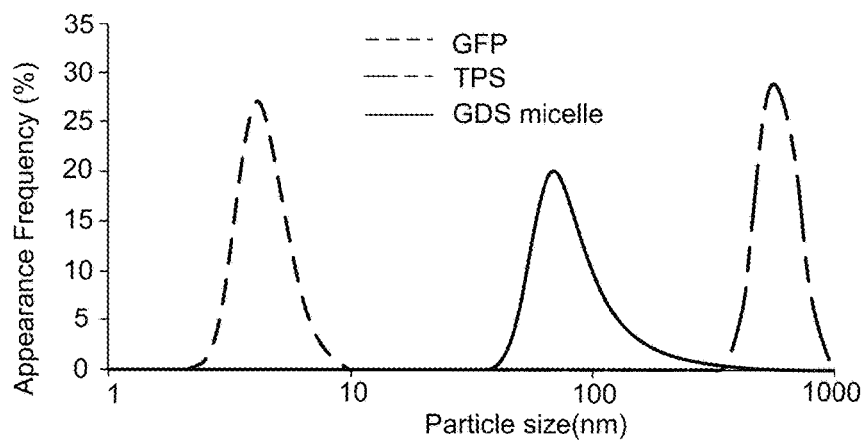
Figure 7:
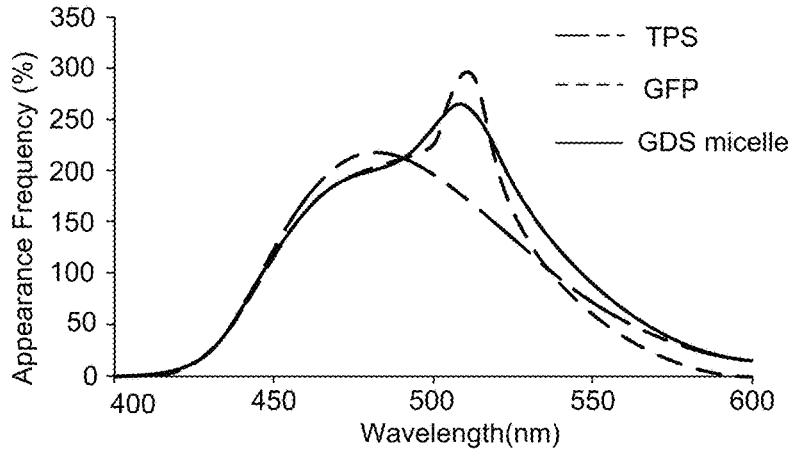

Also, the particle size in the reaction mixture was measured at 25° C. by using ZETASIZER NANO-S (manufactured by Malvern Instrument Ltd.) with a laser beam wavelength of 532 nm. The result was shown in FIG. 7(A), FIG. 7(B) and FIG. 7(C). FIG. 7(A) shows the result that GFP only was incubated and the particle sizes of the obtained products were measured. FIG. 7(B) shows the result that only the silole dendrimer was incubated and the particle size of the obtained product was measured.

FIG. 7(C) shows the result that GFP and the silole dendrimer shown in formula (VI) were mixed and incubated, and the particle sizes of the obtained products were measured. The horizontal axis shows the particle sizes of the obtained products, and the vertical axis shows the percentage of the whole products with the sizes shown on the horizontal axis.

When GFP and the silole dendrimer were incubated (in Table 1, it is shown as "GFP-Silole only"), the particle size of the micelle obtained was about 150 nm. In contrast, the particle size observed when GFP only was incubated was about 4 nm, and the particle size observed when silole dendrimer only was incubated was about 650 nm.

Figure 8:
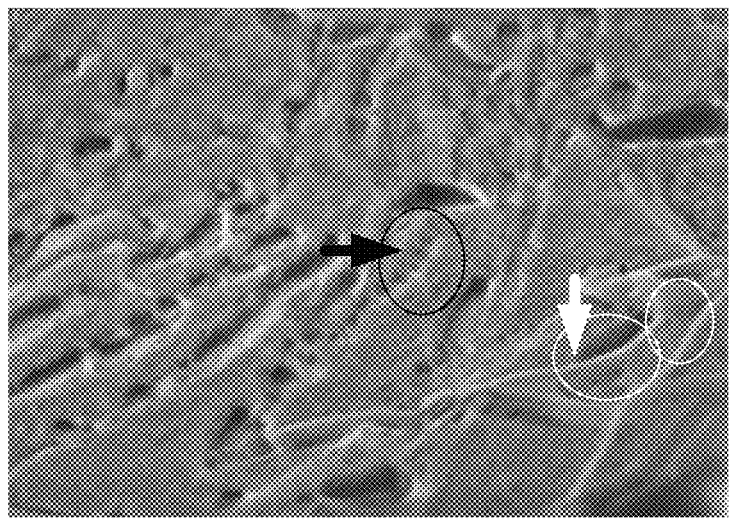
FIG. 8(A), FIG. 8(B) and FIG. 8(C) are electron microscope images to decide whether the formed particle were micelle or vesicles by using a low temperature and low vacuum scanning electron microscope. In the figure, structures shown with a white circle and white arrow are considered as crystals of salts. These shown with a black circle and black arrow are considered as vesicle-like substances.
Figure 8:
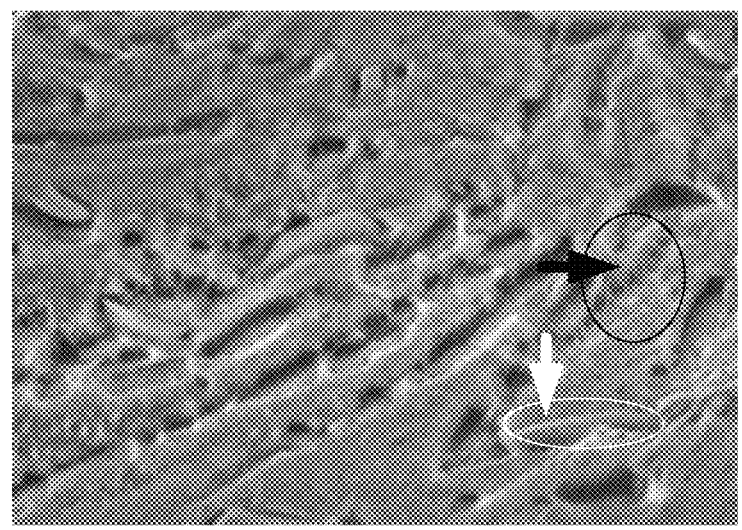
Figure 8:
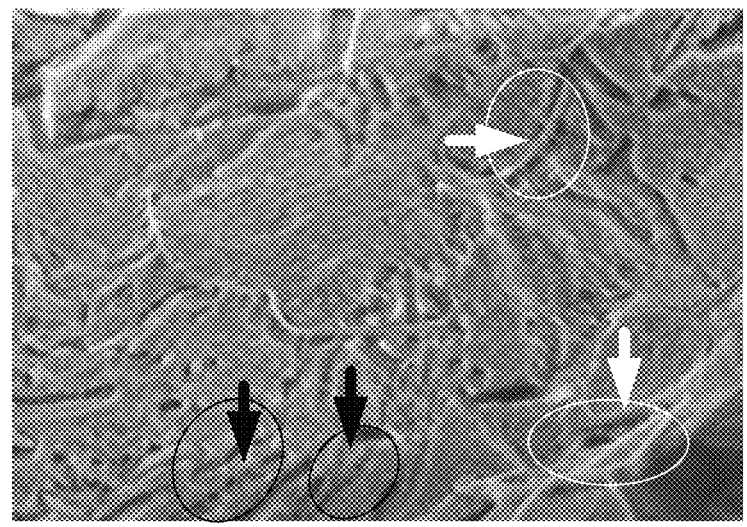

Next, according to the observation of the obtained micelle particles by using scanning electron microscope (SEM; Scanning Electron Microscope), a large number of particles having the particle size of about from 100 to 500 nm and a small number of those of about 500 nm were confirmed (see FIG. 8(A) to (C)).

From these results, it was clearly demonstrated that the micelle formed by using the aggregatable carrier for DDS of the present invention has the particle size distribution range between about 100 and 500 nm, and there were many particles having the particle size range between about 100 and 200 nm. Also, the electron micrograph by using SEM demonstrated that these particles have spherical micelle structures (see FIG. 7(A)).

(2) Confirmation of Fluorescence Resonance Energy Transfer

The silole dendrimers used in the example have the emission property that aggregated hydrophobic core parts of the silole gave AIE effects. Therefore, it was confirmed that the dendrimers emit, when they form the micelle structures. Therefore, we examined whether fluorescence resonance energy transfer (FRET: Fluorescence resonance energy transfer) between the silole and GFP occurs or not in the micelles composed of GFP-silole dendrimers to which GFP binds to the silole dendrimer (see FIG. 7(A)).

Unreacted fluorescent proteins and dendrimers, free molecules, were removed from the reaction mixture; we conducted the emission property experiment (see FIG. 7(C)). In order to examine the emission properties, the incubated products containing the silole dendrimer only was excited at a wavelength of 370 nm (dot-and-dash line), these containing GFP only was excited at the wavelength of 488 nm (dash line), these containing both of GFP and the silole dendrimer (the micelle of the present invention) was excited at the wavelength of 370 nm (solid line). The micelle being composed of silole-GFP conjugates, which is the products obtained by incubating GFP and silole dendrimer in formula (X), showed the emission caused by FRET to GFP around 510 nm.

As shown in FIG. 7(C), GFP showed the sharp emission peak around 510 nm, and it was considered to be due to FRET from the silole dendrimer to GFP. The silole dendrimer showed the emission peak around 480 nm. Also, the conjugate of GFP and silole dendrimer did not show a sharp emission peak, but it has the highest value around 510 nm. In contrast, when the micelles were collapsed, the emission from GFP considered to be caused by FRET, was also disappeared.

That is, the conjugate molecule composed of the dendrimer having AIE effect and the associative protein such as fluorescent protein is prepared to form the micelles. It was demonstrated that the micelles give FRET between the dendrimers and GFP, and FRET was lost when the micelles are collapsed. Also, the present endocytosis enhancing agent, the conjugate of GFP (a conjugated GFP) itself shows emission.

From the above, it was shown that the use of the micelle of the present invention as the aggregatable carrier for DDS enables to confirm the GFP-TPS and the conjugate of GFP delivered into the tissues or organs. Also, the fluorescence from the fluorescent protein may be traced even after the micelle delivered to the targeted tissue or organ collapses. Thereby, the intracellular environment and the like, to which the GFP protein were delivered, may be detected.

(Example 2) Preparation of the Fluorescent Protein which Binds the Target Peptide Sequence The target peptide sequence binding fluorescent protein was prepared as follows. The protein bound to the micelle of the present invention at the C terminal, and it bound to the target peptide, which binds the receptor expressed on the surface of a cancer cell, at N terminal.
(1) Inverse PCR
(1-1) Selection of the Peptide Sequence The peptide sequence of the selected target peptide was shown in the following Table 3. MCF-7 is a human breast adenocarcinoma-derived cell, having the sequence listed in the following Table 2, and it is sometimes referred to as "target type 1". MCF-2 is the variant of MCF7-1 having the sequence listed in the following Table 3, and it is sometimes referred to as "target type 2". Also, MCF7-1+α stand is another variant having the structure that the short peptide with α-helix, which is sometimes referred to as "α-stand", was connected to MCF7-1 as shown in the following Table 3, and it is sometimes referred to as "type 1 enhanced".

TABLE 2

| Cell Species | Peptide Sequence | SEQ ID NO: |
|---|---|---|
| MCF7-1 | DMPGTVLP | 1 |
| MCF7-2 | VPTDTDYSGG | 2 |
| MCF7-1 + α stand | DMPGTVLPGG GGGSEGEWQQQQHQWAKQE | 3 |

(1-2) Preparation of Primers

Primers for conducting inverse PCR of the peptide sequence shown in Table 2 were written in the following Table 3. Among these primers, SEQ ID NO: 1 (DMPGTVLP) and SEQ ID NO: 3(DMPGTVLPGG GGGSEGEWQQQQHQWAKQE) in the sequence listing were designed so as that elongation reaction initiates between the DM (residues 1 and 2 of SEQ ID NO: 3) and the PGTVLP (residues 3-8 of SEQ ID NO: 3) of the peptide sequence. SEQ ID NO: 2 (VPTDTDYSGG) was designed so as that the reaction initiates between the VP (residues 1 and 2 of SEQ ID NO: 2) and the DTDYSGG (residues 4-10 of SEQ ID NO: 2) of the peptide sequence. They were designed for conducting optimal inverse PCR.

TABLE 3

| Introduced Peptide Sequence | | Primer | SEQ ID NO: |
|---|---|---|---|
| DMPGTVLP (SEQ ID NO: 1) | F: | CCTGGTACTGTTCTTCCTGGTGGTATGAGTA AAGGAGAAGAACTT | 12 |
| | R: | CATATCGCGACCCATTTGCTGTCCACC | 13 |
| VPTDTDYSGG (SEQ ID NO: 2) | F: | ACTGATACTGATTATAGTGGAGGAATGAGTA AAGGAGAAGAACTT | 14 |
| | R: | AGGAACGCGACCCATTTGCTGTCCACC | 15 |
| DMPGTVLPGG GGGSEGEWQQ QQHQWAKQE (SEQ ID NO: 3) | F: | CAACAACAACAACATCAATGGGCAAAACAAG AAATGAGTAAAGGAGAAGAA | 16 |
| | R: | CCATTCACCTTCACTACCACCACCACCACCA GGAAGAACAGT | 17 |

(1-3) Preparation of the Template Plasmid for Inverse PCR

A template plasmid for inverse PCR was prepared by the method described in the following paper.

"Protease-sensitive signaling by chemically engineered intramolecular fluorescent resonance energy transfer mutants of green fluorescent protein.—Miho Suzuki, et al. Biochimica et Biophysica Acta (BBA)—Gene Structure and Expression Volume 1679, Issue 3, 17 Sep. 2004, Pages 222-229"

(1-3-1) Plasmid Construction for GFPuv5 Mutant

GFPuv5 was prepared from the pGFPgcn4 as follows. Firstly, the inverse PCR products, which has a synonymous mutation for gene manipulation was generated by using inverse PCR with 1167T mutation and forward primer, 5'CATTGAAGATGGCTCCGTTCAA (SEQ ID NO: 18) and reverse primer, 5'CATTGAAGATGGCTCCGTTCAA (SEQ ID NO: 19), were obtained. Subsequently, cyclization treatment of the products was conducted for obtaining GFPuv5. The construct obtained in this way was named pGFPgcn5.

After that, cDNA of GFPuv5 was cloned into pET21a (manufactured by Novaben Inc.) to express the protein, and then the protein was purified and named GFPuv5tag. The code region was amplified using the primers 5'CTCGAC-CAT[ATGGCTAG-CATGACTGGTGGACAGCAAATGGGT]CGCA TGAGTAAAGGAGAAGAACTTTTCA (SEQ ID NO: 20) and 5'TGACGTGAATTCATTA[GTGATGGTGATGGT-GATG]TTTGTAGAGCTCA TCCATGC (SEQ ID NO: 21). In SEQ ID NO: 20, an adhesive tag adhering to the epitope tag composed of 11 amino acids from the terminal for 10 proteins of T7 gene toward N terminal of GFPuv5 series was marked as [ ]. The SEQ ID NO: 21 provides His tag to C terminal of GFPuv5 series, and His tag in the sequence was shown as [ ].

The nucleotide sequences shown in the SEQ ID NOS: 1 to 3 were inserted into pET21a, and then it was digested with both of NdeI and EcoRI. The pGFPgcn plasmid was used for gene manipulation and the pET21a plasmid was used for protein expression under the control of the T7 promoter. The nucleotide sequences of the gene of GFPuv5 and the mutants thereof were confirmed by DNA sequencing (ABI PRISM 3100, manufactured by Genetic Analyzer). Three more synonymous mutations were found during the experiment. Those have the following mutations: agt to age at Ser at 30, cat to cac at His 78, and caa to cag at Gln 183.

The experiment was continued including these mutations, because these mutations were not harmful for the fluorescent proteins. The fluorescent intensity of the purified GFPuv5tag was about 1.9 times higher than that of GFPuv4tag. After that, either of the cysteine residues at position 48 or position 70 (sometimes referred to as "cysteine 48" or "cysteine 70") was replaced with randomized amino acid by inverse PCR using pGFPgcn5.

Both oligonucleotides 5' CTTAAATTTATTNNKACTG-GAAAAC (SEQ ID NO: 22) and 5' GGTAAGTTTTCCGTATGTTG (SEQ ID NO: 23) were used for mutation of cysteine 48. Both of 5' GTGTT-CAANNKTTTTCCCGTTATCCG (SEQ ID NO: 24) and 5' CATACGTCAGAGTAGTGACAAG (SEQ ID NO: 25) were used for the mutation of cysteine 70. Culture of E. coli BL21 (DE3) was transformed with the obtained plasmids and screened by using daylight excitation for those having strong fluorescence, and selected on an agar medium. Several mutants emitting strong florescence were obtained at position 48 (replaced with one of Ala, Asp, Glu, Gly, Ile, Leu, Asn, Pro, Ser, Thr, Val, and Tyr). However, the C70V cysteine mutant gave only proper fluorescence at position 70.

In order to produce double cysteine mutations GFPuv5 having strong fluorescent intensity, the plasmid having the single mutation was digested with both of NcoI and EcoRI and ligated to each region again. Selection was conducted by using the single mutants. The UV5CO tag (C48S/C70V) showed the highest fluorescence intensity among all the recombinants.

Next, cysteines were introduced at both positions 6 and 229 by inverse PCR, respectively. The plasmid having C48S mutation and a set of the following primers were used for introducing respective mutation.

```
For Glu replacement:
                                    (SEQ ID NO: 26)
5'TGTCTTTTCACTGGAGTTGTCCC
and
                                    (SEQ ID NO: 27)
5' TTCTCCTTTACTCATTTTTTC For Ile replacement:
                                    (SEQ ID NO: 28)
5'TGCACACATGGCATGGATGAGCTC
and
                                    (SEQ ID NO: 29)
5'CCCAGCAGCAGTTACAAACTC
```

Three protease tags having trypsin target sequence (Glu-Gly-Arg) have various spacer sequence, which were no spacer, Thr spacer or Gly-Thy spacer, and necessary cysteine was replaced between His-231 and Asp-231. These constructs were obtained by using puvC48Stag, the obtained plasmid (a template), and the primers shown in the following Table 4.

TABLE 4

| Plasmid Name | | Primers | SEQ ID NO: |
|---|---|---|---|
| pUV5trypS0tag (without spacer) | F:<br>R: | 5'CAGCGCCGTTGTGAGCTCTACAAATAATGAATT<br>5'TGTAATCCCAGCAGCAGTTAC | 30<br>31 |
| pUV5-trypS1tag (with Thr spacer) | F:<br>R: | 5'ACATGTGAGCTCTACAAATAA<br>5'ACGGCCCTGTGTAATCC | 32<br>33 |
| pUV5trypS2tag (with Gly-Thr spacer) | F:<br>R: | 5'GGAACATGTGAGCTCTACAAA<br>5'ACGGCCCTGTGTAATCCC | 34<br>33 |

(1-3-2) Purification of GFPuv5tag Mutant

E. coli BL 21 (DE3) was transfected by using all of the plasmids. 12 mL of E. coli at the stationary phase after overnight culture was seeded in 38 ml of LB medium supplemented with 50 μg/ml ampicillin and 0.5 mM IPTG, and incubated at 37° C. for 8 hours. The cells were collected by centrifugation at 2,500×g for 20 minutes and resuspended in 10 mL of PBS. The pellet of the cells was lysed in 10 ml of lysis buffer (pH 8.0) containing 50 mM Tris and 8 M urea at room temperature for 15 minutes, and then vortexed. The lysed cells were centrifuged at 1,200×g for 15 minutes, and the supernatant was taken to mix with $Ni^{2+}$-NTA resins (manufactured by Qiagen Co. Ltd.) which were suspended in PBS. After sequentially washing the resins with PBS and 20 mM imidazole, the bound GFPuv5tag mutant was eluted with 250 mM imidazole solution.

In order to exchange the buffer, the eluate was applied to PD-10 gel electrophoresis filtration column (manufactured by Amersham Bioscience Co. Ltd.), which was equilibrated with 10-fold diluted PBS. The eluted GFPuv5tag mutant protein was collected, and the concentrations thereof were determined by using Coomassie protein assay reagent (manufactured by Pierce Co.). Purified GFPuv tag mutants were analyzed by 15% SDS-PAGE.

Nucleic acid sequence of the template plasmid for inverse PCR was shown as SEQ ID NO: 26.

(1-4) Conditions for PCR

A reaction mixture shown in the following Table 5 was prepared, and the inverse PCR was conducted under the condition shown in the following Table 6.

TABLE 5

| Components | Amount (μL) |
|---|---|
| Template (plasmid->pET21a (+) NSS25 | 5 |
| KOD Dash Buffer (Toyobo Co. Ltd.) | 5 |
| 2 mM dNTP (Toyobo Co. Ltd.) | 5 |
| F primer (2.5 pmol) | 10 |
| R primer (2.5 pmol) | 10 |
| KOD Dash (2.5 U/μL) (Toyobo Co. Ltd.) | 0.5 |
| Sterile distilled water | 14.5 |
| Total | 50 |

TABLE 6

| Temp. (° C.) | Reaction period (min.) | Cycles |
|---|---|---|
| 95 | 3 | — |
| 98 | 0.1 | 5 |
| 65 | 2 | |
| 70 | 4 | |
| 98 | 0.1 | — |
| 74 | 2 | 25 |
| 70 | 4 | |
| 70 | 7 | |

TABLE 6-continued

| Temp. (° C.) | Reaction period (min.) | Cycles |
|---|---|---|
| 4 | — | — |
| 4 | — | — |

(1-5) Confirmation by Gel Electrophoresis

A portion of the PCR solution was taken, and subjected to gel electrophoresis with 0.8% PAGE at voltage 100 V for 30 minutes of applied voltage time to confirm the amplified peptides in each sample. The result of the electrophoresis was shown in FIG. 9(A) and FIG. 9(B).

(2) Removal of Independent A Sequence and Purification of PCR Products

The reaction mixture shown in the following Table 7 was prepared and reacted at 120° C. for 30 minutes to remove the independent A sequence which was produced by the PCR. After that, the PCR products were purified by using QIAquick (a registered trademark), PCR Purification Kit (manufactured by QIAGEN) according to the instruction attached to the kit.

TABLE 7

| Composition | Amount (μL) |
|---|---|
| inverse PCR product | 50 |
| 10 × NE Buffer 2.1 (New England Biolabs Inc. (NEB)) | 1 |
| 10 mg/ml BSA (NEB) | 2 |
| 2 mM dNTP | 8.3 |
| T4 DNA polymerase (3,000 unit/μL) (NEB) | 0.5 |
| Total | 60 |

(3) Ligation Reaction

Subsequently, the reaction mixture shown in the following Table 8 was prepared and reacted at 16° C. for more than 3 hours to prepare a circular plasmid for transformation of E. coli DH5a described later. Depending on the variants, the temperature, 25° C., 37° C., and the like were used.

TABLE 8

| Composition | Amount (μL) |
|---|---|
| PCR product | 8 |
| 10 × T4ligase B (NEB) | 1 |
| T4 DNA polynucleotide kinase (40,0000 unit/μL) (NEB) | 0.5 |
| T4 DNA ligase (10,000 unit/μL) (NEB) | 0.5 |
| Total | 10 |

(4) Transformation of E. coli DH5α

10 μL of competent cells of E. coli DH5α (manufactured by BioDynamics Laboratory) was thawed on ice immediately before use, and then prepared a competent cell solution. One μL of the ligation reaction solution was added to the competent cell solution, and then left on ice for 30 minutes. After that, the solution was incubated at 42° C. for 30 seconds and then cooled on ice for 2 minutes. 90 μL of SOC medium (manufactured by TOYOBO Co., LTD.) was added to the solution, and reacted on a shaker at 37° C. for 1 hour. Thereafter, it was seeded on LB selection medium supplemented with ampicillin (manufactured by TOYOBO Co., LTD.), and incubated for overnight at 37° C.

(5) Colony PCR

Colonies obtained from the transformation were subjected to Colony PCR to confirm the predicted inserts.

(5-1) Preparation of the Reaction Mixture for PCR

The reaction mixture for colony PCR shown in the following Table 9 was prepared.

TABLE 9

| Composition | Amount added (μL) |
| --- | --- |
| KOD Dash Buffer (Toyobo Co. Ltd.) | 2 |
| 2 mM dNTP | 2 |
| Double His primer (2.5 pmol) | 4 |
| pET primer | 4 |
| KOD Dash (2.5 U/μL) (Toyobo Co. Ltd.) | 0.2 |
| Sterilized distilled water | 7.8 |
| Total | 20 |

The reaction mixture for colony PCR was poured into a PCR tube. *E. coli* grown on the LB medium supplemented with ampicillin was collected and added to the tube. PCR was conducted according to the program shown in the following Table 10.

TABLE 10

| Temp. (° C.) | Reaction time (min.) | Cycles |
| --- | --- | --- |
| 95 | 3 | — |
| 98 | 0.5 | 5 |
| 50 | 0.5 | |
| 70 | 0.5 | |
| 98 | 0.1 | — |
| 72 | 0.5 | 25 |
| 70 | 0.5 | |
| 70 | 7 | |
| 4 | — | — |

(5-2) Electrophoresis

Electrophoresis of the PCR reaction mixture was conducted with 1.2% PAGE at applied voltage of 100 V for 30 minutes. The colonies of which amplification were confirmed were inoculated into the culture bottle containing LB liquid medium (manufactured by TOYOBO Co., LTD.) and incubated at 37° C.

(6) Purification of Plasmid

The plasmid in *E. coli* cultured in the LB liquid medium was purified by using Wizard Plus SV Minipreps. DNA Purification System (manufactured by Promega Co.) according the instruction attached thereto. After that, the sequences of the purified plasmid were sent to Eurofin Genomics Co., Ltd. for their analysis.

(7) Transformation of *E. coli* BL21 (DE3)

Ten μL of *E. coli* BL21 (DE3) competent cells (manufactured by BioDynamics Laboratory) were thawed on ice immediately before use, and then prepared the competent cell solution. One μL of the plasmid solution, which was confirmed to contain the target sequence by the sequencing, was added to the competent cell solution, and left to stand on ice for 30 minutes.

After that, the solution was incubated at 42° C. for 30 seconds and then cooled on ice for 2 minutes. 90 μL of SOC medium (manufactured by TOYOBO Co., LTD.) was added to the solution, and reacted on a shaker at 37° C. for 1 hour. Thereafter, it was seeded on LB selection medium supplemented with ampicillin, and left to stand overnight at 37° C. Next day, transformed colonies emitting green fluorescence were collected, and inoculated into culture bottles containing 1 ml of LB liquid medium supplemented with ampicillin. Then, they were left to stand overnight at 37° C. for pre-culture.

(8) Purification of the Fluorescent Protein Binding to the Target Peptide Sequence (8-1) Colony Cultivation For samples, 4 tubes in 50 mL size to which both of 4 ml of the LB liquid medium supplemented with ampicillin and 290 μL of the pre-cultured solutions were added were prepared, and then cultured on the shaker at 28° C. for 4 hours. After that, 43 μL of 100 mM IPTG (isopropyl-β-thiogalactopyranoside) was added to them, and they were cultured overnight at 28° C. on the shaker.

(8-2) Recovery of the Protein

Next day, the cultures in the four tubes were collected into one tube. Three tubes of which contents were transferred were washed with 1 ml PBS (−) buffer (manufactured by Wako Pure Chemical Industry, Ltd.), and the washed solutions were also added to the collected tube to which the cultures were collected. The tube containing the collected cultures was centrifuged at room temperature for 5 minutes at 5,000 rpm (the name of centrifuge: KUBOTA3740, the rotor number: KUBOTA AF2018, manufactured by KUBOTA Co.).

After that, (i) the supernatant was removed and 3 ml of PBS (−) buffer was added to the precipitation pellet (ii) to vortex well, and then the tube was centrifuged at 5,000 rpm for 5 minutes. The steps (i) and (ii) were repeated twice. Four ml of B-PER Lysis Buffer (manufactured by Reagent) was added to the precipitation pellet, and it was capped and stirred overnight at room temperature on the shaker.

(8-3) Purification by His-Tag

Two ml of Ni-NTA Agarose (manufactured by QIAGEN) was put in 15 ml tube, (i) the tube was centrifuged at 1,000 rpm for 1 minute, (ii) the supernatant was discarded, and 1×PBS buffer was added to the tube and vortexed well. The steps (i) and (ii) were repeated three times for preparing Ni-NTA resin.

The tube containing B-PER Lysis buffer solution was centrifuged at 12,000 rpm for 10 minutes at room temperature, and then the supernatant was transferred to a 15 ml Falcon tube. 400 μL of well stirred Ni-NTA resin was added to the tube, and then the tube was placed on the rotary shaker and shook at room temperature for 10 minutes. After that, the tube was centrifuged at 1,000 rpm for 1 minute at room temperature, and the supernatant was discarded. (iii) 4 mL of 1×PBS buffer was added to the tube and vortexed well, (iv) the tube was centrifuged at 1,000 rpm for 1 minute at room temperature, and the supernatant was discarded. The steps (iii) and (iv) were repeated twice.

After that, (v) 4 ml of 20 mM imidazole (manufactured by Wako Pure Chemical Industry, Ltd.) was added to the tube and vortexed well, (vi) the tube was centrifuged at 1,000 rpm for 1 minute at room temperature, and the supernatant was removed. The steps (v) and (vi) were repeated twice. 500 μL of 250 mM imidazole was added to the tube, and then it was stirred at room temperature for 10 minutes with the rotary shaker. Thereafter, the tube was centrifuged at 1,000 rpm for 1 minute, and the supernatant emitting green fluorescence was transferred to a new 15 ml Falcon tube to prepare the protein purified solution for the gel filtration in next stage.
(8-4) Purification by Gel Filtration Imidazole in the protein purified solution was exchanged with PBS and the solution was purified to obtain the target peptide sequence binding fluorescent protein of interest. In the procedures described above, Nap 5 column manufactured by GE Heath Care Japan KK. was used to conduct the purification according to the instruction attached thereto.
(9) Selection of the Target Peptide Sequence Binding Fluorescent Protein The concentration of the target peptide sequence binding fluorescent protein obtained from the purification procedure was measures by using absorbance, 280 nm, and the chromophore concentration (chromophore forming ability) was measured by using absorbance, 488 nm, according to the conventional method. The proteins of which ratio of A 488/A 280 exceeded 1.5 were selected as the target peptide sequence binding fluorescent protein of the interest. The result was shown in Table 11.

TABLE 11

| Type | Absorbance | Wave length (nm) | | Ratio |
|---|---|---|---|---|
| | | 280 | 488 | 488/280 |
| Target type 1 | sample 1 | 0.2459 | 0.5246 | 2.1335 |
| | sample 2 | 0.2487 | 0.5295 | 2.1289 |
| | sample 3 | 0.2494 | 0.5307 | 2.1280 |
| Target type 2 | sample 1 | 0.4280 | 0.8236 | 1.9241 |
| | sample 2 | — | — | — |
| | sample 3 | — | — | — |
| Target type 1 enhanced | sample 1 | 0.6300 | 0.9039 | 14348 |
| | sample 2 | 0.7695 | 1.1427 | 14850 |
| | sample 3 | — | — | — |
| Non-target type | sample 1 | 0.6689 | 13 189 | 1.9717 |
| | sample 2 | 0.4544 | 0.9915 | 2.1821 |
| | sample 3 | 1.0079 | 20110 | 1.9952 |

(Example 3) Preparation of the Target Peptide Sequence-Binding Micelle (Associated Fluorescent Protein Driving Type Micelle)

Figure 6:
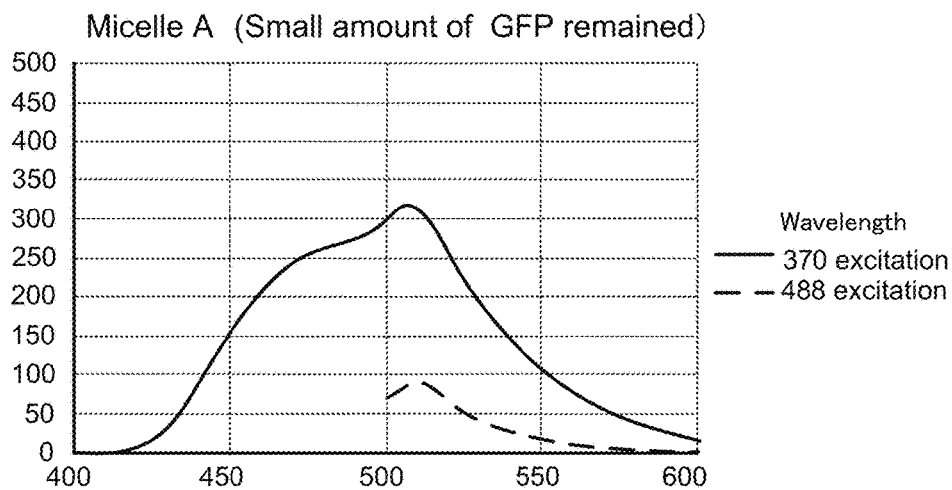
FIG. 6(A), FIG. 6(B) and FIG. 6(C) show a result of the fluorescent detection that the micelle formation after presenting the fluorescent protein on the carbosilane dendrimer, and the amount of the fluorescent protein conjugate (GFP remains) shows different fractions.
Figure 6:
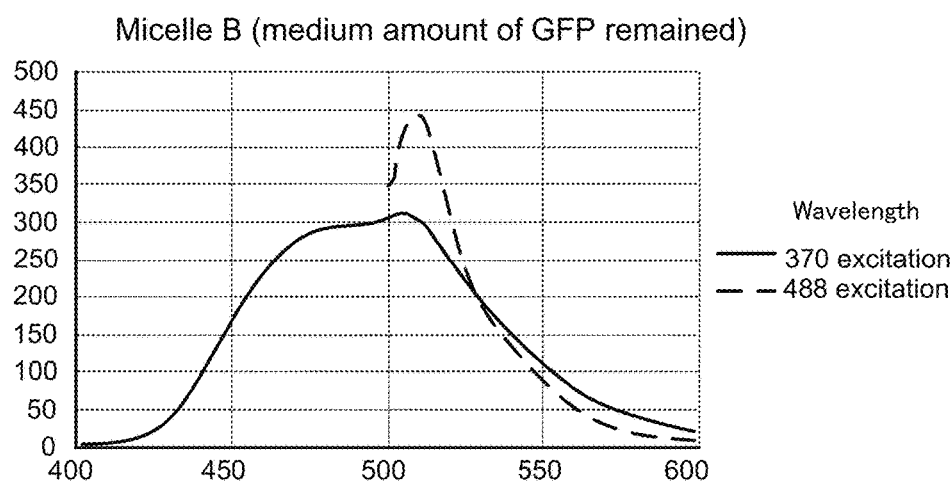
Figure 6:
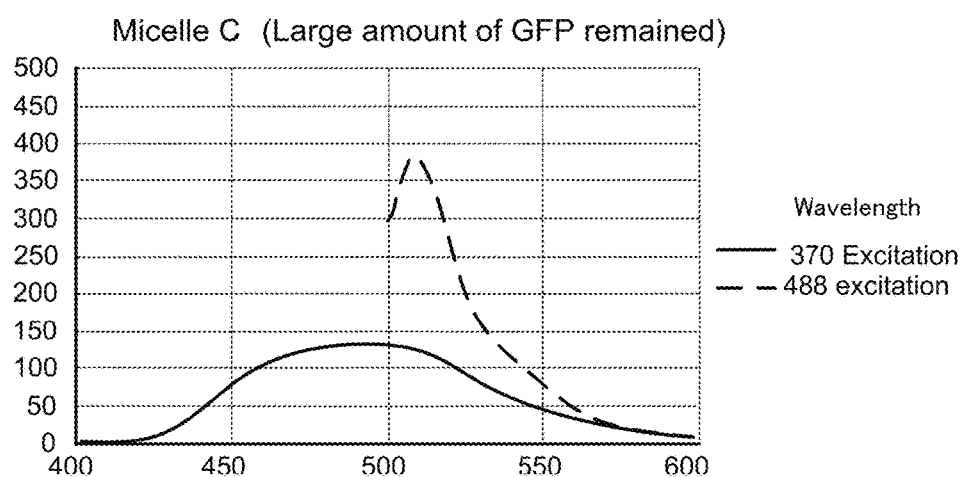

Instead of unmodified GFP, the aggregable molecule to which the target peptide sequence is bound is prepared. Subsequently, the micelle, the conjugated fluorescent protein driving micelle, as the same as those employed in the example 1, were prepared to investigate the amount of the conjugate existed in the micelle fraction.
(1) Emission Properties A variety of the conjugate amount in the micelle fractions, reacted as described above, depending on the target peptides were measured as the same as that in Example 1 (see, FIGS. 6(A) to (C)). FIGS. 6 (A) to (C), the amount of the aggregates is shown in a dotted line (dashed line), and GFP-TPS is shown in a solid line. The horizontal axis shows the particle number which shows fluorescence/50,000 particles, and the horizontal axis shows the detection wave length (nm). An emission peak was also observed around 510 nm in the target peptide sequence-binding micelle as the same as that in the example 1.
(2) Confirmation of the Existence of the Conjugate Next, the amount of the endocytosis enhancing agent of the present invention (the aggregated body) existed in the micelle fraction was confirmed for the case wherein the following 4 types were used: without target peptide sequence (MCF7-0: non-target type); with the target type (MCF7-1 (the target type 1); MCF7-2 (the target type 2)); and the target peptide+α stand (MCF7-1+α (the enhanced target type 1)).
(3) Confirmation of GFP Bounds to the Target Peptide
(3-1) Classification of the Fractions when y Typed of the Aggregable Molecules are Used Each GFP produced as described above was mixed with TPS at the ratio of 10:1. Then, the mixture was stood at 37° C. overnight to obtain the aggregates of the target peptides with GFP (the peptides are MCF7-0, MCF7-1, MCF7-2, and MCF7-1+α) and GFP-TPS.

Then, the content amount of the aggregated body, which is referred to as the "remained GFP amount", was classified on the basis of the intensity ratio ($I_0$) between that of the excitation wavelength 370 nm—measurement wavelength 510 nm and that of the excitation wavelength 488 nm—measurement wavelength 510 nm into 3 classes: A ($I_0 \leq 1.0$) (less remained GFP content amount)), B ($1 \leq I_0 \leq 2.0$) (medium remained GFP content amount), and C ($I_0 \leq 2.0$ (more remained GFP content amount) (See, FIGS. 6 (A) to (C)).

On the basis of the following reasons, we classified as described above. Firstly, as described above, the aggregable molecule presenting the protein is obtained by reacting the carbosilane dendrimer and GFP overnight as shown in FIG. 6(A), FIG. 6(B) and FIG. 6(C). However, the amount of the protein, GFP, incorporated in the aggregable molecule as a part was varied; the reason is clearly shown in the chemical formula (II), namely, the sites of the silole to be used for binding with GFP are six.

Here, the shape of the fluorescent wavelength excited at the wavelength of 370 nm shows FLET efficiency of the micelle. Therefore, it shows higher the ratio between the intensities at 480 nm (the fluorescence from the aggregated body having silole backbone) and 510 nm (the fluorescence from GFP), better the FRET efficiency.

Also, it means to measure the fluorescence of the excitation wavelength at 488 nm that total amount of GFP which independently exists from GFP inside the micelle, and reasons are as follows: the fluorescent amount behaves independently from the efficiency of FRET as described above; they are predicted as remained GFP, and the existence of conjugated GFPs were actually confirmed by subjecting the micelle components. As a result, it was shown that there is difference among the amount of the conjugates belonging to the 3 classes as mentioned above depending on the used target peptides.

TABLE 12

| | Generation ratio of conjugate*1 (other than he experiment for inclusion) | | | |
|---|---|---|---|---|
| | A small | B medium | C large | Generation ratio of C (%) |
| MCF7-0 (Non-target tyke) | 8 | 3 | 3 | 21.4 |
| MCF7-1 (Target type 1) | 11 | 6 | 4 | 19.0 |
| MCF7-2 (Target type 2) | 3 | 7 | 8 | 44.4 |
| MCF7-1 + α (Target type 1 reinforced) | 3 | 2 | 7 | 58.3 |

*1 The ratio of the fluorescent intensity excited at the wavelength of 488 nm and that excited at the wavelength of 370 nm
*2: A ≤ 1.0, 1.0 < B < 3, 3.0 ≤ C As shown in the table 12, the generation ratio of the conjugate was significantly higher in the molecule having the target sequence either of MCF7-2 or MCF7-1+α than those having other sequences.

(3-2) Variety of the GFP-Conjugate Depending on the Target Peptides

Figure 9:
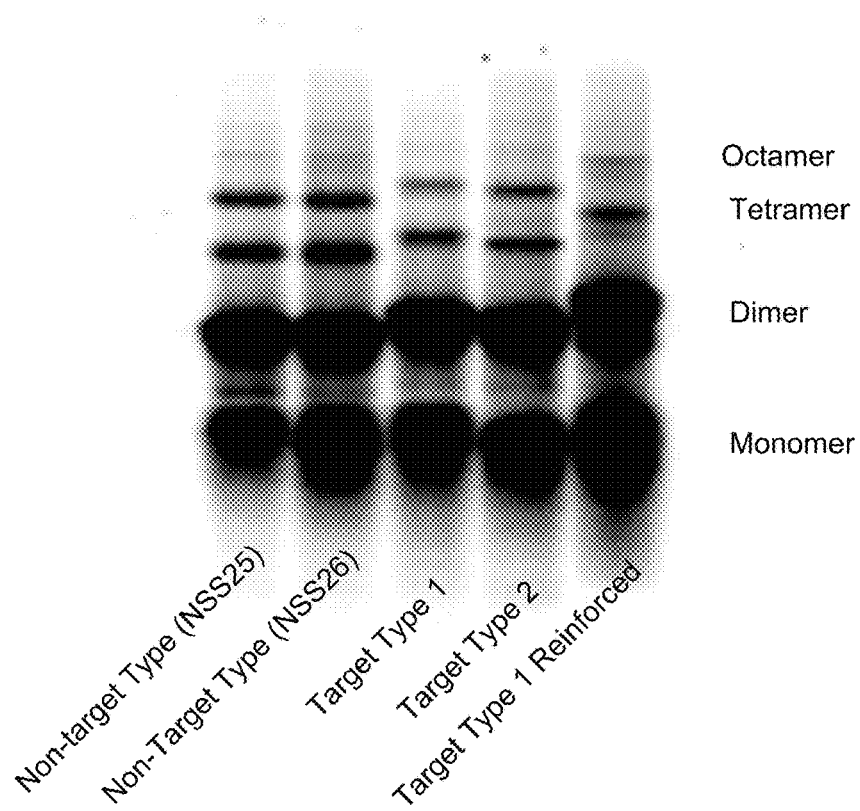
FIG. 9(A) and FIG. 9(B) show the result of the gel electrophoresis for studying the conjugate contained in the target peptides used.
Figure 9:
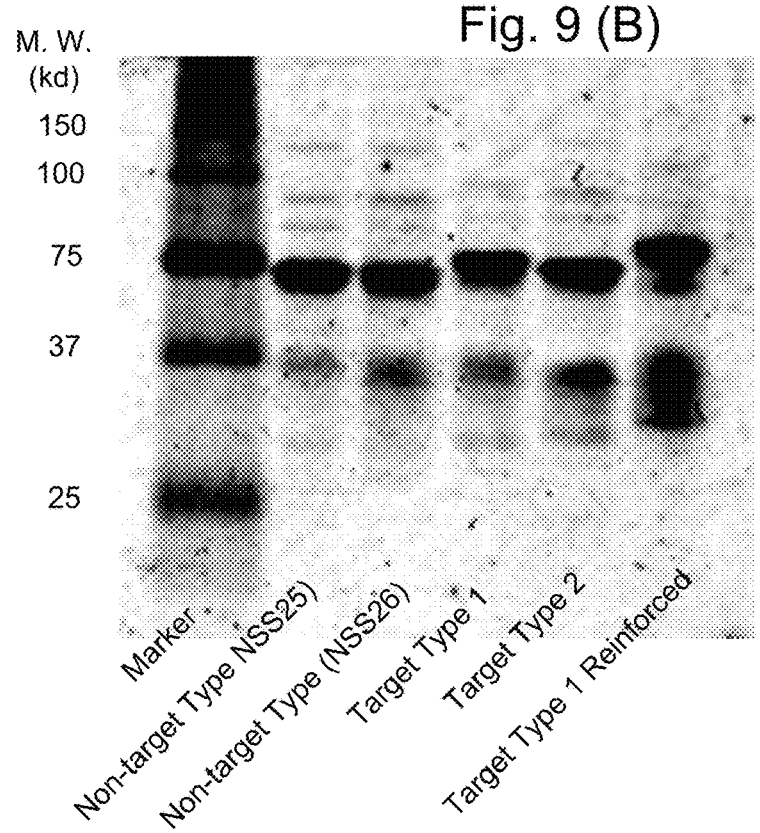

Ten μL of the protein solution, of which concentration was 5 μM, was taken out from each solution includes the aggregable molecules obtained as described above was subjected to gel electrophoresis without any treatment to confirm the conjugate included thereof. Results are shown in FIGS. 9 (A) and (B). (A) is the fluorescence detection result, and (B) is CBB staining result. As described above, it was confirmed that the dimer, tetramer, and octamer are existed.

(Example 4) Incorporation Experiment of DDS Liposome or the Micelle-2 (the Association Bodies are Co-Existed)

(1) Variety of the Micelle Solution Including the Aggregable Molecule Depending on the Target Peptides-1

Conjugates of GFP without the target peptide obtained in Example 3 are classified into the groups the solution including the high content amount of the conjugate (the micelle C), the medium content amount of that (the micelle B), and the less amount of that (the micelle A) to prepare the sample solutions. Then, they were subjected to gel electrophoresis to discuss which mer of the conjugates were formed. SDS is added to 12% of running gel-4% stacking gel at final concentration of 0.1%. The fluorescent measurement condition for each sample is set that the sensitivity to 3×3, Max of the fluorescent intensity to 500. When the micelle C equals to 1, the amount of the micelle A was double, and that of GFP was 5 times were applied to conduct gel electrophoresis and 20 mA for 2 hours. In this experiment, both of the micelle solution and GFP were applied as undiluted solutions.

Results are shown in FIGS. 10 (A) to (D). Here, both of (A) and (B) show the results of FITC staining (by the laser 475 and PMT500). Also, both of (C) and (D) show the results of decolororation after CBB staining (by the laser 635 (cy5) and PMT500).

As shown in both of FIGS. 10 (A) and (B), when the sample containing the conjugate being composed of the aggregable molecule in high content is used, it gives the solution containing tetramer or octamer in high content in addition to the monomer or dimer. In this time, the experiment used MCF7-0 gave the solution containing the conjugate in low content so that the micelle C was not subjected to gel electrophoresis. Also, the micelle A using MCF7-0 gave that the almost same amount of the tetramer and the octamer as those when sole GFP was electrophoresed. In both of FIGS. 10 (C) and (D), we could confirm that both of the monomer and dimer were existed; however, we could confirm neither the tetramer nor the octamer.

(2) Variety of the Micelle Solution Containing the Aggregable Molecule Depending on the Target Peptide-2

Next, under the same conditions for the gel electrophoresis employed in Example 2, GFP, which was concentrated by using Amikon 100K to be associated, the sample containing MCF7-1 and that containing MCF7-2 were compared. The fluorescent measurement was conducted under the condition for each sample at the sensitivity 3×3 of the spectrophotometer, and then 5 μL or 20 μL of the micelle C having MCF7-1—protein (300 μM) is applied. The micelle C having MCF7-2—protein (300 μM) is applied at the same amount. The fluorescence detection or staining is performed according to those as mentioned (1).

The results are shown in FIGS. 11 (A) to (D). Both of FIGS. 11 (A) and (B) show the results of the fluorescent detection (FITC (Laser 635) and PMT 400). Also, both of (C) and (D) show the results of CBB staining (FITC (Laser 635 (cy5)) and PMT 600). These results were the same as those shown in the above-mentioned (1).

(3) Correlation Between the Incorporated Amount of the Protein Mixture and the Amount of the Associated Protein The micelle with the target peptide or without the target peptide are respectively added into the wells, wherein MCF-7 cells are cultured, at 50 μL of the volume to study the relationship of the incorporation amount of the micelles into the cells and the amount of the conjugate in the same fraction.

Against $1\times10^9$ cells/well, 50 μL of the sample containing both of the micelle and the conjugate being composed of the aggregable molecules are added. It is incubated at 37° C. for 9 hours, and then it is detected by using FACS.

FACS data was summarized: the horizontal axis is set to the emission intensity of the fluorescence showing the classifications of the remained protein (herein fellow, it is collectively referred to as the "micelle"); and the longitudinal axis is set to the ratio (%) of the cell numbers, wherein the cell clearly has the fluorescent intensity among 50,000 cells of the FCS data clearly. The results are shown in FIGS. 12 to 15.

Figure 12:
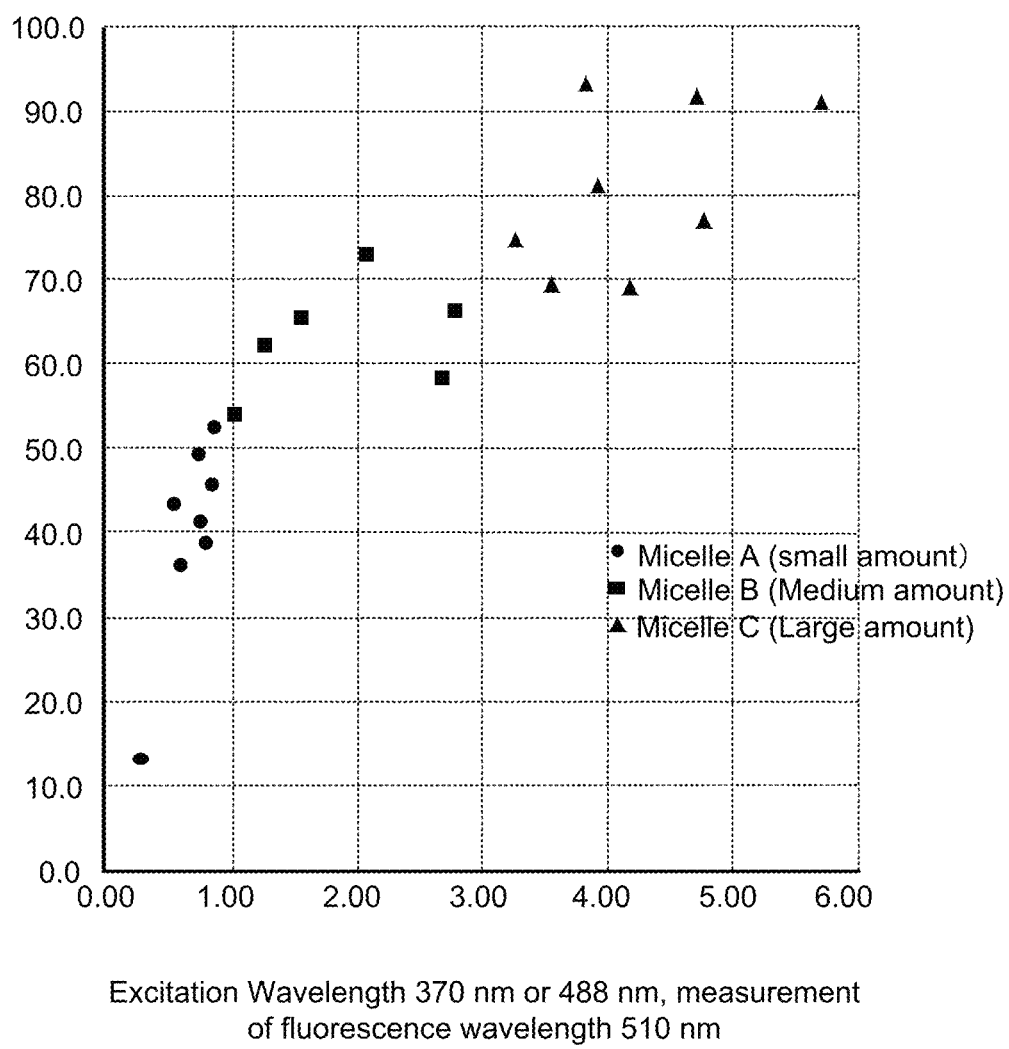
FIG. 12 is the graph showing the result of the change for the micelle incorporation into the cell depending on the target peptides contained in the conjugate being used (No. 1).
Figure 13:
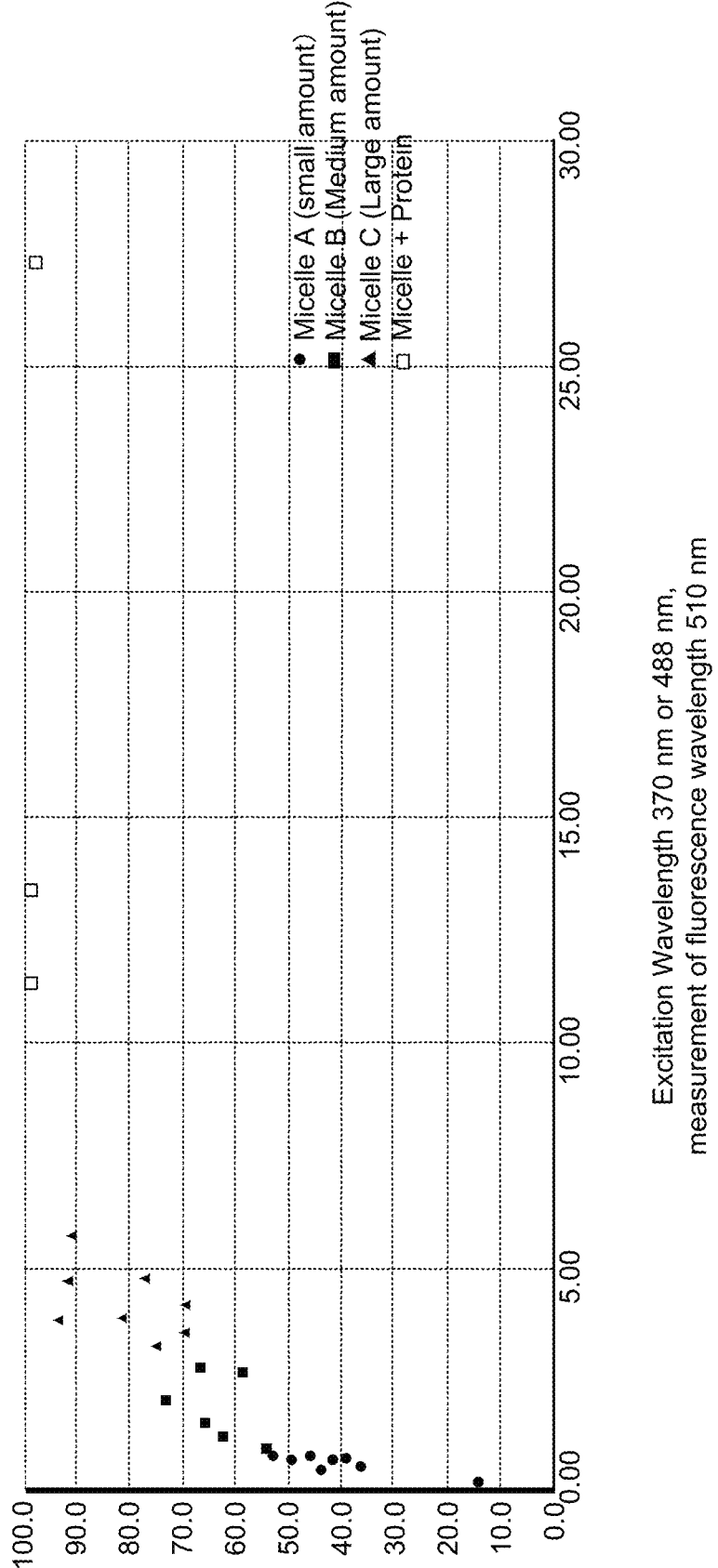
FIG. 13 is the graph showing the result of the change for the micelle incorporation into the cell depending on the target peptides contained in the conjugate being used (No. 2).

In both of FIGS. 12 and 13, the black circle shows the micelle A (containing less amount of the conjugate); the black square shows the micelle B (containing the medium amount of the conjugate); the black triangle shows the micelle C (containing the much amount of the conjugate); the white square shows the incorporated amount when GFP was added to the micelle. It was confirmed that the incorporated amount of the micelle into the cells are increased depending on the increase of the content amount of the conjugate composed of the aggregable molecule; namely, there is the correlation between them.

Figure 14:
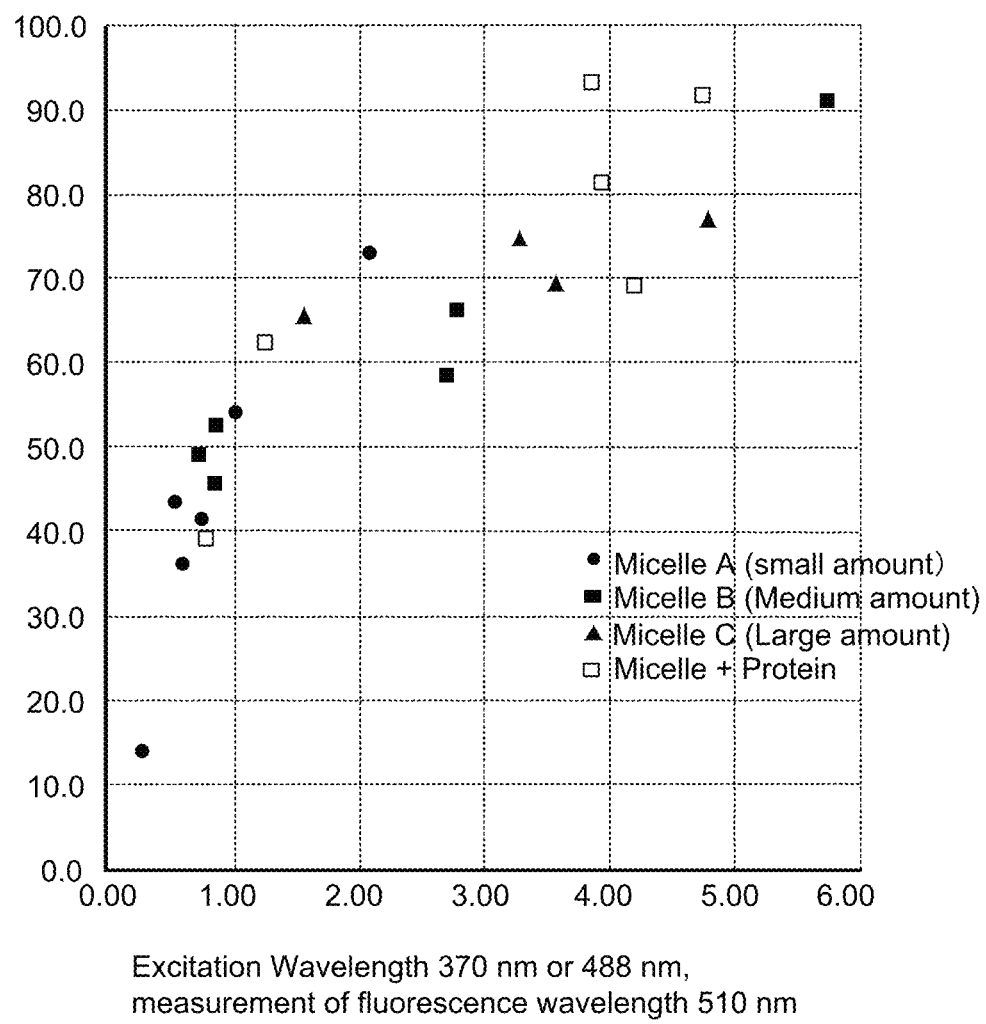
FIG. 14 is the graph showing the result of the change for the micelle incorporation into the cell depending on the target peptides contained in the conjugate being used (No. 3).

Both of FIGS. 14 and 1 show the difference derived from the presence or absence of the target peptide bounds to GFP and the target peptides themselves. From the results, it was confirmed that the incorporated amount was increased in the target peptide bounds micelle—protein. The results after treatment of the fluorescent protein on the basis of the fluorescence lifetime supported the results.

As described above, it was demonstrated that the endocytosis enhancing preparation of the present invention strongly enhances the incorporation of the micelle being composed of the carbosilane dendrimer (or the vesicle) presenting GFP into the cells.

(Example 5) Study of the Buffer for the Micelle Preparation

Until now, we conducted the MCF-7 micelle preparation in only one buffer, 1×PBS. In order to conduct the experiment for incorporation of the drugs, we had to consider the solubility or stability of the variety of the drugs to be incorporated. Therefore, we studied whether the micelle preparation in the buffer other than 1×PBS was possible or not.

(1) Study of the Buffer to be Used

We prepared following 4 buffers: Tris-HCl buffer, which is most popularly used around pH 7 in the field of the molecular biology; HEPES buffer, which is one buffer included in Good buffer (it is collectively referred to as 12 buffers shown in Norman Good et, al. in 1966); citrate buffer as the organic buffer; and carbonate buffer as the inorganic buffer. The micelles are formed in each buffer and separated, and used to obtain the micelle fraction in PBS, of which inside is one of the above-mentioned buffer, and outside is PBS. Their fluorescence and the particle size were measured to confirm short-term stability (the stability of the micelle 1 to 2 days after their preparation).

(2) The Micelle Formation in 50 mM Tris-HCl Buffer (pH 8.0)

(2-1) Conventional Preparation Method of the Micelle

Until now, the micelle was prepared in 1×PBS, because it includes the same ion species as these in the living body and it is thought to be closer to the biological condition due to isotonic.

However, by using the conventional method, inside of the micelle is filled with the buffer used to form the micelle. Therefore, we studied the micelle formation in the buffer which has good compatibility for the drugs. As the generally used buffers, there are mentioned such as Tris-HCl buffer, Hepes buffer, MOPS buffer, CHAPS buffer and the like. Among them, firstly choose Tris-HCl buffer to study the micelle formation in 50 mM Tris-HCl (pH 8.0) (herein below it is referred to as simple "Tris buffer").

(2-2) Modification of the Micelle Preparation

The buffer to be used was 50 mM Tris-HCl (pH 8.0). NICK column was washed by using Tris buffer in 5 times, and then it was equilibrated by using Tris buffer.

(2-3) Preparation of the Micelle

By using Amicon 10 k Filter, the column was centrifuged at 14,000×g for 15 minutes to concentrate 219.2 µL of the fluorescent protein for MCF-7 micelle. It was diluted by using Tris buffer to 99 µL, 1 µL of 100 mM DTT was added and then stood for 10 minutes to prepare the sample mixture.

The sample mixture is applied to NICK column being equilibrated as described above, and 365 µL of Tris buffer is added into it, and then 380 µL of Tris buffer is used for elution. After that, 10.28 µL of TPS is added into the eluted solution, and the solution is vortexed for 10 minutes and stood at 37° C. overnight to obtain the micelle reaction mixture. The reaction mixture includes the formed micelle (hereinbelow, it is referred to as "MCF-7 micelle".) and the associated fluorescent protein for MCF-7 micelle.

Tris buffer employed here is prepared as 1 M Tris-HCl (pH 8.0) as the stock solution, which is used by diluting 20 times with MilliQ (Merk Millipore).

(2-4) Separation of the Micelle

The micelle reaction mixture as described above is applied onto Amicon 100 k Filter, and then it is centrifuged at 14,000×g for 10 minutes to separate the upper-filter solution and the lower-filter solution.

100 µL of 1×PBS is added to the filter includes the upper-filter solution, and then it is centrifuged at 14,000×g for 10 minutes as washing operation. The washing operation is repeated 3 times to exchange Tris buffer to 1×PBS. The upper filter solution after the buffer exchange (the micelle fraction solution) is centrifuged by using the tabletop centrifuge to collect the micelle. Next, the suitable volume of 1×PBS is added into the filter being empty and stood 10 minutes, and the micelle is further recovered after reversing the upside of the filter to down. Thus recovered solution is diluted by using 1×PBS to 160 µL. For 20 timed dilution (2.5 µM), 95 µL of 1×PBS is added to 5 µL of the portion taken out from the solution to dilute.

The particle size of the micelle included it was measured. For 50 timed dilution (1 µM), 392 µL of 1×PBS is added to 8 µL of the portion taken out from the solution to measure its fluorescence.

Figure 20:
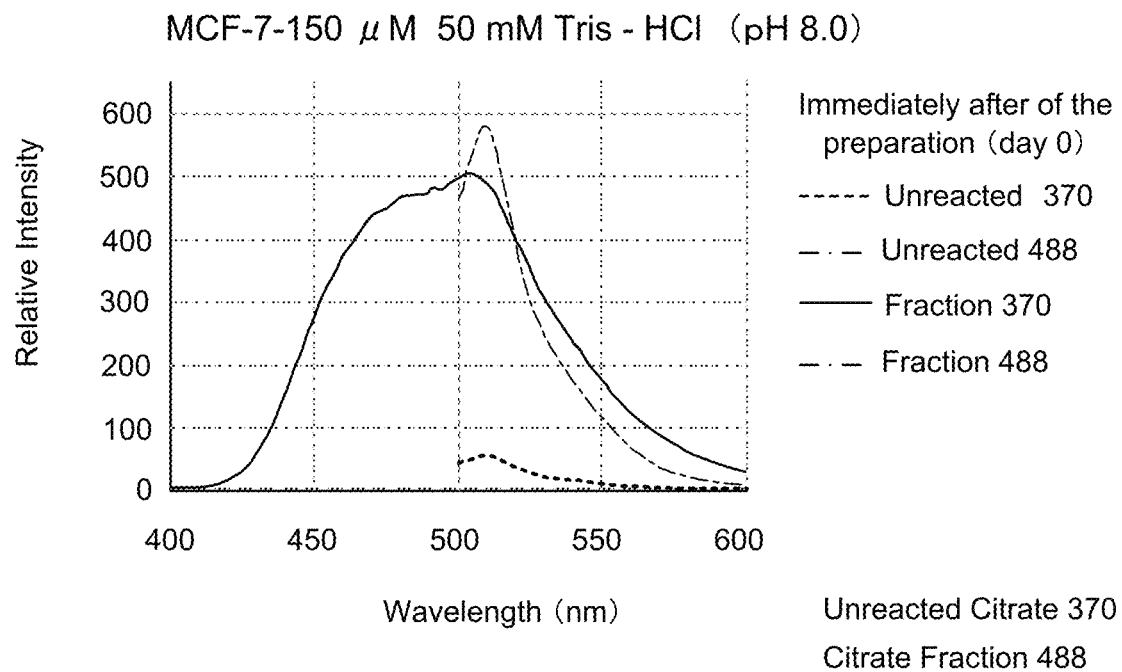
FIG. 20(A) and FIG. 20(B) show the fluorescent characteristics of the micelle, when 50 mM Tris-HCl buffer (pH 8.0) is used (immediately after the preparation).
Figure 20:
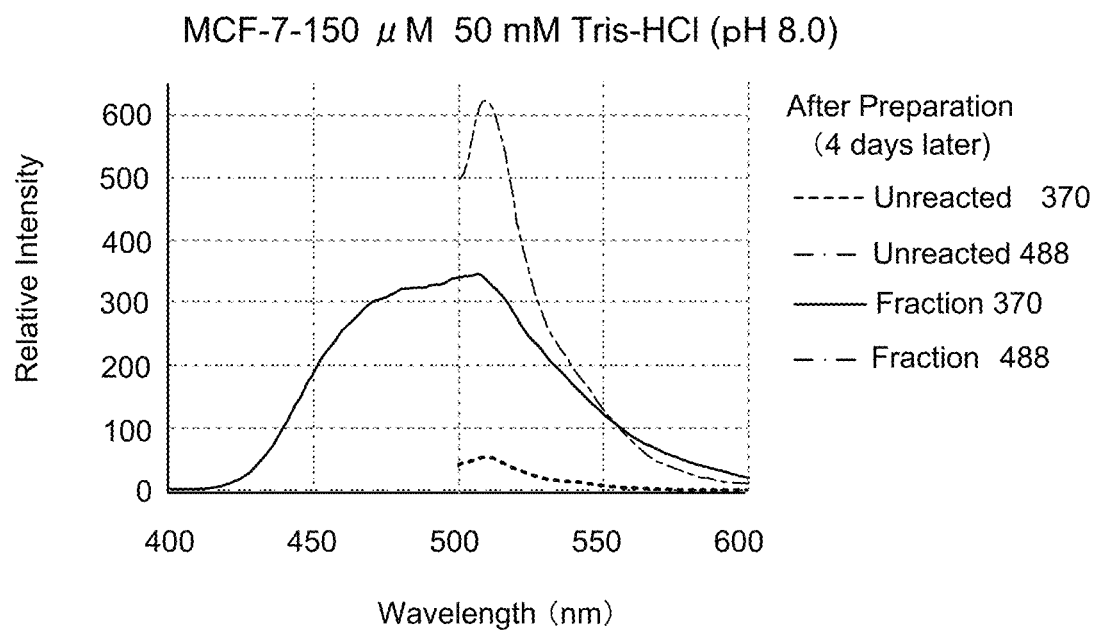

From the lower-filter solution (the micelle unreacted fraction), 5 µL of the portion is taken out, and diluted 20 times to adjust 100 µL to measure the micelle size (see FIG. 16(A)). Also, 16 µL of the portion was taken from the lower-filter solution, and then the portion was diluted to 400 µL to measure the micelle size (see, FIG. 20(A) and FIG. 20(B)).

Zetasizer (Malvern, the cell: ZEN0040) is uses for the particle size measurement. Also, the fluorescent spectrometer RF-5300PC (Shimadzu Corporation) was used for the fluorescent measurement with the excitation wavelength of 370 nm and detection wavelength 488 nm.

(3) Micelle Formation in 50 mM HEPES Buffer (pH 7.6)

As the micelle fraction solution, 50 µM×160 µL was prepared. Concentration in the reaction was 20 µM, and the final concentration was 50 µM. The micelle was formed as the same as those when Tris buffer is used except that 50 mM HEPES buffer (pH 7.6) is used instead of Tris buffer. The separation of the formed micelle was conducted by using Amicon 100 k Filter. Then, the micelle fraction was obtained through buffer exchange to 1×PBS as the same as that conducted in the case of Tris buffer is used.

5 µL of the portion is respectively taken out from the micelle fraction solution or the micelle unreacted fraction solution, and diluted 20 times (2.5 µM) by adding 95 µL of 1×PBS to measure the micelle size (See FIG. 17(A) and FIG. 17(B)).

Figure 21:
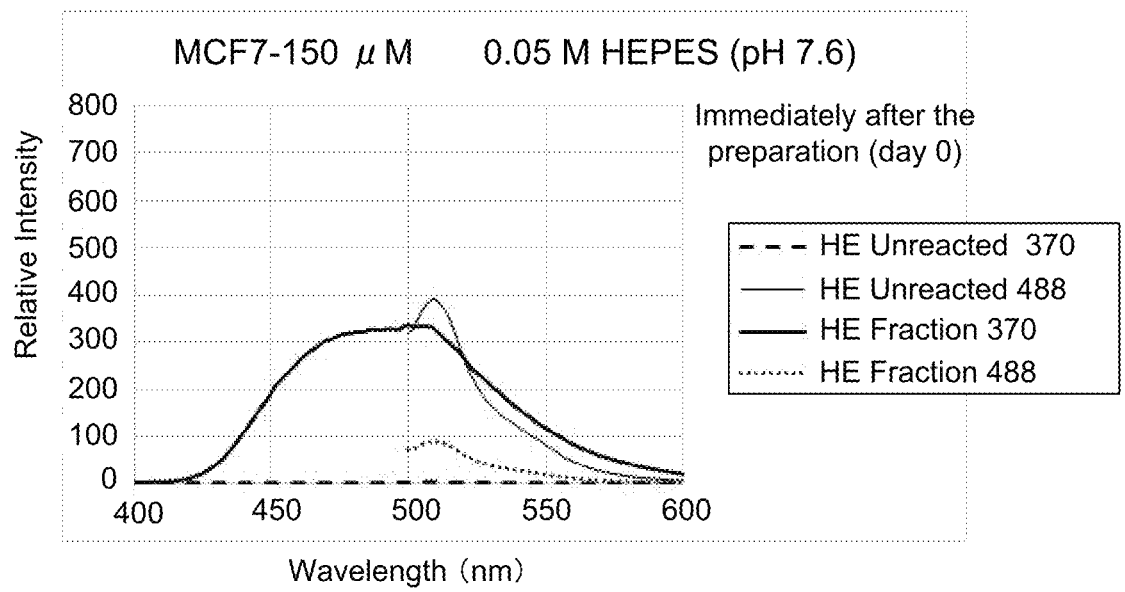
FIG. 21(A) and FIG. 21(B) show the fluorescent characteristic of the micelle, when 50 mM HEPES buffer (pH 7.6) is used.
Figure 21:
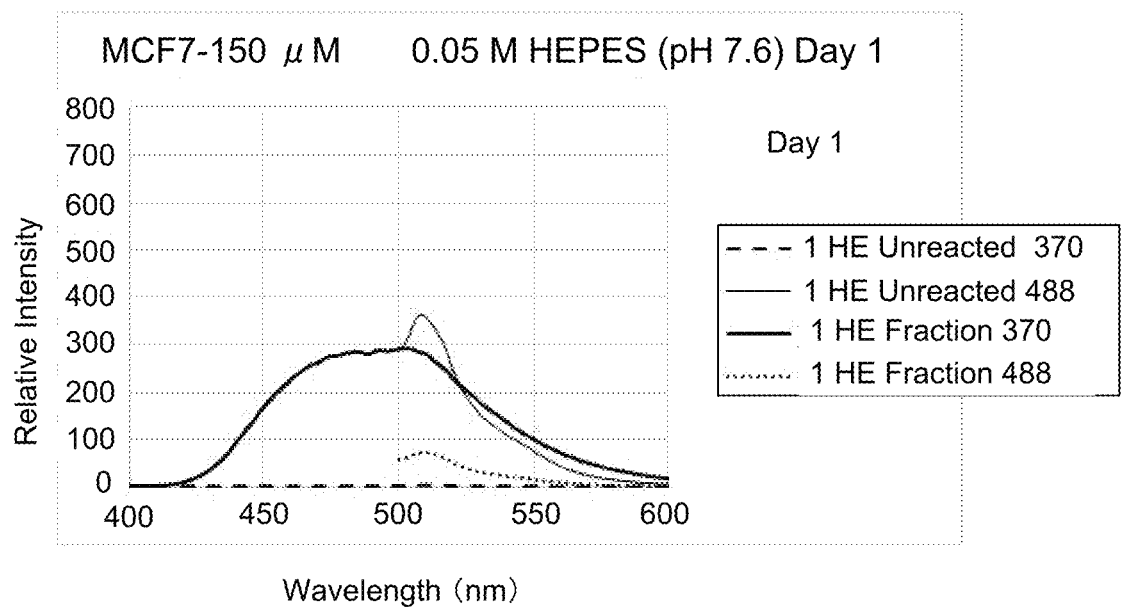

392 µL of 1×PBS is added to 8 µL portion of the micelle fraction solution to prepare 50 times diluted solution (1 µM) to measure its fluorescence. 384 µL of 1×PBS is added to 16 µL of the micelle unreacted solution to prepare 25 times diluted solution to prepare its fluorescence (See, FIG. 21(A)).

(4) The Micelle Formation in 50 mM Citrate Buffer (pH 7.6)

By using sodium citrate is used to prepare 50 mM citrate buffer (pH 7.6). As the micelle fraction solution, 50 µM×160 µL is prepared. The concentration during the reaction is 20 µM, and the final concentration is 50 µM. The micelle was formed as the same as those when Tris buffer is used except that the 50 mM citrate buffer is used, and separated. Then, the micelle fraction was obtained through buffer exchange to 1×PBS as the same as that conducted in the case of Tris buffer is used. 5 µL of the portion is respectively taken out from the micelle fraction solution or the micelle unreacted fraction solution, and diluted 20 times (2.5 µM) by adding 95 µL of 1×PBS to measure the micelle size (See FIG. 18(A) and FIG. 18(B)).

5 µL of the portion is respectively taken out from the micelle fraction solution or the micelle unreacted fraction solution, and diluted 20 times (2.5 µM) by adding 95 µL of 1×PBS to measure the micelle size (See FIG. 18(A) and FIG. 18(B)).

Figure 22:
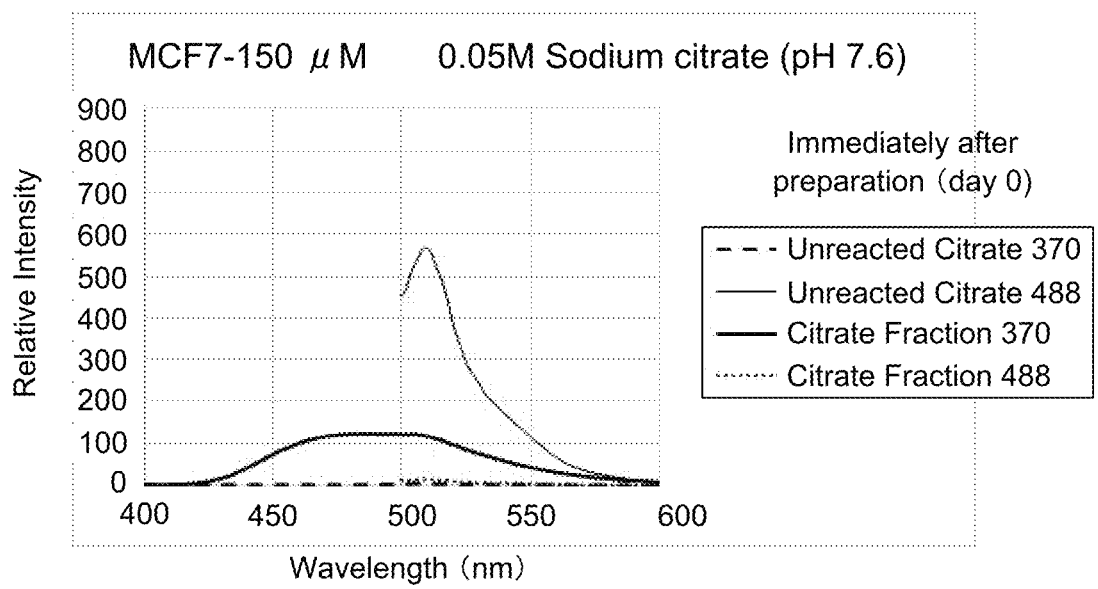
FIG. 22(A) and FIG. 22(B) show the fluorescent characteristic of the micelle, when 50 mM citrate buffer (pH 7.6) is used.
Figure 22:
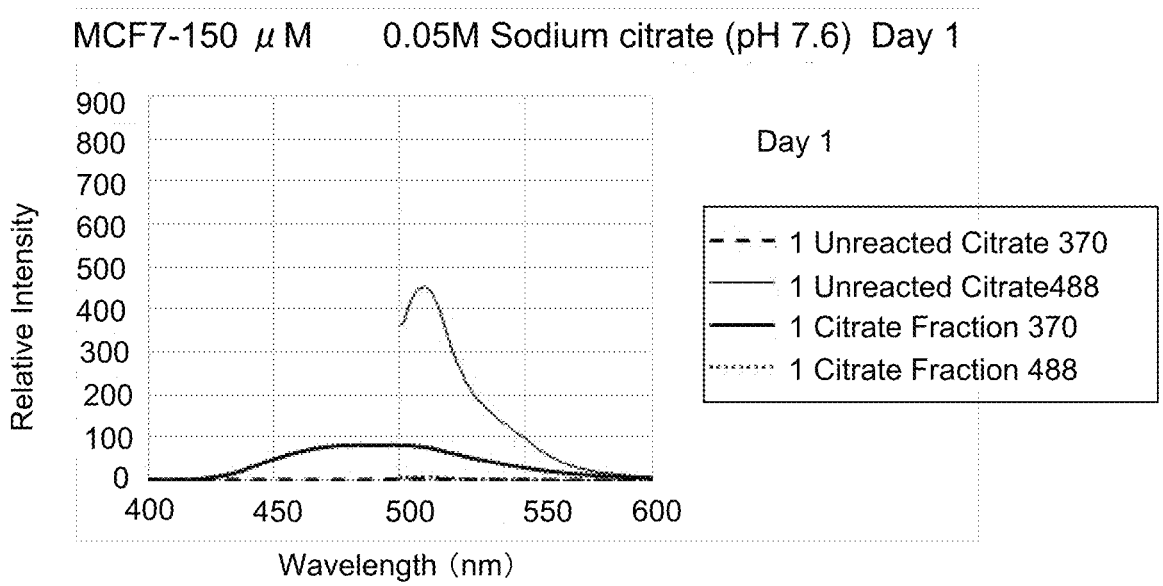

392 µL of 1×PBS is added to 8 µL portion of the micelle fraction solution to prepare 50 times diluted solution (1 µM) to measure its fluorescence. 384 µL of 1×PBS is added to 16 µL of the micelle unreacted solution to prepare 25 times diluted solution to prepare its fluorescence (See, FIG. 22(A)).

(5) The Micelle Formation in 50 mM Carbonate-Bicarbonate Buffer (pH 8.36)

By using sodium bicarbonate, 50 mM carbonate-bicarbonate (pH 8.36) was prepared. As the micelle fraction solution, 50 µM×160 µL is prepared. The micelle was formed as the same as those when the carbonate-bicarbonate (pH 8.36) is used instead of the 50 mM citrate buffer. The separation of the formed micelle was conducted by using Amicon 100 k Filter as the same as that Tris buffer is used. Then, the micelle fraction was obtained through buffer exchange to 1×PBS as the same as that conducted in the case of Tris buffer is used.

5 μL of the portion is respectively taken out from the micelle fraction solution or the micelle unreacted fraction solution, and diluted 20 times (2.5 μM) by adding 95 μL of 1×PBS to measure the micelle size (See FIG. 19(A) and FIG. 19(B)).

Figure 23:
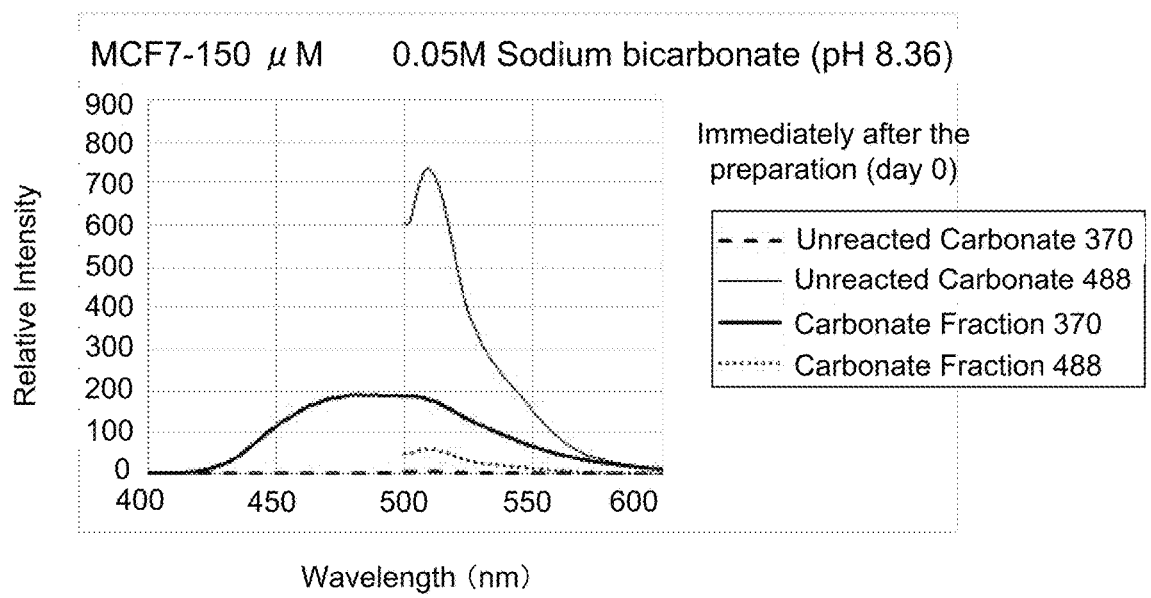
FIG. 23(A) and FIG. 23(B) show the fluorescent characteristic of the micelle, when 50 mM sodium carbonate buffer (pH 7.6) is used.
Figure 23:
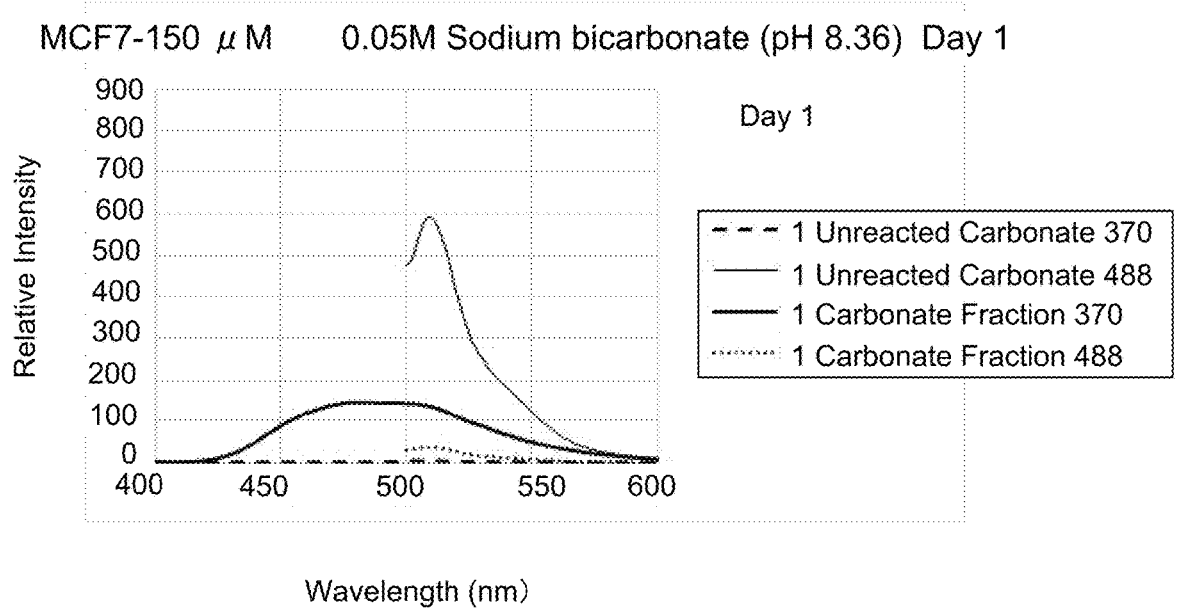

392 μL of 1×PBS is added to 8 μL portion of the micelle fraction solution to prepare 50 times diluted solution (1 μM) to measure its fluorescence. 384 μL of 1×PBS is added to 16 μL of the micelle unreacted solution to prepare 25 times diluted solution to prepare its fluorescence (See, FIG. 23(A)).

(6) Results

As described above, MCF-7 micelle was prepared at the final concentration of 50 μM by using 4 buffers as described above. In the micelle size measurement of each MCF-7 micelle, all of them showed the distribution peak around 100 to 200 nm as the same as those in 1×PBS (FIGS. 16(A) to 19(B)). Also, in the measurement by using the fluorescence spectrometer being set at the excitation wavelength 370 nm, and detection wavelength 488 nm, the same fluorescent spectrum in all of the buffer as that in 1×PBS was observed (FIGS. 20 to 23). Accordingly, it was demonstrated that the MCF-7 micelle is prepared in any buffer among Tris-HCl buffer, HEPES buffer, the carbonate buffer and the citrate buffer similarly to use 1×PBS.

Also, the MCF-7 micelles prepared in each buffer are stored at 4° C., and 1 to 4 days later, they are subjected to the fluorescent analysis under the same conditions as described above. The fluorescent intensity of the micelle used in the above-mentioned buffer showed almost flat, and it demonstrated that they have short-term stabilities (FIGS. 20(B) to 23(B)).

INDUSTRIAL APPLICABILITY

The present invention is useful in the field of the pharmaceutical preparations, particularly in the field of drug delivery.

FREE TEXT FOR SEQUENCE LISTING

SEQ ID NO: 1: Target recognition sequence peptide (MCF7-1) incorporated into GFP
SEQ ID NO: 2: Target recognition sequence peptide (MCF7-2) incorporated into GFP
SEQ ID NO: 3: Target recognition sequence peptide (MCF7-1+α stand) incorporated into GFP
SEQ ID NO: 4: GFP incorporating MCF7-1
SEQ ID NO: 5: GFP incorporating MCF7-2
SEQ ID NO: 6: GFP incorporating MCF7-1+α stand
SEQ ID NO: 7: amino acid sequence of GFP
SEQ ID NO: 8: amino acid sequence of GFP
SEQ ID NO: 9: amino acid sequence of BFP
SEQ ID NO: 10: amino acid sequence of YFP
SEQ ID NO: 11: amino acid sequence of the fluorescent protein derived from Discosoma
SEQ ID NO: 12: forward primer for MCF7-1 amplification
SEQ ID NO: 13: reverse primer for MCF7-1 amplification
SEQ ID NO: 14: forward primer for MCF7-2 amplification
SEQ ID NO: 15: reverse primer for MCF7-2 amplification
SEQ ID NO: 16: forward primer for MCF7-1+α stand amplification
SEQ ID NO: 17: reverse primer for MCF7-1+α stand amplification
SEQ ID NO: 18: forward primer for inverse PCR
SEQ ID NO: 19: reverse primer for inverse PCR
SEQ ID NO: 20: forward primer for inverse PCR 用
SEQ ID NO: 21: reverse primer for inverse PCR
SEQ ID NO: 22: oligonucleotide
SEQ ID NO: 23: oligonucleotide
SEQ ID NO: 24: oligonucleotide
SEQ ID NO: 25: oligonucleotide
SEQ ID NO: 26: forward primer for inverse PCR
SEQ ID NO: 27: reverse primer for inverse PCR
SEQ ID NO: 28: forward primer for inverse PCR
SEQ ID NO: 29: reverse primer for inverse PCR
SEQ ID NO: 30: forward primer for inverse PCR
SEQ ID NO: 31: reverse primer for inverse PCR
SEQ ID NO: 32: forward primer for inverse PCR
SEQ ID NO: 33: reverse primer for inverse PCR
SEQ ID NO: 34: forward primer for inverse PCR

The invention claimed is:

1. An endocytosis enhancing preparation comprising more than one fusion polypeptide comprising a fluorescent protein, and a target recognition sequence selected from the group consisting of SEQ ID NO: 1, SEQ ID NO: 2, and SEQ ID NO: 3.

2. The endocytosis enhancing preparation according to claim 1, wherein said fluorescent proteins are selected from the group consisting of white fluorescent protein, red fluorescent protein, yellow fluorescent protein, blue fluorescent protein, and green fluorescent protein.

3. The endocytosis enhancing preparation according to claim 2 comprising, 2 to 10 molecules of the fluorescent protein.

4. The endocytosis enhancing preparation according to claim 2 further comprising a backbone structure shown in the following formula (I) where n is an integer from 1 to 6 and wherein a micelle is formed

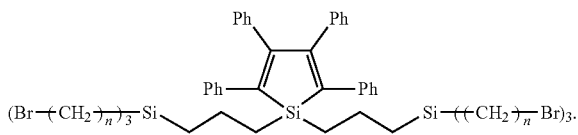

(I)

5. The endocytosis enhancing preparation according to claim 2, wherein the fluorescent protein is green fluorescent protein (GFP) and further comprising a backbone structure selected from the group consisting of the compound shown in the following formula (III) to (VI):

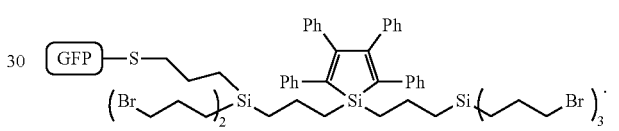

(III)

(IV)

(V)

and (VI)

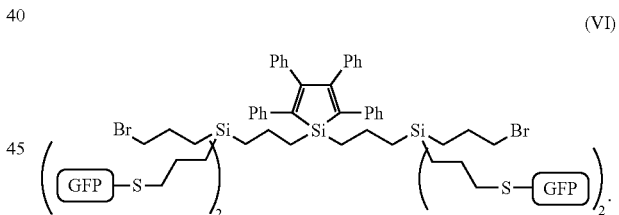

6. The endocytosis enhancing preparation according to claim 1, comprising 4 to 10 molecules of the fluorescent protein.

7. The endocytosis enhancing preparation according to claim 1 further comprising a backbone structure shown in the following formula (I) where n means an integer from 1 to 6 and wherein a micelle is formed

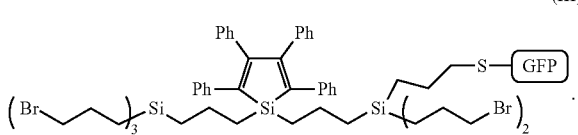

(I)

8. The endocytosis enhancing preparation according to claim), wherein said backbone structure shown in the formula (I) is a compound shown in the following formula (II)

(II)

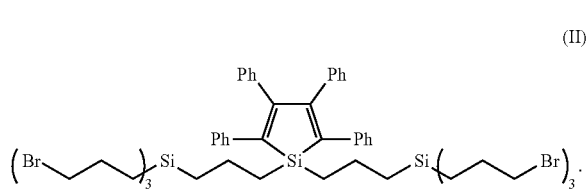

9. The endocytosis enhancing preparation according to claim 1, wherein said micelle is formed so as to have the protein on the outside in the aqueous medium, having a diameter from 50 to 500 nm, and emitting fluorescence derived from FRET.

10. The endocytosis enhancing preparation according to claim 7, wherein said micelle is formed so as to have the protein on the outside in the aqueous medium, having a diameter from 50 to 500 nm, and emitting fluorescence derived from FRET.

11. The endocytosis enhancing preparation according to claim 10, said micelle include any one selected from the group consisting of the molecule having not larger than the molecular weight of 200,000, a nucleic acid, and a lipophilic molecule.

12. The endocytosis enhancing preparation according to claim 11, said molecule having not larger than the molecular weight of 200,000 is preferably selected from the group consisting of immunoglobulin G, lectin, and peptide hormone.

13. The endocytosis enhancing preparation according to claim 1, wherein the fluorescent protein is green fluorescent protein (GFP) and further comprising a backbone structure selected from the group consisting of the compound shown in the following formula (III) to (VI):

(III)

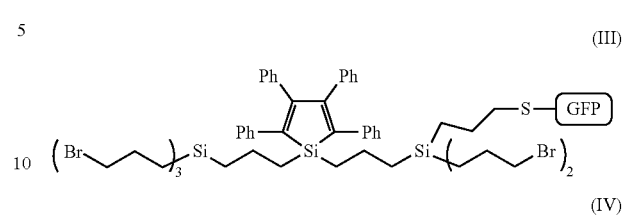

(IV)

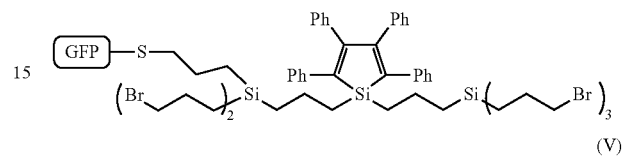

(V)

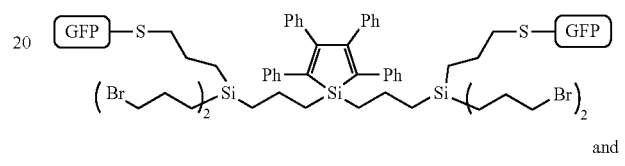

and (VI)

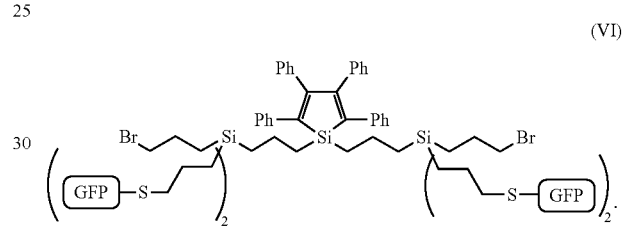

* * * * *